(12) United States Patent
Kamen et al.

(10) Patent No.: US 10,242,159 B2
(45) Date of Patent: Mar. 26, 2019

(54) SYSTEM AND APPARATUS FOR ELECTRONIC PATIENT CARE

(71) Applicant: DEKA Products Limited Partnership, Manchester, NH (US)

(72) Inventors: Dean Kamen, Bedford, NH (US); John J. Biasi, Groton, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 641 days.

(21) Appl. No.: 13/836,497

(22) Filed: Mar. 15, 2013

(65) Prior Publication Data

US 2013/0346108 A1 Dec. 26, 2013

Related U.S. Application Data

(63) Continuation-in-part of application No. 13/333,574, filed on Dec. 21, 2011, which is a
(Continued)

(51) Int. Cl.
*G06F 19/00* (2018.01)
*G06Q 50/22* (2018.01)
(Continued)

(52) U.S. Cl.
CPC ...... *G06F 19/3418* (2013.01); *G06F 19/3468* (2013.01); *G06Q 50/22* (2013.01);
(Continued)

(58) Field of Classification Search
CPC .. G06F 19/3418; G06F 19/00; G06F 19/3468; G06F 19/328; G06F 19/3456;
(Continued)

(56) References Cited

U.S. PATENT DOCUMENTS 3,658,445 A 4/1972 Pulman et al.
4,696,671 A 9/1987 Epstein et al.
(Continued)

FOREIGN PATENT DOCUMENTS

AU 659233 5/1995
AU 738474 9/2001
(Continued)

OTHER PUBLICATIONS

Definition—RSS as downloaded on Jul. 21, 2015.*
(Continued)

*Primary Examiner* — Neal Sereboff
(74) *Attorney, Agent, or Firm* — James D. Wyninegar, Jr.

(57) ABSTRACT

A system for electronic patient care includes a network, a facility gateway, a device gateway application and a medical device. The facility gateway is configured to provide a publish-subscribe service for an application. The device gateway application is configured for execution by the facility gateway. The device gateway is configured to communicate via the network by providing a web service. The medical device is in operative communication with the network. The medical device is configured to communicate with the device gateway using the web service.

24 Claims, 26 Drawing Sheets

Related U.S. Application Data continuation-in-part of application No. 13/011,543, filed on Jan. 21, 2011, application No. 13/836,497, which is a continuation-in-part of application No. PCT/US2011/066588, filed on Dec. 21, 2011, and a continuation-in-part of application No. 13/723,235, filed on Dec. 21, 2012, now Pat. No. 9,400,873, and a continuation-in-part of application No. 13/333,574, filed on Dec. 21, 2011, which is a continuation-in-part of application No. 13/011,543, filed on Jan. 21, 2011, said application No. 13/723,235 is a continuation-in-part of application No. PCT/US2011/066588, filed on Dec. 21, 2011, application No. 13/836,497, which is a continuation-in-part of application No. PCT/US2012/071131, filed on Dec. 21, 2012, which is a continuation-in-part of application No. 13/333,574, filed on Dec. 21, 2011, which is a continuation-in-part of application No. 13/011,543, filed on Jan. 21, 2011, said application No. PCT/US2012/071131 is a continuation-in-part of application No. PCT/US2011/066588, filed on Dec. 21, 2011, application No. 13/836,497, which is a continuation-in-part of application No. 13/724,568, filed on Dec. 21, 2012, now Pat. No. 9,295,778, and a continuation-in-part of application No. 13/333,574, filed on Dec. 21, 2011, which is a continuation-in-part of application No. 13/011,543, filed on Jan. 21, 2011, said application No. 13/724,568 is a continuation-in-part of application No. PCT/US2011/066588, filed on Dec. 21, 2011, application No. 13/836,497, which is a continuation-in-part of application No. 13/725,790, filed on Dec. 21, 2012, now Pat. No. 9,677,555, and a continuation-in-part of application No. 13/333,574, filed on Dec. 21, 2011, which is a continuation-in-part of application No. 13/011,543, filed on Jan. 21, 2011, said application No. 13/725,790 is a continuation-in-part of application No. PCT/US2011/066588, filed on Dec. 21, 2011, application No. 13/836,497, which is a continuation-in-part of application No. PCT/US2012/071490, filed on Dec. 21, 2012, and a continuation of application No. 13/333,574, filed on Dec. 21, 2011, which is a continuation-in-part of application No. 13/011,543, filed on Jan. 21, 2011, said application No. PCT/US2012/071490 is a continuation-in-part of application No. PCT/US2011/066588, filed on Dec. 21, 2011, application No. 13/836,497, which is a continuation-in-part of application No. 13/723,239, filed on Dec. 21, 2012, now Pat. No. 10,108,785, and a continuation-in-part of application No. 13/333,574, filed on Dec. 21, 2011, which is a continuation-in-part of application No. 13/011,543, filed on Jan. 21, 2011, said application No. 13/723,239 is a continuation-in-part of application No. PCT/US2011/066588, filed on Dec. 21, 2011, application No. 13/836,497, which is a continuation-in-part of application No. 13/723,242, filed on Dec. 21, 2012, application No. 13/836,497, which is a continuation-in-part of application No. 13/723,244, filed on Dec. 21, 2012, now Pat. No. 9,151,646, and a continuation-in-part of application No. 13/333,574, filed on Dec. 21, 2011, which is a continuation-in-part of application No. 13/011,543, filed on Jan. 21, 2011, said application No. 13/723,244 is a continuation-in-part of application No. PCT/US2011/066588, filed on Dec. 21, 2011, application No. 13/836,497, which is a continuation-in-part of application No. PCT/US2012/071142, filed on Dec. 21, 2012, and a continuation-in-part of application No. 13/333,574, filed on Dec. 21, 2011, which is a continuation-in-part of application No. 13/011,543, filed on Jan. 21, 2011, said application No. PCT/US2012/071142 is a continuation-in-part of application No. PCT/US2011/066588, filed on Dec. 21, 2011, application No. 13/836,497, which is a continuation-in-part of application No. 13/723,251, filed on Dec. 21, 2012, now Pat. No. 9,636,455, and a continuation-in-part of application No. 13/333,574, filed on Dec. 21, 2012, which is a continuation-in-part of application No. PCT/US2011/066588, filed on Dec. 21, 2011, application No. 13/836,497, which is a continuation-in-part of application No. PCT/US2012/071112, filed on Dec. 21, 2012, and a continuation-in-part of application No. 13/333,574, filed on Dec. 21, 2011, which is a continuation-in-part of application No. 13/011,543, filed on Jan. 21, 2011, said application No. PCT/US2012/071112 is a continuation-in-part of application No. PCT/US2011/066588, filed on Dec. 21, 2011, application No. 13/836,497, which is a continuation-in-part of application No. 13/723,253, filed on Dec. 21, 2012, and a continuation-in-part of application No. 13/333,574, filed on Dec. 21, 2011, and a continuation-in-part of application No. PCT/US2011/066588, filed on Dec. 21, 2011, said application No. 13/333,574 is a continuation-in-part of application No. 13/011,543, filed on Jan. 21, 2011.

(60) Provisional application No. 61/297,544, filed on Jan. 22, 2010, provisional application No. 61/578,649, filed on Dec. 21, 2011, provisional application No. 61/578,658, filed on Dec. 21, 2011, provisional application No. 61/578,674, filed on Dec. 21, 2011, provisional application No. 61/679,117, filed on Aug. 3, 2012, provisional application No. 61/651,322, filed on May 24, 2012.

(51) Int. Cl.
*G16H 40/40* (2018.01)
*G16H 40/63* (2018.01)

(52) U.S. Cl.
CPC ............. *G16H 40/40* (2018.01); *G16H 40/63* (2018.01); *G06F 19/328* (2013.01)

(58) Field of Classification Search
CPC .... G06F 19/3462; G06Q 50/24; G06Q 50/22; G06Q 10/06; G06Q 10/10; G06Q 10/103; G06Q 10/107; G06Q 10/109
See application file for complete search history.

(56) References Cited

U.S. PATENT DOCUMENTS

| | | |
|---|---|---|
| 4,877,034 A | 10/1989 | Atkins et al. |
| 4,939,689 A | 7/1990 | Davis et al. |
| 5,041,086 A | 8/1991 | Koenig et al. |
| 5,207,642 A | 5/1993 | Orkin et al. |
| 5,317,506 A | 5/1994 | Coutre et al. |
| D348,101 S | 6/1994 | Poli et al. |
| 5,368,562 A | 11/1994 | Blomquist et al. |
| 5,482,446 A | 1/1996 | Williamson |
| 5,485,408 A | 1/1996 | Blomquist |
| 5,527,289 A | 6/1996 | Foster et al. |
| 5,537,618 A | 7/1996 | Boulton et al. |
| 5,713,856 A | 2/1998 | Eggers et al. |

(56) References Cited

U.S. PATENT DOCUMENTS

| | | | |
|---|---|---|---|
| 5,719,761 | A | 2/1998 | Gatti et al. |
| 5,781,442 | A | 7/1998 | Engleson et al. |
| 5,836,910 | A | 11/1998 | Duffy et al. |
| 5,941,846 | A | 8/1999 | Duffy et al. |
| 5,961,487 | A | 10/1999 | Davis |
| 6,021,392 | A | 2/2000 | Lester et al. |
| 6,024,539 | A | 2/2000 | Blomquist |
| 6,139,495 | A | 10/2000 | De La Huerga |
| 6,255,951 | B1 | 7/2001 | De La Huerga |
| 6,267,559 | B1 | 7/2001 | Mossman et al. |
| 6,308,171 | B1 | 10/2001 | De La Huerga |
| 6,314,384 | B1 | 11/2001 | Goetz |
| 6,315,720 | B1 | 11/2001 | Williams et al. |
| 6,317,719 | B1 | 11/2001 | Schrier et al. |
| 6,319,200 | B1 | 11/2001 | Lai et al. |
| 6,327,570 | B1 | 12/2001 | Stevens |
| 6,346,886 | B1 | 2/2002 | De La Huerga |
| 6,348,777 | B1 | 2/2002 | Brown et al. |
| 6,398,727 | B1 | 6/2002 | Bue et al. |
| 6,408,330 | B1 | 6/2002 | De La Huerga |
| 6,421,650 | B1 | 7/2002 | Goetz et al. |
| 6,427,088 | B1 | 7/2002 | Dowman, IV et al. |
| 6,519,569 | B1 | 2/2003 | White et al. |
| 6,554,798 | B1 | 4/2003 | Mann et al. |
| 6,579,242 | B2 | 6/2003 | Bui et al. |
| 6,668,196 | B1 | 12/2003 | Villegas et al. |
| 6,671,563 | B1 | 12/2003 | Engelson et al. |
| 6,694,334 | B2 | 2/2004 | DuLong et al. |
| 6,745,764 | B2 | 6/2004 | Hickle |
| 6,775,577 | B2 | 8/2004 | Crnkovich et al. |
| 6,790,198 | B1 | 9/2004 | White et al. |
| 6,880,034 | B2 | 4/2005 | Mabke et al. |
| 6,976,349 | B2 | 12/2005 | Baldwin et al. |
| 6,985,870 | B2 | 1/2006 | Martucci et al. |
| 6,993,402 | B2 | 1/2006 | Klass et al. |
| 7,039,878 | B2 | 5/2006 | Auer et al. |
| 7,096,072 | B2 | 8/2006 | Engleson et al. |
| 7,103,419 | B2 | 9/2006 | Engleson et al. |
| 7,107,106 | B2 | 9/2006 | Engleson et al. |
| 7,117,041 | B2 | 10/2006 | Engleson et al. |
| 7,161,484 | B2 | 1/2007 | Tsoukalis |
| 7,165,221 | B2 | 1/2007 | Monteleone et al. |
| 7,171,277 | B2 | 1/2007 | Engleson et al. |
| 7,216,802 | B1 | 5/2007 | De La Huerga |
| 7,236,936 | B2 | 6/2007 | White et al. |
| 7,300,418 | B2 | 11/2007 | Zaleski |
| 7,303,549 | B2 | 12/2007 | Flaherty et al. |
| 7,379,885 | B1 | 5/2008 | Zakim |
| 7,384,410 | B2 | 6/2008 | Eggers et al. |
| 7,433,853 | B2 | 10/2008 | Brockway et al. |
| 7,452,190 | B2 | 11/2008 | Bouton et al. |
| 7,471,994 | B2 | 12/2008 | Ford et al. |
| 7,539,593 | B2 | 5/2009 | Machacek |
| 7,565,301 | B2 | 7/2009 | Moubayed et al. |
| 7,569,030 | B2 | 8/2009 | Lebel et al. |
| 7,590,551 | B2 | 9/2009 | Auer |
| 7,612,679 | B1 | 11/2009 | Fackler et al. |
| 7,636,718 | B1 | 12/2009 | Steen et al. |
| 7,645,258 | B2 | 1/2010 | White et al. |
| 7,647,237 | B2 | 1/2010 | Malave et al. |
| 7,664,660 | B2 | 2/2010 | Korpman et al. |
| 7,678,071 | B2 | 3/2010 | Lebel et al. |
| 7,685,003 | B2 | 3/2010 | Hasan et al. |
| 7,689,394 | B2 | 3/2010 | Furem et al. |
| 7,693,730 | B2 | 4/2010 | Hasan et al. |
| 7,699,806 | B2 | 4/2010 | Ware et al. |
| 7,703,042 | B2 | 4/2010 | Brummel et al. |
| 7,707,047 | B2 | 4/2010 | Hasan et al. |
| 7,715,277 | B2 | 5/2010 | De La Huerga |
| 7,743,975 | B2 | 6/2010 | Miller |
| 7,771,385 | B2 | 8/2010 | Eggers et al. |
| 7,771,386 | B2 | 8/2010 | Eggers et al. |
| 7,788,369 | B2 | 8/2010 | McAllen et al. |
| 7,813,879 | B2 | 10/2010 | Bush et al. |
| 7,815,602 | B2 | 10/2010 | Mann et al. |
| 7,818,184 | B2 | 10/2010 | Penny et al. |
| 7,819,843 | B2 | 10/2010 | Mann et al. |
| 7,831,446 | B2 | 11/2010 | Korpman et al. |
| 7,835,927 | B2 | 11/2010 | Schlotterbeck et al. |
| 7,839,266 | B2 | 11/2010 | Hoglund et al. |
| 7,850,641 | B2 | 12/2010 | Lebel et al. |
| 7,859,401 | B2 | 12/2010 | Falck et al. |
| 7,860,583 | B2 | 12/2010 | Condurso et al. |
| 7,871,394 | B2 | 1/2011 | Helbert et al. |
| 7,873,489 | B2 | 1/2011 | Dolgos et al. |
| 7,886,231 | B2 | 2/2011 | Hopermann et al. |
| 7,893,876 | B2 | 2/2011 | Brown et al. |
| 7,896,842 | B2 | 3/2011 | Palmroos et al. |
| 7,901,394 | B2 | 3/2011 | Ireland et al. |
| 7,911,353 | B2 | 3/2011 | Bedingfield |
| D636,779 | S | 4/2011 | Boush et al. |
| D636,780 | S | 4/2011 | Musleh |
| 7,933,780 | B2 | 4/2011 | De La Huerga |
| 7,935,076 | B2 | 5/2011 | Estes et al. |
| 7,938,796 | B2 | 5/2011 | Moubayed et al. |
| 7,941,534 | B2 | 5/2011 | De La Huerga |
| 7,942,844 | B2 | 5/2011 | Moberg et al. |
| 7,946,985 | B2 | 5/2011 | Mastrototaro et al. |
| 7,955,289 | B2 | 6/2011 | O'Mahony et al. |
| 7,976,508 | B2 | 7/2011 | Hoag |
| 7,978,564 | B2 | 7/2011 | De La Huerga |
| 8,025,634 | B1 | 9/2011 | Moubayed et al. |
| 8,032,226 | B2 | 10/2011 | Miller et al. |
| 8,038,593 | B2 | 10/2011 | Friedman et al. |
| 8,041,542 | B2 | 10/2011 | Pearson |
| 8,060,381 | B2 | 11/2011 | Dyer et al. |
| 8,073,710 | B2 | 12/2011 | Hasan et al. |
| 8,095,390 | B2 | 1/2012 | Bluemler et al. |
| 8,099,301 | B2 | 1/2012 | Keresman, III et al. |
| 8,126,728 | B2 | 2/2012 | Dicks et al. |
| 8,126,729 | B2 | 2/2012 | Dicks et al. |
| 8,131,565 | B2 | 3/2012 | Dicks et al. |
| 8,131,566 | B2 | 3/2012 | Dicks et al. |
| 8,134,459 | B2 | 3/2012 | Smith et al. |
| 8,149,131 | B2 | 4/2012 | Blomquist |
| 8,152,486 | B2 | 4/2012 | Fathallah et al. |
| 8,178,040 | B2 | 5/2012 | Brauer |
| 8,192,394 | B2 | 6/2012 | Estes et al. |
| 8,214,227 | B2 | 7/2012 | Patterson et al. |
| 8,214,234 | B2 | 7/2012 | Hasan et al. |
| 8,217,946 | B2 | 7/2012 | Halpern et al. |
| 8,219,413 | B2 | 7/2012 | Martinez et al. |
| 8,219,982 | B2 | 7/2012 | Harkanyi et al. |
| 8,222,768 | B2 | 7/2012 | Cassidy |
| 8,225,015 | B2 | 7/2012 | Gao-Saari et al. |
| 8,229,760 | B2 | 7/2012 | Hasan et al. |
| D665,401 | S | 8/2012 | Rai et al. |
| 8,235,938 | B2 | 8/2012 | Eggers et al. |
| 8,239,780 | B2 | 8/2012 | Manetta et al. |
| 8,244,555 | B2 | 8/2012 | Masson et al. |
| 8,255,585 | B2 | 8/2012 | Levin |
| 8,260,635 | B2 | 9/2012 | Hasan et al. |
| 8,271,106 | B2 | 9/2012 | Wehbaf et al. |
| 8,273,018 | B1 | 9/2012 | Fackler et al. |
| 8,275,576 | B2 | 9/2012 | Furem et al. |
| 8,275,633 | B2 | 9/2012 | Baker |
| 8,291,337 | B2 | 10/2012 | Gannin et al. |
| 8,306,797 | B2 | 11/2012 | Furem et al. |
| 8,308,680 | B1 | 11/2012 | Chawla |
| 8,312,877 | B2 | 11/2012 | Elaz et al. |
| 8,317,752 | B2 | 11/2012 | Cozmi et al. |
| D672,785 | S | 12/2012 | Rai et al. |
| 8,340,792 | B2 | 12/2012 | Condurso et al. |
| 8,352,290 | B2 | 1/2013 | Bartz et al. |
| 8,359,338 | B2 | 1/2013 | Butterfield et al. |
| 8,373,557 | B2 | 2/2013 | Smith et al. |
| 8,380,536 | B2 | 2/2013 | Howard et al. |
| 8,414,523 | B2 | 4/2013 | Blomquist et al. |
| D682,861 | S | 5/2013 | Rounding et al. |
| 8,444,595 | B2 | 5/2013 | Brukalo et al. |
| 8,451,230 | B2 | 5/2013 | Celentano et al. |
| D694,774 | S | 12/2013 | Schuller et al. |
| D701,526 | S | 3/2014 | Poston et al. |
| D705,242 | S | 5/2014 | Bohmfalk et al. |

(56) References Cited

U.S. PATENT DOCUMENTS

| | | | |
|---|---|---|---|
| D709,905 S | 7/2014 | Bohmfalk et al. | |
| D714,339 S | 9/2014 | Hendrickson et al. | |
| 8,938,684 B2 | 1/2015 | Guertler et al. | |
| 8,954,336 B2 | 2/2015 | Bloomquist | |
| D726,752 S | 4/2015 | Angelides | |
| D728,601 S | 5/2015 | Angelides | |
| D733,724 S | 7/2015 | Kim | |
| 2001/0031944 A1 | 10/2001 | Peterson et al. | |
| 2001/0051787 A1* | 12/2001 | Haller | A61B 5/0031 604/66 |
| 2002/0013538 A1 | 1/2002 | Teller | |
| 2002/0184589 A1 | 12/2002 | Eatough et al. | |
| 2002/0188465 A1 | 12/2002 | Gogolak et al. | |
| 2003/0046110 A1 | 3/2003 | Gogolak | |
| 2003/0061073 A1 | 3/2003 | Seow et al. | |
| 2003/0106553 A1 | 6/2003 | Vanderveen | |
| 2003/0114751 A1 | 6/2003 | Pedain et al. | |
| 2003/0135388 A1 | 7/2003 | Martucci et al. | |
| 2004/0010425 A1 | 1/2004 | Wilkes et al. | |
| 2004/0015132 A1 | 1/2004 | Brown | |
| 2004/0147818 A1 | 7/2004 | Levy et al. | |
| 2004/0158193 A1 | 8/2004 | Bui et al. | |
| 2004/0172283 A1 | 9/2004 | Vanderveen et al. | |
| 2004/0193325 A1 | 9/2004 | Bonderud et al. | |
| 2004/0193453 A1 | 9/2004 | Bonderud et al. | |
| 2005/0022184 A1 | 1/2005 | Birkestrand et al. | |
| 2005/0055242 A1 | 3/2005 | Bello et al. | |
| 2005/0070767 A1 | 3/2005 | Maschke | |
| 2005/0099624 A1 | 5/2005 | Staehr et al. | |
| 2005/0144043 A1 | 6/2005 | Holland et al. | |
| 2005/0171815 A1 | 8/2005 | Vanderveen | |
| 2005/0177096 A1 | 8/2005 | Bollish et al. | |
| 2005/0224083 A1 | 10/2005 | Crass et al. | |
| 2006/0047538 A1 | 3/2006 | Condurso et al. | |
| 2006/0080140 A1 | 4/2006 | Buttner et al. | |
| 2006/0095300 A1 | 5/2006 | Schrier et al. | |
| 2006/0149140 A1 | 7/2006 | Eldridge | |
| 2006/0149591 A1 | 7/2006 | Hanf et al. | |
| 2006/0184123 A1 | 8/2006 | Gillespie, Jr. et al. | |
| 2006/0258985 A1 | 11/2006 | Russell | |
| 2006/0265246 A1 | 11/2006 | Hoag | |
| 2007/0061393 A1* | 3/2007 | Moore | G06F 17/3089 709/201 |
| 2007/0088574 A1 | 4/2007 | Byer et al. | |
| 2007/0109325 A1 | 5/2007 | Eveleigh | |
| 2007/0136090 A1 | 6/2007 | Loutzenhiser et al. | |
| 2007/0191817 A1 | 8/2007 | Martin | |
| 2007/0250927 A1 | 10/2007 | Naik et al. | |
| 2007/0255348 A1* | 11/2007 | Holtzclaw | A61B 5/0002 607/60 |
| 2008/0039744 A1 | 2/2008 | Hamilton | |
| 2008/0091175 A1 | 4/2008 | Frikart et al. | |
| 2008/0097913 A1 | 4/2008 | Dicks et al. | |
| 2008/0129496 A1 | 6/2008 | Koblasz | |
| 2008/0133265 A1 | 6/2008 | Silkaitis et al. | |
| 2008/0140157 A1 | 6/2008 | Goetz et al. | |
| 2008/0235765 A1 | 9/2008 | Shimizu | |
| 2008/0243055 A1 | 10/2008 | Fathallah et al. | |
| 2008/0255438 A1 | 10/2008 | Saidara et al. | |
| 2008/0262441 A1 | 10/2008 | Walborn et al. | |
| 2009/0069743 A1 | 3/2009 | Krishnamoorthy et al. | |
| 2009/0099867 A1 | 4/2009 | Newman | |
| 2009/0150818 A1 | 6/2009 | Bakhreiba et al. | |
| 2009/0153058 A1 | 6/2009 | Feng et al. | |
| 2009/0153463 A1 | 6/2009 | Arrizza et al. | |
| 2009/0153595 A1 | 6/2009 | Cozmi et al. | |
| 2009/0157432 A1 | 6/2009 | Palmroos et al. | |
| 2009/0183147 A1 | 7/2009 | Davis et al. | |
| 2009/0203329 A1 | 8/2009 | White et al. | |
| 2009/0216562 A1 | 8/2009 | Faulkner et al. | |
| 2009/0234672 A1 | 9/2009 | Dicks et al. | |
| 2009/0240526 A1 | 9/2009 | Vesto et al. | |
| 2010/0094653 A1 | 4/2010 | Tribble et al. | |
| 2010/0114027 A1 | 5/2010 | Jacobson et al. | |
| 2010/0130933 A1 | 5/2010 | Holland et al. | |
| 2010/0229096 A1 | 9/2010 | Maiocco et al. | |
| 2010/0234718 A1 | 9/2010 | Sampath et al. | |
| 2010/0257189 A1 | 10/2010 | Campbell et al. | |
| 2010/0268157 A1 | 10/2010 | Wehba et al. | |
| 2010/0280486 A1 | 11/2010 | Khair et al. | |
| 2010/0287006 A1* | 11/2010 | Cannon | G06Q 10/06 705/3 |
| 2010/0292556 A1 | 11/2010 | Golden | |
| 2010/0298662 A1 | 11/2010 | Yu et al. | |
| 2011/0004186 A1 | 1/2011 | Butterfield | |
| 2011/0105979 A1 | 5/2011 | Schlaeper et al. | |
| 2011/0119612 A1 | 5/2011 | Gannon et al. | |
| 2011/0153343 A1 | 6/2011 | Tremblay et al. | |
| 2011/0167250 A1 | 7/2011 | Dicks et al. | |
| 2011/0173704 A1 | 7/2011 | Hanov et al. | |
| 2011/0179405 A1 | 7/2011 | Dicks et al. | |
| 2011/0184379 A1 | 7/2011 | Van Antwerp et al. | |
| 2011/0196306 A1 | 8/2011 | De La Huerga | |
| 2011/0205965 A1 | 8/2011 | Sprigg et al. | |
| 2011/0224646 A1 | 9/2011 | Yodfat et al. | |
| 2011/0231203 A1 | 9/2011 | Rosow et al. | |
| 2011/0231204 A1 | 9/2011 | De La Huerga | |
| 2011/0241878 A1 | 10/2011 | Hoag | |
| 2011/0276605 A1 | 11/2011 | Masson et al. | |
| 2011/0282168 A1 | 11/2011 | Weiss et al. | |
| 2011/0282688 A1 | 11/2011 | Raggousis | |
| 2011/0282691 A1 | 11/2011 | Coffman et al. | |
| 2011/0313789 A1 | 12/2011 | Kamen et al. | |
| 2011/0320049 A1 | 12/2011 | Chossat et al. | |
| 2012/0011253 A1 | 1/2012 | Friedman et al. | |
| 2012/0016215 A1 | 1/2012 | Condurson et al. | |
| 2012/0016295 A1 | 1/2012 | Tsoukalis | |
| 2012/0029300 A1 | 2/2012 | Paquet | |
| 2012/0029307 A1 | 2/2012 | Paquet et al. | |
| 2012/0029308 A1 | 2/2012 | Paquet | |
| 2012/0029309 A1 | 2/2012 | Paquet et al. | |
| 2012/0029310 A1 | 2/2012 | Paquet et al. | |
| 2012/0029311 A1 | 2/2012 | Raptis et al. | |
| 2012/0029312 A1 | 2/2012 | Beaudry et al. | |
| 2012/0029314 A1 | 2/2012 | Paquet et al. | |
| 2012/0029315 A1 | 2/2012 | Raptis et al. | |
| 2012/0029316 A1 | 2/2012 | Raptis et al. | |
| 2012/0029941 A1 | 2/2012 | Malave et al. | |
| 2012/0030547 A1 | 2/2012 | Raptis et al. | |
| 2012/0053533 A1 | 3/2012 | Butterfield et al. | |
| 2012/0062387 A1 | 3/2012 | Vik et al. | |
| 2012/0065990 A1 | 3/2012 | Howard et al. | |
| 2012/0066609 A1 | 3/2012 | Howard et al. | |
| 2012/0075061 A1 | 3/2012 | Barnes | |
| 2012/0078218 A1 | 3/2012 | Barnes | |
| 2012/0084303 A1 | 4/2012 | Ledford et al. | |
| 2012/0116796 A1 | 5/2012 | Bellown et al. | |
| 2012/0116800 A1 | 5/2012 | McCallie et al. | |
| 2012/0123229 A1 | 5/2012 | Butterfield et al. | |
| 2012/0124174 A1 | 5/2012 | Nudelman et al. | |
| 2012/0130308 A1 | 5/2012 | Silkaitis et al. | |
| 2012/0157920 A1 | 6/2012 | Flachbart et al. | |
| 2012/0172802 A1 | 7/2012 | Blomquist | |
| 2012/0176394 A1 | 7/2012 | Vik et al. | |
| 2012/0179093 A1 | 7/2012 | Rinehart et al. | |
| 2012/0179136 A1 | 7/2012 | Rinehart et al. | |
| 2012/0185267 A1 | 7/2012 | Kamen et al. | |
| 2012/0239824 A1 | 9/2012 | Nguyen et al. | |
| 2012/0260012 A1 | 10/2012 | Gao-Saari et al. | |
| 2012/0302991 A1 | 11/2012 | Blomquist et al. | |
| 2012/0310205 A1 | 12/2012 | Lee et al. | |
| 2013/0006651 A1 | 1/2013 | Saus et al. | |
| 2013/0006666 A1 | 1/2013 | Schneider et al. | |
| 2013/0012880 A1 | 1/2013 | Blomquist | |
| 2013/0030830 A1 | 1/2013 | Schmoll et al. | |
| 2013/0042194 A1 | 2/2013 | Gannon et al. | |
| 2013/0045764 A1 | 2/2013 | Vik et al. | |
| 2013/0046871 A1 | 2/2013 | Vik et al. | |
| 2013/0091191 A1 | 4/2013 | Levin et al. | |
| 2013/0104120 A1 | 4/2013 | Arrizza et al. | |
| 2013/0133036 A1 | 5/2013 | Wang et al. | |
| 2013/0141329 A1 | 6/2013 | Halbert et al. | |
| 2013/0177455 A1 | 7/2013 | Kamen et al. | |
| 2013/0182381 A1 | 7/2013 | Gray et al. | |

(56) References Cited

U.S. PATENT DOCUMENTS

| | | |
|---|---|---|
| 2013/0184676 A1 | 7/2013 | Kamen et al. |
| 2013/0188040 A1 | 7/2013 | Kamen et al. |
| 2013/0191513 A1 | 7/2013 | Kamen et al. |
| 2013/0197693 A1 | 8/2013 | Kamen et al. |
| 2013/0204188 A1 | 8/2013 | Kamen et al. |
| 2013/0227462 A1 | 8/2013 | Hsu |

FOREIGN PATENT DOCUMENTS

| | | |
|---|---|---|
| AU | 2003265858 B2 | 4/2003 |
| AU | 2003256732 B2 | 7/2003 |
| EP | 0 760 244 B1 | 3/1977 |
| EP | 319268 B1 | 6/1989 |
| EP | 473240 B1 | 6/1994 |
| EP | 477551 B1 | 1/1995 |
| EP | 960627 A2 | 12/1999 |
| EP | 612004 B2 | 4/2000 |
| EP | 1640028 A2 | 3/2006 |
| EP | 1722310 A1 | 11/2006 |
| EP | 1744262 A2 | 1/2007 |
| EP | 1944709 A1 | 7/2007 |
| EP | 2278511 A2 | 1/2011 |
| EP | 2330524 A2 | 6/2011 |
| EP | 649316 B2 | 8/2013 |
| GB | 2 020 735 A | 11/1979 |
| JP | 2004523305 | 8/2004 |
| JP | 2011243549 A | 12/2011 |
| WO | WO 93/04285 | 3/1993 |
| WO | WO 1993/010835 A1 | 6/1993 |
| WO | WO 1993/021978 A1 | 11/1993 |
| WO | WO 1998/014234 A1 | 4/1998 |
| WO | WO 1999/052575 A1 | 10/1999 |
| WO | WO 2000/072181 A2 | 11/2000 |
| WO | WO 01/98876 A2 | 12/2001 |
| WO | WO 2002/068018 A2 | 9/2002 |
| WO | WO 2002/100262 A1 | 12/2002 |
| WO | WO 2003/094091 A1 | 11/2003 |
| WO | WO 2003/105931 A1 | 12/2003 |
| WO | WO 2004/012043 A2 | 2/2004 |
| WO | WO 2004/029853 A2 | 4/2004 |
| WO | WO 2004/087241 A1 | 10/2004 |
| WO | WO 2005/065750 A1 | 7/2005 |
| WO | WO 2005/089263 A2 | 9/2005 |
| WO | WO 2006/060291 A2 | 6/2006 |
| WO | WO 2006/086723 A2 | 8/2006 |
| WO | WO 2006/086735 A2 | 8/2006 |
| WO | WO 2006/121510 A2 | 11/2006 |
| WO | WO 2007/113709 A1 | 10/2007 |
| WO | WO 2008/022880 A1 | 2/2008 |
| WO | WO 2008/031821 A1 | 3/2008 |
| WO | WO 2009/003196 A1 | 12/2008 |
| WO | WO 2010/045119 A2 | 4/2010 |
| WO | WO 2010/085867 A1 | 8/2010 |
| WO | WO 2010/129720 A2 | 11/2010 |
| WO | WO 2011/021098 A1 | 2/2011 |
| WO | WO 2011/066556 A1 | 6/2011 |
| WO | WO 2011/091998 A1 | 8/2011 |
| WO | WO 2011/109500 A1 | 9/2011 |
| WO | WO 2011/119810 A1 | 9/2011 |
| WO | WO 2013/095459 A1 | 6/2013 |
| WO | WO 2013/096713 A2 | 6/2013 |
| WO | WO 2013/096718 A2 | 6/2013 |
| WO | WO 2013/096722 A2 | 6/2013 |
| WO | WO 2013/096909 A2 | 6/2013 |
| WO | PCT/US15/16796 | 2/2015 |
| WO | PCT/US15/49952 | 9/2015 |
| WO | PCT/US2015/63359 | 12/2015 |

OTHER PUBLICATIONS

Definition—wifi as downloaded on Jul. 23, 2015.*
Greg, "HOWTO: Port-Forwarding" The NW Blog, Oct. 22, 2007 www.networkwebcams.co.uk/blog.*

AAMI and FDA, Infusing Patients Safely: Priority Issues from the AAMI/FDA Infusion Device Summit, Symposium, Oct. 5-6, 2010, pp. 1-48, AAMI, Arlington, VA, USA.
Office Action and Formal Examination dated Aug. 24, 2015, received in Columbian application No. 15168128 (L52C0), 9-13—English Translation of same, pp. 1-8.
Office Action and Formal Examination dated Aug. 28, 2015, received in Columbian application No. 15167289 (K22C0), 10-16—English Translation of same, pp. 1-10.
Office Action and Formal Examination dated Sep. 2, 2015, received in Columbian application No. 15168109 (K5000), pp. 9-13—English Translation of same, pp. 1-8.
Bianco et al., *Architecting Service-Oriented Systems*, CMU/SEI-2011-TN-008, Aug. 2011, 46 pages, Software Engineer Institute, Carnegie Mellon University, Hanscom AFB, Massachusetts.
B. Braun, B. Braun SpaceStation MRI, Automated Infusion System, brochure, 1 pg., B. Braun Meslungen AG.
B. Braun, Dialog+: Dialog with the future, brochure, Oct. 2008, 1-14, Edition Oct. 2008, B. Braun Avitum AG.
B. Braun, Integrated Glucose Control, brochure, 1-11, B. Braun Melsungen AG.
B. Braun, Outlook ES Safety Infusion System, 2008, 16 pgs., B. Braun Medical, Inc.
B. Braun, Perfusor Space PCA and Accessories: Instructions for Use, manual, Nov. 2010, 1-46, B. Braun Melsungen AG.
B. Braun, Space System Technical Data, brochure, 7 pgs., B. Braun Meslungen AG.
B. Braun, SpaceControl for Automated Glucose Control: Instructions for use, manual, Dec. 2010, 1-43, B. Braun Melsungen AG.
B. Braun, SpaceStation and SpaceCom: Instructions for Use, manual, 1-39, B. Braun Melsungen AG.
B. Braun, The Whole Hospital in the Palm of Your Hand, Automated Infusion Systems, brochure, 1-24, B. Braun Melsungen AG.
Butterfield, Alaris SE Pump, Monitoring and Detection of IV Line Occlusions, 2010, 4 pgs., CareFusion Corporation.
Carayon et al., Observing Nurse Interaction with Infusion Pump Technologies, Advances in Patient Safety: vol. 2—Observing Medication Administration, 349-364.
Cardinal Health, Alaris DS Docking Station: Technical Service Manual, manual, 2007, 1-31, Issue 2, Cardinal Health, Inc.
Cardinal Health, Alaris Gateway Workstation: Technical Service Manual, manual, 2008, 1-67, Issue 4, Cardinal Health, Inc.
Cardinal Health, Alaris GP Volumetric Pump: Technical Service Manual, manual, 2008, 1-84, Issue 3, Cardinal Health, Inc.
Care Everywhere, Gateway User Manual: V1.0.13 W/CQI 1.6: for use with the Sigma Spectrum Pump: Care Everywhere Document No. CE-100-003-IFU, manual, 1-55, CareEverywhere LLC, 9 Tech Circle, Natick, MA, USA.
Carefusion, Alaris SE Pump: Models 7100/7130 and 7200/7230, Rev2.X—User Manual, manual, Apr. 2011, pp. i-126, CareFusion Corporation, San Diego, CA, United States.
Carefusion, Alaris System Direction for Use—with Alaris PC unit, Model 8015, Dec. 2011, 1360, CareFusion Corporation, San Diego, CA, United States.
Carefusion, Enhance your skills, methodology and safety performance: Guardrails CQI Reporter Software, 2010, 1-2.
Carefusion, Infusion Products, catalog, 2011, 1-16, CareFusion Corporation, San Diego, CA, United States.
Charter Kontron, Envoy: The Standard for Bedside Patient Monitoring, catalog, England.
*Communication pursuant to Article 94(3) EPC* dated May 27, 2015, from the European Patent Office for application 11 820 830.5 (I97EP), 1-4.
Communication of the Substantive Examination Result dated Oct. 29, 2015, from the Mexican Institute of Industrial Property for application MX/a/2014/014267 (K66MX), 1-3.
Corsaro et al., Quality of Service in Publish/Subscribe Middleware, Apr. 26, 2006, 1-22, SELEX-SI—Roma.
FDA, Medical Devices: SEDASYS Computer-Assisted Personalized Sedation System—P080009, Recently-Approved Devices, Mar. 24, 2013, 2 pgs., U.S. Food and Drug Administration.

(56) References Cited

OTHER PUBLICATIONS

First Examination Report from The Intellectual Property Office of New Zealand for Application 626636 (197NZ), dated Nov. 13, 2014, 2 pgs.
Food and Drug Administration, Envoy Patient Monitor—Device Modification: Special 510(k) for 12 Lead ECG/Resp. Module, Aug. 16, 2001, 1-12.
Further Examination Report from The Intellectual Property Office of New Zealand for Application 626636 (I97NZ), dated Sep. 24, 2015, 2 pgs.
GE FANUC, Controller Solutions: More Choices for Your Applications, GE Fanuc Controller Solutions catalog, 2004, 1-160, GE Fanuc Automation, Inc.
GE Medical Systems Information Technologies, 510(k) Summary, Aug. 28, 2009, 1-6.
Gieras, Innovative Infusion Pump Technologies, Engineering in Medicine & Biology Society, Jun. 15, 2010, pp. 1-53, IEEE Long Island Chapter.
Goldman et al., Advancing the Adoption of Medical Device "Plug-and-Play" Interoperability to Improve Patient Safety and Healthcare Efficiency, a white paper from the MD PnP Program, Sep. 2009, 1-3, MD PnP Program.
Goldman et al., Medical Device "Plug-and-Play" Interoperability Program, 2012, MD PnP Program.
Goldman, ASTM final F-2761, Medical Devices and Medical Systems—Essential safety requirements for equipment comprising the patient-centric integrated clinical environment (ICE)—Part 1: General requirements and conceptual model, 2008, 1-34, ASTM.
Goldman, Gaps in the System: Medical Device Interoperability, NIST, Oct. 18, 2006, 1-46, MD PnP.
Hawk, III, The Role of Color Coding in Medication Error Reduction, Action of the AMA House of Delegates 2004 Annual Meeting: Report of the Council on Scientific Affairs, CSA Report 5-A-04, pp. 1-8.
Hewlett Packard, HP Viridia Model 24/26 Series Anesthesia / Standard: Quick Guide, manual, 1998, 1-29, Hewlett Packard.
Hoenich et al., Research & Technology: The Current Status and Future Directions of Hemodialysis Machine Technology, Hemodialysis Horizons, 38-44, AAMI.
Hofmann, Modeling Medical Devices for Plug-and-Play Interoperability, Master of Engineering thesis, Massachusetts Institute of Technology, Jun. 2007, pp. 1-187, Robert Matthew Hofmann, MMVII.
Infusion Nurses Society, Infusion Nursing Standards of Practice, Journal of Infusion Nursing, Jan./Feb. 2011, pp. S1-S110, vol. 34, No. 1S, Infusion Nurses Society.
Infusion Nurses Society, Policies and Procedures for Infusion Nursing, 2011, 1-162, 4th edition, Infusion Nurses Society, Inc.
International Search Report & Written Opinion dated May 14, 2012, received in International patent application No. PCT/US2011/066588 (197WO), 9 pgs.
International Search Report & Written Opinion dated Aug. 7, 2014, received in International patent application No. PCT/US2013/076851 (K22W0), 19 pgs.
International Search Report & Written Opinion dated Sep. 4, 2014, received in International patent application No. PCT/US2013/077258 (K50W0), 18 pgs.
International Search Report & Written Opinion dated Jul. 14, 2014, received in International patent application No. PCT/US2013/077135 (L52WO), 18 pgs.
International Preliminary Report on Patentability dated Jul. 3, 2014, received in International patent application PCT/US2011/066588 (197WO), 6 pgs.
International Preliminary Report on Patentability dated Jul. 2, 2015, received in International patent application No. PCT/US2013/076851 (K22WO), 13 pgs.
International Preliminary Report on Patentability dated Jul. 2, 2015, received in International patent application No. PCT/US2013/077258 (K50WO), 13 pgs.
International Preliminary Report on Patentability dated Dec. 4, 2014, received in International patent application No. PCT/US2013/042350 (K66WO), 13 pgs.
International Preliminary Report on Patentability dated Jul. 2, 2015, received in International patent application No. PCT/US2013/077135 (L52WO), 13 pgs.
ISO/IEC, Information Technology—Open Systems Interconnection—Basic Reference Model: The Basic Model, Nov. 15, 1994, 1-59, Second edition (Corrected and reprinted Jun. 15, 1996), ISO/IEC, Geneva, Switzerland.
Israelski, The Symbiq (Next-Generation) IV Infusion Pump: A Feature-Filled "Intelligent" Pump Developed with and for the End-User, May 2007, 1-4, Hospira, Inc.
Invitation to Pay Additional Fees and, Where Applicable, Protest Fee dated May 6, 2014, received in International patent application No. PCT/US2013/077135 (L52WO), 6 pgs.
Jetley et al., Safety Requirements based Analysis of Infusion Pump Software, 1-4, US Food and Drug Administration, Silver Spring, MD, United States.
Joshi et al., OMG's Data Distribution Service Standard: The OMG Data Distribution Service (DDS) Standard specifies a mandatory API for data-centric publish-subscribe, Dr. Dobb's: The World of Software Development, Nov. 20, 2006, 1-9.
King et al., Prototyping Closed Loop Physiologic Control with the Medical Device Coordination Framework, 200X, 1-11.
Millard et al., XEP-0060: Publish-Subscribe, Jul. 12, 2010, 1-173, Version 1.13, XMPP Standards Foundation (XSF).
National Patient Safety Agency, Design for Patient Safety: A Guide to the Design of Electronic Infusion Devices, booklet, 2010, pp. 1-96, Edition 1, National Patient Safety Agency, London, USA.
Nemeth et al., Making Information Technology a Team Player in Safety: The Case of Infusion Devices, Advances in Patient Safety: Interface Design for Infusion Devices, pp. 319-330, vol. 1, Feb. 2005.
Notice for Reason for Rejection, dated Oct. 6, 2015, received in Japanese patent application National Publication No. 2014-548986 (197JP), 5 pgs.
Pfiedler Enterprises, A Comprehensive Surgical Checklist: Using Technology to Help Optimize Preparedness, Patient Safety and Performance (A Continuing Education Self-Study Activity), 2011, pp. 1-20, Pfiedler Enterprises.
Prusch et al., IV Interoperability: Smart Pump and BCMA Integration, brochure, Oct. 5, 2010, 1-13, Lancaster General Health.
Rafferty, Proposal for Wireless Transmission of Non-invasive Respiratory Data to the Servo Module of an Opioid Infusion-Pump for Real-Time Patient Safety Feedback Control, Yale School of Medicine (Publication data unknown but assumed to be prior to the filing date.).
Search Report and Written Opinion from the Intellectual Property Office of Singapore for Application 11201403511Y (197SG), dated Feb. 9, 2015, 22 pgs.
Sprunk et al., System Design for Simultaneous Data Acquisition from Patient Monitor and Syringe Pumps in Intensive Care Unit, Dec. 17-19, 2010, 878-882, IEEE EMBS International Conference on Biomedical Engineering and Sciences, Langkawi.
Talbot et al., Making Stretchable Electronics, Technology Review, Aug. 21, 2012, 1-2, Sep./Oct. 2012, MIT.
The 2008 Annual Premier Breakthroughs Conference: Innovation Through Supply Chain, Technology, and Clinical Sessions, Christine Depietto, Supply Synergy, vol. 3, No. 2, Aug. 2008.
Turisco et al., Beyond E-Health Records, CSC World, Winter 2010, 26-29, CSC World.
Turisco et al., Equipped for Efficiency: Improved Nursing Care Through Technology, Dec. 2008, 1-29, California HealthCare Foundation.
Vanderveen, Technology Focus: Using Data to Improve Smart Intravenous Infusion Pumps, Human Factors Horizons, 2010, pp. 57-63, Human Factors Horizons.
Definition—wifi as downloaded on Jul. 23, 2015, 1 pg.
Wikipedia, Publish-Subscribe Pattern, Jul. 31, 2013, 1-5.
Wikipedia, RSS definition, as downloaded on Jul. 21, 2015, p. 1-9.

(56) References Cited

OTHER PUBLICATIONS

Written Opinion from The Intellectual Property Office of Singapore for Application 11201403511Y (197SG), dated Jun. 19, 2015, 11 pgs.
Written Opinion from The Intellectual Property Office of Singapore for Application 11201403511Y (197SG), dated Oct. 13, 2015, 11 pgs.
Invitation to Pay Additional Fees and, Where Applicable, Protest Fee dated Sep. 26, 2013, received in International patent application No. PCT/US2013/042350 (K66WO), 7 pgs.
International Search Report & Written Opinion dated Nov. 7, 2013, received in International patent application No. PCT/US2013/042350 (K66WO), 18 pgs.
Gregorczyk, David, et al., "A Proof of Concept for Medical Device Integration Using Web Services," 9th Annual International Multi-Conference on Systems, Signals and Devices, Mar. 20-23, 2012, 6pgs.
Mauro, Christina, et al., "Standardized Device Services—A Design Pattern for Services Oriented Integration of Medical Devices" Proceedings of the 43rd Hawaii International Conference on System Sciences , Jan. 5-8, 2010, 10 pgs.
Trinugroho, Yohanes Baptista Dafferianto, et al. "A SOA-Based eHealth Service Platform in Smart Home Enviroment" 13th International Conference on e-Health Networking, Applications and Services: Healthcom 2011 :Jun. 13-15, 2011, Columbia, Missouri, USA, 4 pgs.
Invitation to Pay Additional Fees and, Where Applicable, Protest Fee dated May 19, 2014, received in International patent application No. PCT/US2013/077258 (K50WO), 7 pgs.
Invitation to Pay Additional Fees and, Where Applicable, Protest Fee dated May 23, 2014, received in International patent application No. PCT/US2013/076851 (K22WO), 8 pgs.
U.S. Appl. No. 61/297,544, filed Jan. 22, 2010.
U.S. Appl. No. 13/011,543, filed Jan. 21, 2011, US20110313789A1.
U.S. Appl. No. 61/578,674, filed Dec. 21, 2011.
U.S. Appl. No. 13/333,574, filed Dec. 21, 2011, US20120185267A1.
PCT/US11/66588, Dec. 21, 2011, WO2013095459A1.
U.S. Appl. No. 61/578,649, filed Dec. 21, 2011.
U.S. Appl. No. 61/578,658, filed Dec. 21, 2011.
U.S. Appl. No. 61/651,322, filed May 24, 2012.
U.S. Appl. No. 61/679,117, filed Aug. 3, 2012.
U.S. Appl. No. 61/738,447, filed Dec. 18, 2012.
U.S. Appl. No. 13/723,242, filed Dec. 21, 2012, US20130317753A1.
PCT/US12/71112, Dec. 21, 2012, WO2013096713A1.
U.S. Appl. No. 13/723,251, filed Dec. 21, 2012, US20130204188A1.
U.S. Appl. No. 61/740,474, filed Dec. 21, 2012.
PCT/US12/71142, Dec. 21, 2012, WO2013096722A1.
U.S. Appl. No. 13/723,244, filed Dec. 21, 2012, US20130188040A1.
PCT/US12/71490, Dec. 21, 2012, WO2013096909A1.
U.S. Appl. No. 13/724,568, filed Dec. 21, 2012, US20130184676A1.
PCT/US12/71131, Dec. 21, 2012, WO2013096718A1.
U.S. Appl. No. 13/723,253, filed Dec. 21, 2012, US20130191513A1.
U.S. Appl. No. 13/723,238, filed Dec. 21, 2012, US20130182381A1.
U.S. Appl. No. 13/723,239, filed Dec. 21, 2012, US20130297330A1.
U.S. Appl. No. 13/723,235, filed Dec. 21, 2012, US20130197693A1.
U.S. Appl. No. 13/725,790, filed Dec. 21, 2012, US20130177455A1.
U.S. Appl. No. 13/840,339, filed Mar. 15, 2013, US20130336814A1.
PCT/US13/32445, Mar. 15, 2013, WO2013176770A1.
U.S. Appl. No. 13/833,432, filed Mar. 15, 2013, US20130281965A1.
U.S. Appl. No. 13/833,712, filed Mar. 13, 2013, US20130272773A1.
U.S. Appl. No. 13/834,030, filed Mar. 15, 2013, US20130310990A1.
PCT/US13/42350, May 23, 2013, WO/2013/177357A1.
U.S. Appl. No. 13/900,655, filed May 23, 2013, US20130317837A1.
U.S. Appl. No. 29/457,520, filed Jun. 11, 2013, U.S. Pat. No. D735319S.
U.S. Appl. No. 29/457,516, filed Jun. 11, 2013, U.S. Pat. No. D728,779S.
U.S. Appl. No. 29/457,521, filed Jun. 11, 2013.
U.S. Appl. No. 29/457,522, filed Jun. 11, 2013, U.S. Pat. No. D736,370S.
U.S. Appl. No. 61/843,574, filed Jul. 8, 2013.
U.S. Appl. No. 61/860,398, filed Jul. 31, 2013.
U.S. Appl. No. 13/971,258, filed Aug. 20, 2013, US20130339049A1.
U.S. Appl. No. 61/894,801, filed Oct. 23, 2013.
U.S. Appl. No. 29/471,859, filed Nov. 6, 2013, U.S. Pat. No. D745,661S.
U.S. Appl. No. 29/471,856, filed Nov. 6, 2013.
U.S. Appl. No. 29/471,858, filed Nov. 6, 2013.
U.S. Appl. No. 29/471,864, filed Nov. 6, 2013.
U.S. Appl. No. 29/471,861, filed Nov. 6, 2013, U.S. Pat. No. D749,206S.
U.S. Appl. No. 61/900,431, filed Nov. 6, 2013.
U.S. Appl. No. 61/904,123, filed Nov. 14, 2013.
U.S. Appl. No. 14/101,848, filed Dec. 10, 2013, US20140165703A1.
U.S. Appl. No. 29/477,242, filed Dec. 20, 2013.
U.S. Appl. No. 29/477,236, filed Dec. 20, 2013.
U.S. Appl. No. 29/477,237, filed Dec. 20, 2013.
U.S. Appl. No. 29/477,233, filed Dec. 20, 2013.
U.S. Appl. No. 29/477,232, filed Dec. 20, 2013.
U.S. Appl. No. 29/477,231, filed Dec. 20, 2013.
PCT/US13/77135, Dec. 20, 2013, WO/2014/100687A1.
U.S. Appl. No. 14/136,243, filed Dec. 20, 2013, US20140188516A1.
PCT/US13/77270, Dec. 20, 2013, WO/2014/100744A1.
U.S. Appl. No. 14/137,562, filed Dec. 20, 2013, US20140227021A1.
PCT/US13/77077, Dec. 20, 2013, WO/2014/100658A1.
U.S. Appl. No. 14/135,784, filed Dec. 20, 2013, US20140188076A1.
PCT/US13/76886, Dec. 20, 2013, WO/2014/100571A1.
PCT/US13/76851, Dec. 20, 2013, WO2014100557A1.
U.S. Appl. No. 29/477,249, filed Dec. 20, 2013.
U.S. Appl. No. 14/137,421, filed Dec. 20, 2013, US20140180711A1.
PCT/US13/77258, Dec. 20, 2013, WO2014100736A1.
U.S. Appl. No. 14/135,809, filed Dec. 20, 2013, US20140195639A1.
U.S. Appl. No. 61/942,986, filed Feb. 21, 2014.
PCT/US14/29020, Mar. 14, 2014, WO/2014/144557A1.
U.S. Appl. No. 14/213,373, filed Mar. 14, 2014, US20140318639A1.
U.S. Appl. No. 61/953,036, filed Mar. 14, 2014.
U.S. Appl. No. 61/987,742, filed May 2, 2014.
U.S. Appl. No. 61/990,330, filed May 8, 2014.
U.S. Appl. No. 14/341,207, filed Jul. 25, 2014, US20150033823A1.
PCT/US2014/048227, Jul. 25, 2014, WO2015017275A1.
U.S. Appl. No. 14/451,904, filed Aug. 5, 2014, US20140343492A1.
U.S. Appl. No. 62/052,008, filed Sep. 18, 2014.
U.S. Appl. No. 14/491,128, filed Sep. 19, 2014, US20150002667A1.
U.S. Appl. No. 14/491,143, filed Sep. 19, 2014, US20150002668A1.
U.S. Appl. No. 14/491,161, filed Sep. 19, 2014, US20150002677A1.
U.S. Appl. No. 62/086,356, filed Dec. 2, 2014.
U.S. Appl. No. 14/616,079, filed Feb. 6, 2014, US20150154364A1.
U.S. Appl. No. 29/517,101, filed Feb. 10, 2015.
U.S. Appl. No. 29/517,095, filed Feb. 10, 2015.
U.S. Appl. No. 29/517,096, filed Feb. 10, 2015.
U.S. Appl. No. 29/517,097, filed Feb. 10, 2015.
U.S. Appl. No. 29/517,098, filed Feb. 10, 2015.
U.S. Appl. No. 29/517,099, filed Feb. 10, 2015.
U.S. Appl. No. 29/517,100, filed Dec. 10, 2015.
U.S. Appl. No. 14/627,287, filed Feb. 20, 2015, US20150157791A1.
U.S. Appl. No. 14/656,945, filed Mar. 13, 2015, US20150257974A1.
U.S. Appl. No. 14/679,364, filed Apr. 6, 2015, US20150314083A1.
U.S. Appl. No. 62/168,343, filed May 29, 2015.
U.S. Appl. No. 29/531,366, filed Jun. 25, 2015.
U.S. Appl. No. 29/532,660, filed Jul. 9, 2015.
U.S. Appl. No. 14/812,149, filed Jul. 29, 2015, US20150332009A1.
U.S. Appl. No. 29/538,153, filed Sep. 1, 2015.
U.S. Appl. No. 62/212,871, filed Sep. 1, 2015.
U.S. Appl. No. 14/853,300, filed Sep. 14, 2015.
U.S. Appl. No. 14/873,515, filed Oct. 2, 2015.
U.S. Appl. No. 14/931,928, filed Nov. 4, 2015.
U.S. Appl. No. 14/932,291, filed Nov. 4, 2015.
U.S. Appl. No. 14/938,083, filed Nov. 11, 2015.
U.S. Appl. No. 14/938,368, filed Nov. 11, 2015.
U.S. Appl. No. 14/939,586, filed Nov. 12, 2015.
U.S. Appl. No. 14/939,015, filed Nov. 12, 2015.
U.S. Appl. No. 14/956,648, filed Dec. 2, 2015.
U.S. Appl. No. 29/547,405, filed Dec. 3, 2015.

(56) References Cited

OTHER PUBLICATIONS

U.S. Appl. No. 29/547,402, filed Dec. 3, 2015.
U.S. Appl. No. 29/548,225, filed Dec. 11, 2015.
U.S. Appl. No. 29/552,303, filed Jan. 21, 2016.
U.S. Appl. No. 29/552,942, filed Jan. 27, 2016.
U.S. Appl. No. 29/552,943, filed Jan. 27, 2016.
U.S. Appl. No. 29/553,094, filed Jan. 28, 2016.
U.S. Appl. No. 62/288,132, filed Jan. 28, 2016.

* cited by examiner

SYSTEM AND APPARATUS FOR ELECTRONIC PATIENT CARE

CROSS REFERENCE TO RELATED APPLICATIONS

The present application is a Non-Provisional Application which claims priority to and the benefit of the following:

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, both of which are hereby incorporated herein by reference in their entireties.

This application claims priority to and is also a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility, each of which is hereby incorporated herein by reference in its entirety; and PCT Application Serial No. PCT/US11/66588, filed Dec. 21, 2011 and entitled System, Method, and Apparatus for Electronic Patient Care, which is hereby incorporated herein by reference in its entirety.

This application claims priority to and is also a Continuation-in-Part Application of U.S. patent application Ser. No. 13/723,238, filed Dec. 21, 2012 and entitled System, Method, and Apparatus for Clamping, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,238 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application claims priority to and is also a Continuation-in-Part Application of U.S. patent application Ser. No. 13/723,235, filed Dec. 21, 2012 and entitled System, Method, and Apparatus for Dispensing Oral Medications, which claims priority to and benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,235 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application is also a Continuation-In-Part Application of PCT Application Serial No. PCT/US12/71131, filed Dec. 21, 2012 and entitled System, Method, and Apparatus for Dispensing Oral Medications, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71131 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application claims priority to and is also a Continuation-In-Part Application of U.S. patent application Ser. No. 13/724,568, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/724,568 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application claims priority to and is also a Continuation-In-Part Application of U.S. patent application Ser. No. 13/725,790, filed Dec. 21, 2012 and entitled System, Method, and Apparatus for Infusing Fluid, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/725,790 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application is also a Continuation-In-Part Application of PCT Application Serial No. PCT/US12/71490, filed Dec. 21, 2012 and entitled System, Method, and Apparatus for Infusing Fluid, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

PCT Application Serial No. PCT/US12/71490 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-

A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application claims priority to and is also a Continuation-In-Part Application of U.S. patent application Ser. No. 13/723,239, filed Dec. 21, 2012 and entitled System, Method, and Apparatus for Electronic Patient Care, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,239 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part Application of U.S. patent application Ser. No. 13/011,543, filed Jan. 21, 2011 and entitled Electronic Patient Monitoring System, now U.S. Publication No. US-2011-0313789-A1 published Dec. 22, 2011, which claims priority to U.S. Provisional Patent Application Ser. No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, both of which are hereby incorporated herein by reference in their entireties.

This application claims priority to and is also a Continuation-In-Part Application of U.S. patent application Ser. No. 13/723,242, filed Dec. 21, 2012 and entitled System, Method, and Apparatus for Electronic Patient Care, which claims priority to and the benefit of the following:

U.S. Provisional Patent Application Ser. No. 61/651,322, filed May 24, 2012 and entitled System, Method, and Apparatus for Electronic Patient Care, which is hereby incorporated herein by reference in its entirety.

This application claims priority to and is also a Continuation-In-Part Application of U.S. patent application Ser. No. 13/723,244, filed Dec. 21, 2012 and entitled System, Method, and Apparatus for Monitoring, Regulating, or Controlling Fluid Flow, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,244 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application claims priority to and is also a Continuation-In-Part Application of PCT Application Serial No. PCT/US12/71142, filed Dec. 21, 2012 and entitled System, Method, and Apparatus for Monitoring, Regulating, or Controlling Fluid Flow, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71142 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S.

Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application claims priority to and is also a Continuation-In-Part Application of U.S. patent application Ser. No. 13/723,251, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,251 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application is also a Continuation-In-Part Application of PCT Application Serial No. PCT/US12/71112, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71112 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application claims priority to and is also a Continuation-In-Part Application of U.S. patent application Ser. No. 13/723,253, filed Dec. 21, 2012 and entitled System, Method, and Apparatus for Electronic Patient Care, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,253 claims priority to and is a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, each of which are hereby incorporated herein by reference in their entireties.

This application may also be related to one or more of the following U.S. patent applications filed on even date herewith, all of which are hereby incorporated herein by reference in their entireties:

Nonprovisional application Ser. No. 13/840,339, entitled Apparatus for Infusing Fluid, filed on Mar. 15, 2013, now U.S. Pat. No. 9,675,756 issued on Jun. 13, 2017;

PCT Application Serial No. PCT/US13/32445, entitled Apparatus for Infusing Fluid, filed Mar. 15, 2013, Publication No. WO 2013/176770, published on Nov. 28, 2013;

Nonprovisional application Ser. No. 13/833,432, entitled Syringe Pump and Related Method, filed on Mar. 15, 2013, now U.S. Pat. No. 9,744,300 issued on Aug. 29, 2017;

Nonprovisional application Ser. No. 13/833,712, entitled System, Method, and Apparatus for Clamping, filed on Mar. 15, 2013, now U.S. Pat. No. 9,488,200 issued on Nov. 8, 2016; and Nonprovisional application Ser. No. 13/834,030, entitled System, Method, and Apparatus for Monitoring, Regulating, or Controlling Fluid Flow, filed on Mar. 15, 2013, now U.S. Pat. No. 9,372,486 issued on Jun. 21, 2016.

BACKGROUND

Relevant Field

The present disclosure relates to patient care. More particularly, the present disclosure relates to a system and apparatus for electronic patient care.

Description of Related Art

Providing patient care in a hospital generally necessitates the interaction of numerous professionals and caregivers (e.g., doctors, nurses, pharmacists, technicians, nurse practitioners, etc.) and any number of medical devices/systems needed for treatment of a given patient. Despite the existence of systems intended to facilitate the care process, such as those incorporating electronic medical records ("EMR") and computerized provider order entry ("CPOE"), the process of providing comprehensive care to patients including ordering and delivering medical treatments, such as medications, is associated with a number of non-trivial issues.

Despite the existence of systems incorporating electronic medical records ("EMR") and computerized provider order entry ("CPOE"), the process of ordering and delivering medical treatments still has the potential to cause critical information to be miscommunicated, to allow treatment decisions to be made without ready access to complete information, and to delay implementation of treatment orders due to unnecessarily redundant and inefficient procedures.

Medication errors may be responsible for over 300 deaths and may injure over one million people each year in the United States. Hospitals under financial stress may experience an increased incidence of medication errors. Medications associated with the most dangerous errors include insulin, narcotics, heparin and chemotherapy. Sources of error include administering the wrong drug, the wrong concentration of drug, at the wrong rate, or via the wrong route (medications can be administered orally, intravenously, intramuscularly, subcutaneously, rectally, topically to the skin, via the eye or ear, intrathecally, intraperitoneally or even intravesically). Even with proper orders and proper labeling, medications still can be administered improperly because of illegible handwriting, miscommunication of orders, and mispronunciation of drugs having similar names. The trend toward the use of electronic medical records (EMR) and bar coding systems for medications has been shown to reduce the incidence of medication errors. EMR systems, for example, can facilitate computerized provider order entry (CPOE) and flag orders for drugs that do not match a patient's characteristics such as diagnosis, allergies, weight or age. However, these systems have not been widely adopted and their implementation can result in significant delays and inefficiencies in ordering, preparing and administering medications.

It has been estimated that medication infusion devices are involved in up to one third of all medication errors that result in significant harm. The wrong drug may be hung, incorrect parameters (e.g. drug concentration or rate of infusion) may be entered, or existing infusion parameters may be improperly changed. Of infusion pump-related deaths, nearly half may be due to user error and most of these may be due to errors in programming the infusion device.

An effective monitoring system should monitor and intercede at any phase of the medication ordering and administration process to help minimize any of a number of adverse events that could result from the treatment. The medication treatment process conceptually can be separated into three phases: a prescription phase, a medication preparation phase, and an administration phase. Errors can occur when a prescription is written or entered, when a drug is retrieved for use or mixed in solution, or when it is administered to the patient. It would be particularly desirable for a monitoring system to not significantly impair the efficiency with which medications are ordered, prepared or administered, and preferably to actually reduce the time required to perform those activities by collecting, organizing and presenting relevant information for analysis.

SUMMARY

In an embodiment of the present disclosure, a system for electronic patient care includes a network, a facility gateway, a device gateway application and a medical device. The facility gateway is configured to provide a publish-subscribe service for an application. The device gateway application is configured for execution by the facility gateway. The device gateway is configured to communicate via the network by providing a web service. The medical device is in operative communication with the network. The medical device is configured to communicate with the device gateway using the web service.

The system may further includes a publish-subscribe engine configured to provide the publish-subscribe service. The network may be a TCP/IP-based network. The device gateway application may be a web server of the web service and the medical device is a client of the web service. The device gateway application is configured to register a topic using the publish-subscribe service. The system may include an integration API configured for execution by the facility gateway. The integration API is configured to subscribe to the topic and communicate an event received by the subscription to the topic to at least one external server.

The topic may be one or more of a reportable biomed events topic and/or a reportable clinical events topic. The topic may be a reportable biomed event topic and the device gateway may reformat a medical device event received via the web service into a reportable biomed event receivable by a subscriber to the topic via the publish-subscribe engine. The medical device may communicate the medical device event via the network using the web service. The topic may be a reportable clinical event topic and the device gateway may reformat a medical device event received via the web service into a reportable clinical event receivable by a subscriber to the topic via the publish-subscribe engine. The medical device may communicate the medical device event via the network using the web service The topic may correspond to at least one class of pump events, such as: at least one of an infusion event regarding an alarm, alert or notification, an infusion event regarding infusing, an infusion event regarding programming, a device event regarding communication, a device event regarding an access request, a device event regarding configuration updates, a device event regarding logging, and/or a device event regarding power consumption.

The system may further include a continuous quality improvement listener configured for execution by the facility gateway. The continuous quality improvement listener may subscribe to a reportable biomed event topic and to a reportable clinical even topic. The continuous quality improvement may be configured to communicate a reportable biomed event received by the subscription to the reportable biomed event topic to an external database. The continuous quality improvement may be configured to communicate a reportable clinical event received by the subscription to the reportable clinical event topic to an external database.

The external database may record at least one of the reportable biomed event and the reportable clinical event.

The system may include a device manager executable on the facility gateway. The device manager may be configured to maintain a list of medical devices including the medical device. The list of the medical devices may include a list of serial numbers corresponding to the list of medical devices.

The system may include a monitoring client in operative communication with the medical device through the network to receive status information therefrom.

In another embodiment of the present disclosure, a medical device includes a network, a processor, a transceiver, and a device gateway communication manager. The transceiver is in operative communication with the processor and is configured to communicate via the network. The device gateway communication manager is executable on the processor and is configured to operatively communicate via the transceiver. The device gateway communication manager may be configured to communicate a device event using a web method over the network. The device may be configured to send data to a monitoring device via the network.

The network may be a WiFi network and the transceiver may be a WiFi transceiver. In some embodiments, only the device is configured to initiate communication using the web method.

In yet another embodiment of the present disclosure, a system for electronic patient care includes a network, a facility gateway, a device gateway application, a device application, and a medical device. The facility gateway may be configured to provide a publish-subscribe service. The device gateway application may be configured for execution by the facility gateway. The device gateway may be configured to communicate via the network by providing a web service. The device gateway may publish a medical device event topic. The device application is configured for execution on the facility gateway and is configured to subscribe to the medical device event topic. The device application may publish a CQI-message topic. The device application may be configured to receive an event from the subscription to the medical device event topic and publish the event as a CQI message through the CQI-message topic. The medical device is in operative communication with the network. The medical device is configured to communicate with the device gateway using the web service and to generate the event using a web method of the web service.

The device gateway may subscribe to the CQI-message topic to receive the CQI-message. The system may further include a CQI listener configured for execution by the facility gateway. The CQI listener may be subscribed to the CQI-message topic to receive the CQI message. The CQI listener may communicate the CQI-message to an external database. The CQI message may be a reportable biomed event and/or a reportable clinical event.

The system may include a monitoring client configured to operatively communicate with the medical device. The monitoring client may communicate with the medical device by subscribing to the CQI-message topic.

BRIEF DESCRIPTION OF THE DRAWINGS

These and other aspects will become more apparent from the following detailed description of the various embodiments of the present disclosure with reference to the drawings wherein.

DETAILED DESCRIPTION

Figure 1:
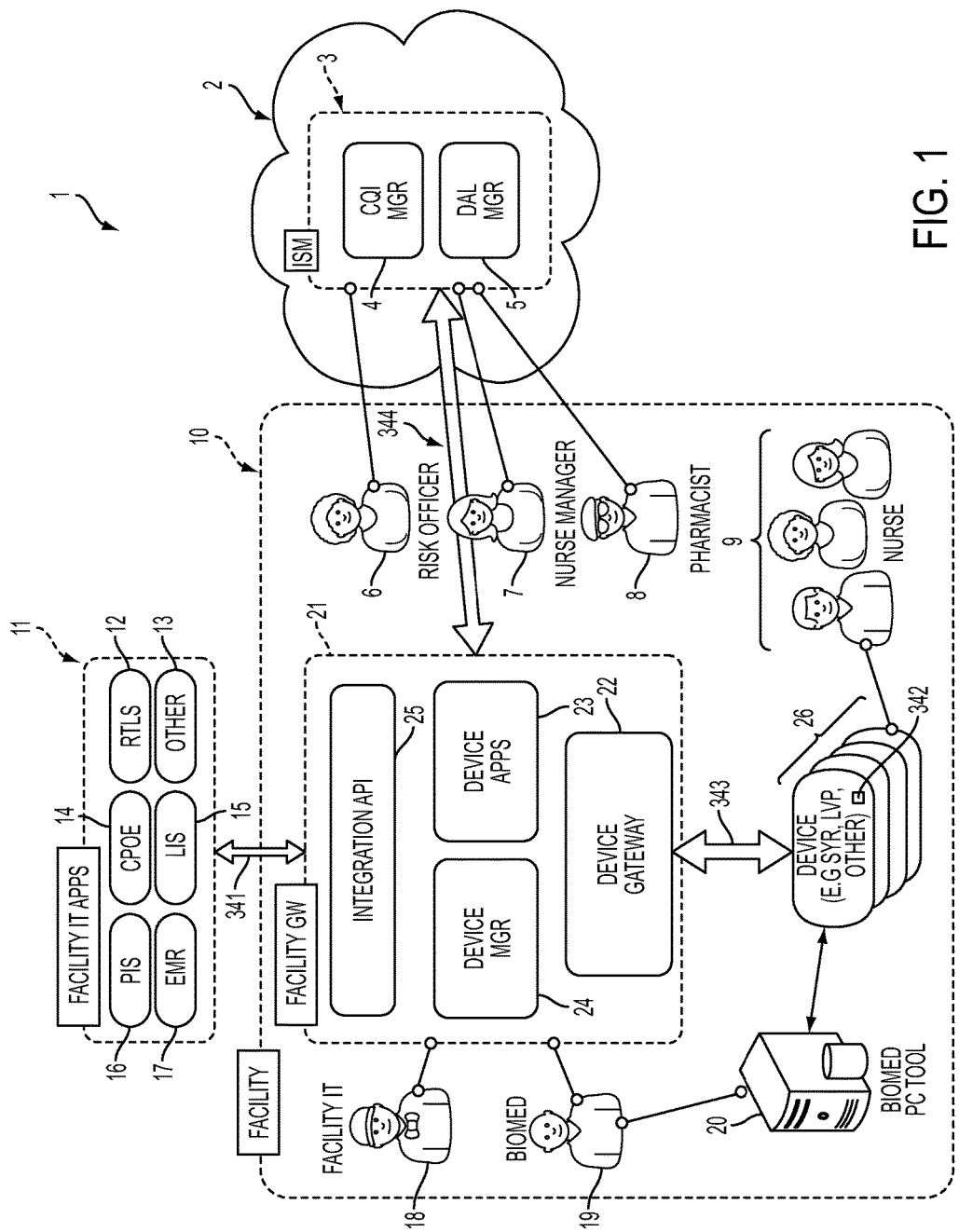
FIG. 1 shows a block diagram of a system for electronic patient care in accordance with an embodiment of the present disclosure.

FIG. 1 shows a block diagram of a system 1 for electronic patient care in accordance with an embodiment of the present disclosure. System 1 includes facility IT applications/services 11, a facility 10, and a cloud services 2.

The facility 10 may be a hospital, a clinic, a medical facility, an outpatient care center, an urgent care center, or a combination or grouping thereof. The facility 10 may include a facility gateway 21 such that various medical devices 26 can communicate with the facility IT applications/services 11 and/or with the cloud services 2. The facility 10 includes various medical devices 26 operated and used by nurses 9 on patients that are in the care of the facility 10. The medical devices 26 may be infusion pumps, peristaltic pumps, syringe pumps, physiological parameter monitoring devices, other patient-care devices, or some combination thereof.

The facility gateway 21 may be hosted, may be in the cloud, may be maintained for the facility 10 by a service provider, may be controlled, maintained or serviced by a combination of service providers and/or facility IT 18 personnel, and/or may be implemented in a virtual or physical environment. In some embodiments, the facility gateway 21 may be implemented in an appliance in a patient's home. The facility gateway 21 may be used by a hospital, a nursing group, an integrated delivery network ("IDN"), an integrated services group or clinic, a group of clinics, a central clinic, or other healthcare facility or infrastructure.

A biomed pc tool 20 may be used by a biomed technician 19 to update the software of the devices 26. The biomed pc tool 20 may be a Browser-based tool for Biomed users 19 to monitor the health of their medical devices 26, view log files, track maintenance activities, and manage the installation of software/firmware. The biomed technician 19 may be a hospital employee (or contract service) who installs, upgrades, and services medical devices 26 (including infusion pumps) to ensure they are in proper working order. The biomed PC tool 20 may interface into the devices 26 via a physical data connection, such as a USB connection or serial cable connection so that the biomed technician 19 may perform these services. The biomed technician 19 may also use the device manager 24 to update the devices 26 wirelessly.

The devices 26 communicate with the facility IT applications/services 11 (via a communications link 343) and/or with the cloud services 2 (via the communications link 344) via the facility gateway 21. The communications links 343 and 344 may use WiFi, Ethernet, TCP/IP, WiMax, fiber optic cables, or any other known communication technology.

The devices 26 communicate with the facility gateway 21 by establishing communications (e.g., via registering) with the device gateway 22. The facility gateway 21 may be a computer, a virtual machine, a hardware device, a software device, a hosted device, software in execution, the like, or some combination thereof. The device gateway 22 may be software executable by the facility gateway 21. The devices 26 may communicate with the device gateway 22 using web services. In some specific embodiments, only the medical devices 26 initiate communication with the device gateway 22 (and thus the facility gateway 21). The device gateway 22 may include a message routing engine that supports both publish/subscribe and point-to-point routing mechanisms. The device gateway 22 may also provide name resolution and capability registry capabilities. Object-Relational Mapping may be used by the device gateway 22 for small-scale object persistence (e.g., using an object-relational mapping (ORM) engine). Additionally or alternatively, the device manager 24 can provide name resolution and/or registry capabilities.

In some embodiments of the present disclosure, a device of the devices 26 is a monitoring client, such as a tablet computer, a tablet device, a PDA, a smart phone, a laptop computer, or a touchscreen-based computer. A monitoring client of the devices 26 may have a monitoring client app within the device apps 23 which allows a caregiver to communicate with other devices of the devices 26. The monitoring client may be used to receive status information from a medical device of the devices 26, receive CQI-messages from a medical device of the devices 26, receive RBEs or RCEs from a medical device of the devices 26, to program a medical device of the devices 26, or otherwise communicate with a medical device of the devices 26.

The communication links 343 between the devices 26 and the facility gateway 21 may use WiFi, Ethernet, TCP/IP, WiMax, fiber optic cables, or any other known communication technology. In some embodiments of the present disclosure, the devices 26 communicate with the facility gateway 21 through a cellular connection (e.g., the communications link 343 includes a cellular connection). For example, one or more of the devices 26 may be a located within a patient's home, within a clinic, within a field facility (e.g., a tent facility), emergency location, other location, or some combination thereof.

The device gateway 22 may provide: (1) component registry and license management (e.g., using the device manager 24); (2) an installation repository for receiving, maintaining and tracking new versions of installable components, such as device firmware/software, drug administration libraries, enterprise application software, and infrastructure software (e.g. operating system releases, application servers, database management system ("DBMS")); and/or (3) message routing capabilities, such as distributing messages, both among applications within the facility gateway 21 and with external subsystems (e.g. the cloud services 2).

Deployment environments where medical devices 26 maintain active network connections to the device gateway 22 are called connected environments and may, as previously mentioned, be achieved using wireless networks (IEEE 802.11b/g/n). Also as previously mentioned, in other embodiments, network connectivity may be achieved through other technologies, like cellular.

Environments where devices do not maintain wireless connections are called standard environments, despite the fact that enterprise application components and external subsystems may still be connected. In this specific embodiment, the device gateway 22 still performs all three roles for enterprise application components and external subsystems, while, message exchange involving the devices 26 may use the biomed technician 19 (e.g., using the biomed PC tool 26) to store the messages into an external media device (e.g. memory sticks).

Event subscribers, such as the device applications 23, may refine the event stream and republish higher-level events back to the device gateway 22. Reportable biomed events ("RBE"), described below, will be among the events republished by these applications. The RBEs may be reported as CQI messages to the cloud services 2. In some embodiments, an application running on the facility gateway 21 is a Biomed Server that subscribes to RBEs and stores them in a local database within the facility gateway 21.

Biomed technicians 19 may use their browser to access the device manager 19 and request device status reports of a device of the devices 26. The UI of the device manager 24 may command the biomed server to access the database and generate HTML/JS pages for browser display to the biomed technician 19.

In some embodiments, before a new device of the medical devices 26 is authorized for use with the device gateway 22, the biomed technician 19 must register the new device using its serial number. This may be validated using asymmetric key (public/private key pairs) encryption, and may be performed as part of the manufacturing process. Once a device of the medical devices is registered with the device gateway 22, the biomed technician 19 configures its wireless protocol and encryption settings. Once a medical device of the medical devices 26 is registered with the device gateway 22, it reports its initial configuration, including model, options, and hardware, firmware and device control software version for storage within the device gateway 22 and/or within the device manager 24. Similarly, when a device is removed from the list of authorized devices of the device gateway 22, the biomed technician 19 can unregister it.

Each of the medical devices 26 may run a self-test on startup, and publish an event the device gateway 22 containing the results. In addition, because the medical devices 26 may routinely run for a long time interval between restarts, the medical devices 26 may automatically schedule and run certain self-tests at times which do not interfere with patient safety and/or treatment.

The facility gateway 21 includes device apps 23 which may communicate data using publish-subscribe data connections (described below). Each device app of the devices apps 23 may be for a particular type and/or model of device of the devices 26. These applications provide software intelligence to medical devices, by receiving, filtering and analyzing raw events, and retransmitting higher-level interpretations. Each type of medical device (of the medical devices 26) will have a corresponding device application (of the device applications).

The facility gateway 21 also includes a device manager 24 for controlling, managing, or monitoring the devices 26. For example, the device manager 24 may be used to update and/or download configuration files into a device of the devices 26. As previously mentioned, the biomed technician 19 may control the updating of software, firmware, or configuration files of the devices 26. The device manager 24 may provide a Browser-based tool for IT managers and/or technicians 18 to monitor the health of the hardware, software and network resources used to support delivery of patient care. That is, the facility gateway 21 may be managed by a facility IT employee/contractor 18.

When a new dose administration library ("DAL") version is released, a secure messaging link may send the DAL file from the DAL manager 5 to the device gateway 22 to notify the Biomed technician 19 of its availability. This notification specifies the device type, location of the DAL, documentation, release notes URL, checksum, and installation dependencies. In some embodiments of the present disclosure, the device manager 24 has access to the new DAL file, receives the DAL file from the device gateway 22, receives the DAL file directly from the DAL manager 5, and/or controls the updating of the medical devices 22 using the DAL file.

In a specific embodiment, the Biomed technician 19 uses the release notes URL (e.g., via a webpage of the device manager 24 and/or via the biomed pc tool 20) to access information about the upgrade, and uses the installer URL and checksum to download and validate the DAL file and save it in the device gateway's 22 repository. Next, the biomed technician 19 selects one or more of the medical devices 22 to copy the new DAL file to which are notified (e.g., via the device gateway 22) that a new DAL file is available for them. On the next medical device restart (of the medical devices 26 that were selected to be updated), the selected group of medical devices installs the new DAL version (backing it out on error) and notifies the device gateway 22 and/or the device manager 24 of the outcome. Any of the procedures described herein to update the DAL file may be used to update firmware, software, an OS, or other configuration files of a medical device of the medical devices 26.

The facility gateway 21 may also include an integration API 25 that allows the devices 26, the device apps 23, and/or the device manager 24 to communicate with various databases of the facility IT apps 11, such as the Patient Information System 16, the Electronic Medical Records 17, the Computerized Physician Order Entry 14, the Laboratory Information System 15, the Real-Time Location Services 12, and/or other database or services 13. The integration API 25 enables the components within the facility gateway 21 to interoperate with the facility IT applications/services 11. The facility gateway 21 may communicate with the facility IT apps 11 via a communications link 341 that may include a wireless link, a hardwired link, a TCP/IP link, an internet link, a software communications link, a hardware communications link, or other communications technique or technology.

The facility IT apps/services 11 support the administrative functions of the hospital (e.g. admission, discharge, transfer, coding, billing, collections, etc.). The integration API 25 isolates differences in the applications 12-16 of the facility IT apps 11 from the applications 23-24, the device gateway 22, and/or the devices 26. For example, a device of the devices 26 may request from the device gateway 22 programming information (or the programming information may be pushed to the device of the devices 16). The patient ID, the pump ID, the drug, and the rate of flow, may reside in one or more of the facility IT apps 11; the integration API 25 provides a common format for communicating this information to the device 26 regardless of the needs or requirements of the facility IT apps 11. This information may be gathered by the integration API 25 querying various ones of the facility IT apps 11 to obtain the data and provide the data to the device 26 in a standardized format. The integration API 25 may be capable of being used with a variety of facility IT apps 12-17 having different formats, data standards, communication standards, encryption standards, etc., but provides a standard interface with the apps 22-24 and/or the devices 26.

The integration API 25 facilitates auto-programming of one or more of the devices 26. The prescription may be sent from one of the servers of the facility IT applications 14. The integration API 25 may receive the prescription to reformat it and send it to the device gateway 22. The facility gateway 21 may include a clinical server which writes the prescription event to a persistent cache. The clinical server may start an auto-programming workflow. This workflow may identify a medical device of the medical devices 26 corresponding to the target patient and send a command message to the respective device of the medical devices 26 to load the prescription. The respective medical device of the medical devices 26 will acknowledge receipt of the prescription and display a notification on the display. The clinician may locate the medication bag and may use a barcode reader on the respective medical device of the medical devices 26 to validate the medication and patient. The respective medical device of the medical devices 26 may then confirm that the medication matches the prescription, and the clinician starts infusion delivery. The respective medical device of the medical devices 26 completes the auto-programming workflow by sending a message to the clinical server via the device gateway.

The caregiver uses a UI to verify the programming of a medical device of the devices 26. The clinician locates the medication, and uses the user interface of the respective medical device of the medical devices 26 to either verify the auto-programming parameters of the medical device of the devices 26 and/or manually program the medical device of the medical devices 26.

The PIS 16 is a departmental system used by the pharmacists 8 to receive, review, track and fill orders for prescription medications. The EMR 17 system keeps track of patient medical history in the health care institution (encounters, exams, diagnoses, procedures, etc.). The CPOE 14 is a system used by doctors or nurses 9 to order lab tests, prescription drugs, medical images and other clinical procedures. The LIS 15 is a departmental system used by lab technicians to receive and process orders for clinical samples (e.g. tissue, blood, urine, etc.) The RTLS 12 tracks the location and status of the devices 26. The other 13 may be any other database used for patient care.

The cloud services 2 include a cloud-hosted infusion safety manager 3. The ISM 3 includes a Continuous Quality Improvement ("CQI") manager 4 and a DAL manager 5. The risk officers 6, the nurse managers 7, and the pharmacists 8 may all review the CQI messages retrieved by the CQI manager 4 to facilitate the development of a DAL file via the DAL manager 5. The DAL file may thereafter be downloaded into one or more of the devices 26. The DAL manager 5 may include or is associated with a Drug Error Reduction System ("DERS") editor (e.g., the DERS editor 112 of FIG. 4, described below).

Figure 2:
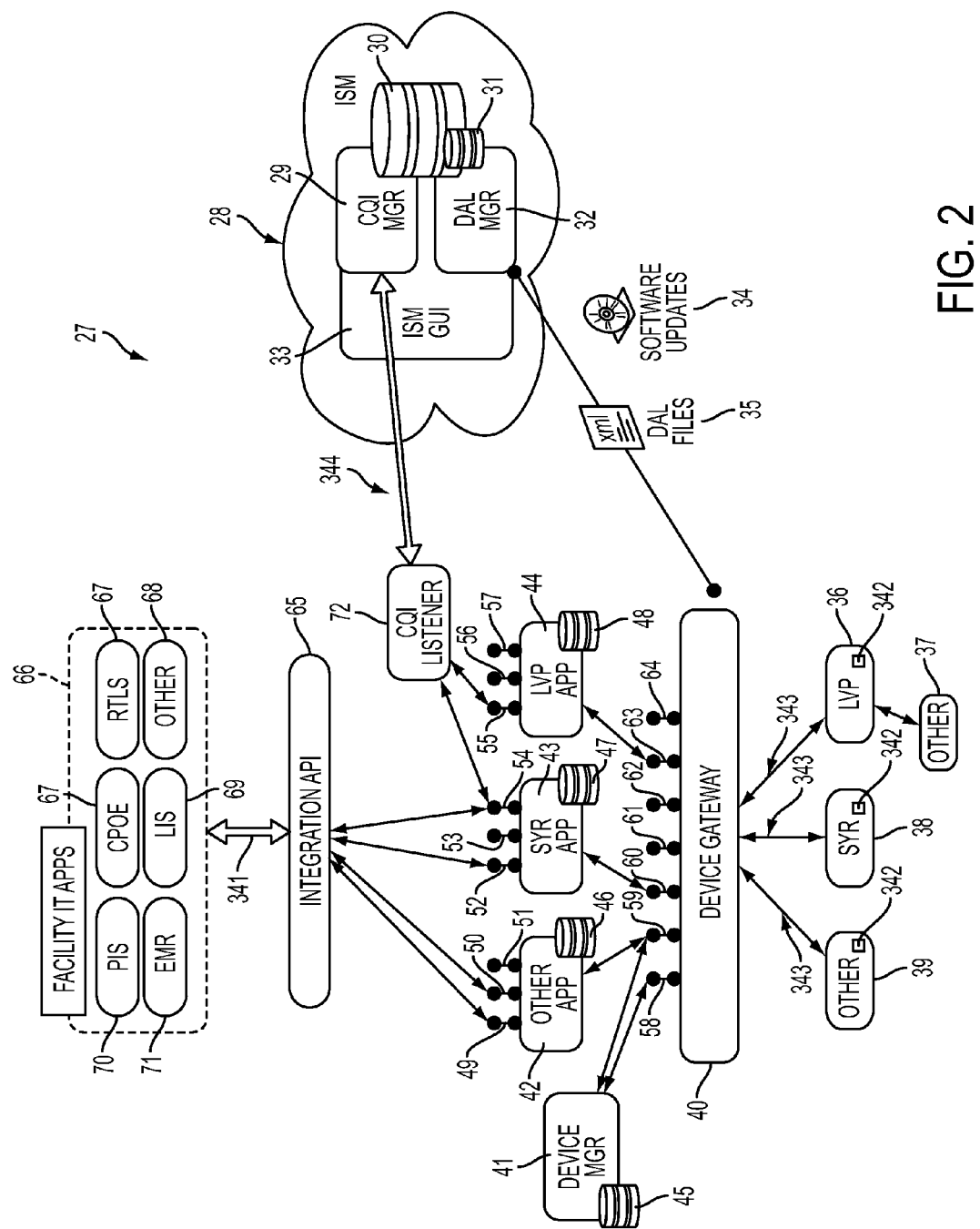
FIG. 2 shows a block diagram of some aspects of the system of FIG. 1 in accordance with an embodiment of the present disclosure.

FIG. 2 shows a block diagram of some aspects of the system of FIG. 1 in accordance with an embodiment of the present disclosure. That is, FIG. 2 shows more details of some aspects of FIG. 1.

The device gateway 40, the device manager 41 and the integration API 65 are all part of the facility gateway 21 of FIG. 1. The large volume app 44, the syringe pump app 54, and the other app 42 are all applications that are part of the device apps 23 of FIG. 1. The device manager 41 including its associated database 45 may be the device manager 24 of FIG. 1.

The Large Volume Pump ("LVP") app 44 is an application for the LVP 36. The syringe app 43 is an application for the syringe pump 38, and the other application 42 is an application for another device 39. The other application 42 and the another device 39 may correspond to any medical device.

The device gateway 40 provides publish-subscribe data connections 58-64. The applications 42, 43, 44 also provide publish-subscribe data connections 49-57. The publish-subscribe messaging pattern provides for the communication between the device gateway 40 and/or the applications 41, 42, 43, 44, 65, 72. However, in additional embodiments, another messaging pattern may be utilized for communications.

The CQI listener 72 may subscribe to various data feeds from the applications 42, 43, 44 to report CQI messages to the CQI manager 29 which may store them in the database 30. The CQI listener 72 may report the raw results of the published connections 49-57 and/or 58-64, and/or may format them.

In some embodiments, the applications 42, 43, 44 reformat the raw events from a respective device of the devices 36-39 (that are received via subscriptions to topics registered by the device gateway 40) into CQI-messages. The applications 42, 43, 44 may register CQI-topics which are subscribed to by the CQI-listener 72. The applications 42, 43, 44 publish the CQI-messages into these CQI-topics which causes the CQI-listener 72 to receive the CQI messages. The CQI-listener 72 transmits the CQI messages to the cloud services 28.

In a specific embodiment, a single GUI interface 33 may be used to view the CQI messages within the database 30 while creating a DAL file 35 for use by the devices 36, 37, 38, and 39. Software updates 34 may also be sent to the device gateway 40 to update the medical devices 36, 37, 38, and 39.

Figure 3:
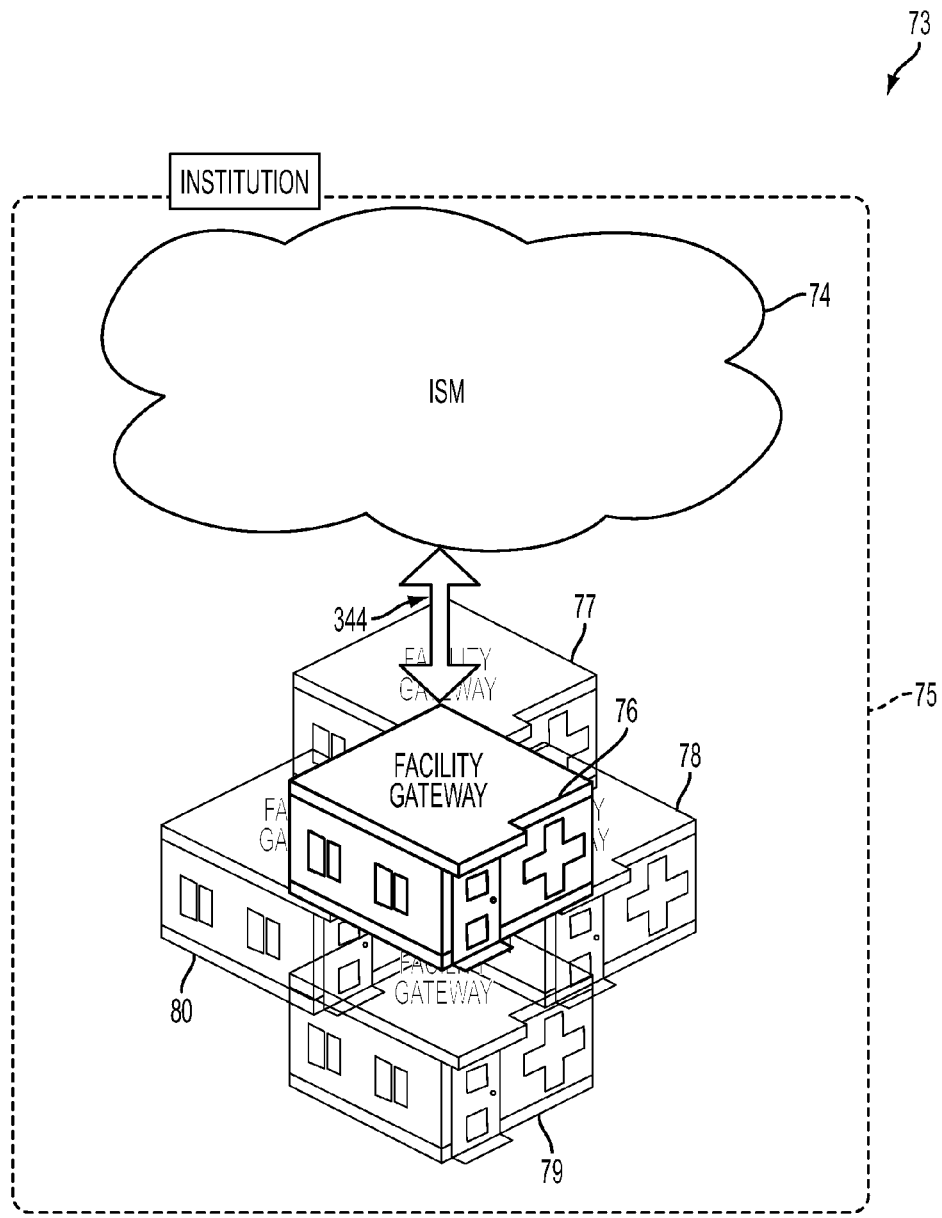
FIG. 3 shows a diagram illustrating the aggregation of several facilities for communication in accordance with an embodiment of the present disclosure.

FIG. 3 shows a diagram 73 illustrating the aggregation of several facilities 76-80 for communication in accordance with an embodiment of the present disclosure. The several facilities 76-80 may each include a facility gateway 21 (see FIG. 2) for communication with cloud services, such as the infusion safety manager 74. In some embodiments, the several facilities 76-80 are part of a group of facilitates that share a common infusion safety manager 74 that is not accessible by other facilities not within the group of facilities 76-80.

Figure 4:
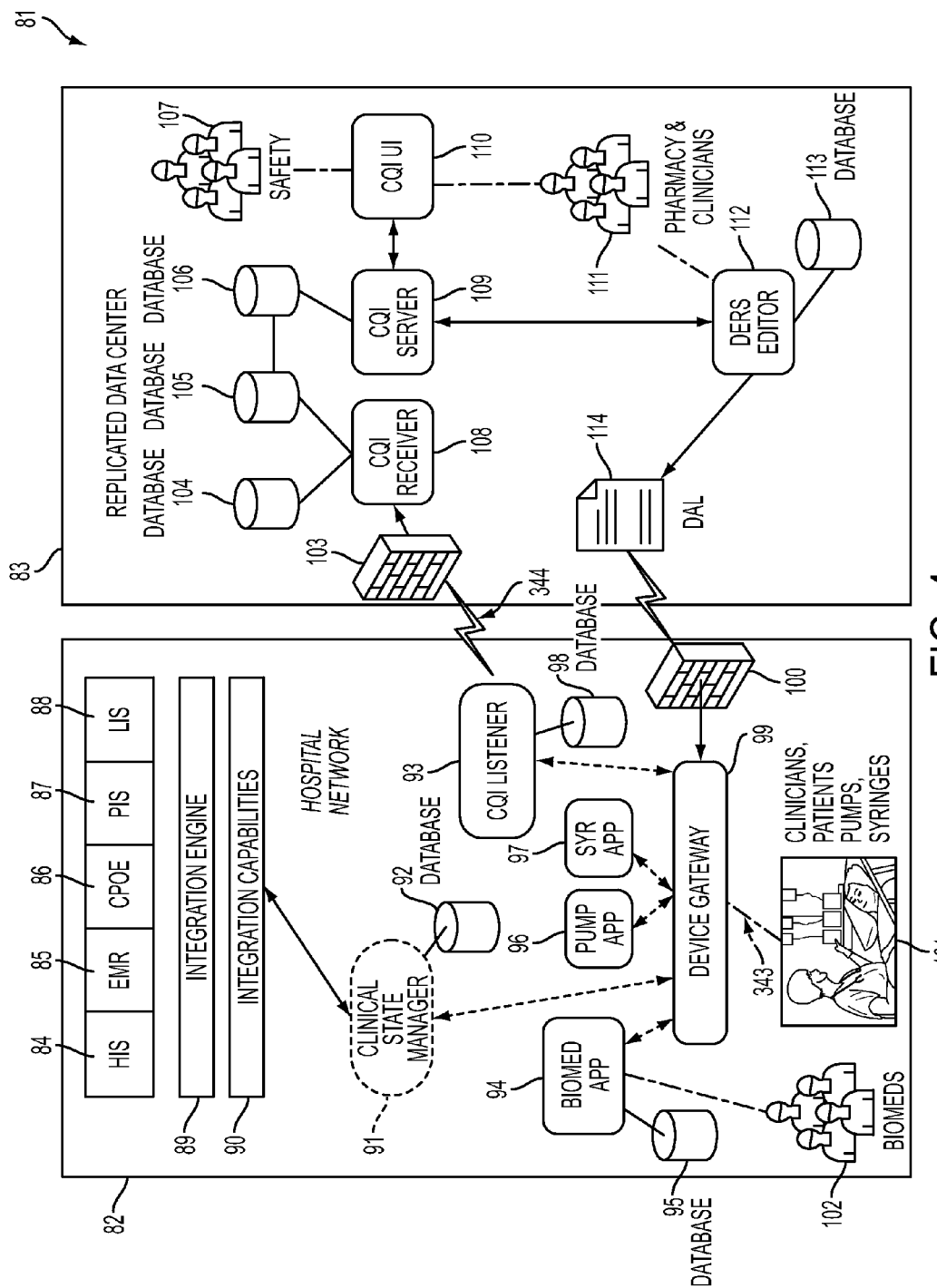
FIG. 4 shows a diagram illustrating a system for electronic patient care in accordance with an embodiment of the present disclosure.

FIG. 4 shows a diagram illustrating a system 81 for electronic patient care in accordance with an embodiment of the present disclosure. The system 81 includes a facility, e.g., a hospital network 82, and cloud services 83.

The hospital network 82 includes a hospital information network 84, an EMR 85, a CPOE 86, a PIS 87, a LIS 88, an integration engine 89, a integration capabilities component 90, a clinical state manager 91, databases 92, 95 and 98, a biomed application 94, a CQI listener 93, a pump application 96, a syringe application 97, a device gateway 99, a firewall 100, and medical devices 101. In some embodiments, systems 84-88 may be external to the hospital network 82. A team of biomed technicians 102 may be available to use the biomed application 94.

The cloud services 83 includes databases 104, 105, 106 and 113, a firewall 103, a CQI receiver 108, a CQI server 109, a CQI UI 110, and a DERS editor 112. Pharmacy and clinicians 111 may interface into the DERS editors 11 and/or the CQI UI 110. Safety staff 107 may interface into the CQI UI 110. The DERS editor 112 and/or the CQI UI 110 may be a browser-based interface.

The HIS 84 supports the administrative functions of the hospital (e.g. admission, discharge, transfer, coding, billing, collections). The EMR 85 keeps track of patient medical history in the health care institution (encounters, exams, diagnoses, procedures, etc.). The CPOE 86 is a system used by doctors to order lab tests, prescription drugs, medical images and other clinical procedures. The PIS 97 is a departmental system used by pharmacists to receive, review, track and fill orders for prescription medications. The LIS 88 is a departmental system used by lab technicians to receive and process orders for clinical samples (e.g. tissue, blood, urine, etc.). The hospital integration engine 89 provides message translation capabilities to enable the information system 84-88 to interoperate with each other and with external systems. Most of these engines map between different dialects of HL7. An Integration Engine may be located on the device gateway 99 to interoperate with the HIS, EMR and PIS, through the hospital integration engine 89. The device gateway 99 provides message routing engine, supporting both publish/subscribe and point-to-point routing mechanisms. The device gateway 99 also provides name resolution and capability registry capabilities.

Various devices 101 are used to treat patients, such as infusion devices that deliver medication, nutrition and hydration in liquid form to patients via intravenous (IV) or subcutaneous routes. A pump application 96 and a syringe application 97 are applications that provide software intelligence to medical devices 101, by receiving, filtering and analyzing raw events, and retransmitting higher-level interpretations. Each type of medical device of the devices 101 may have a corresponding device application, e.g., one of the applications 96-97.

Each infusion device of the devices 101 may be used to control delivery of a specific infusate (hydration, nutrition, blood or medication in liquid form) to a specific patient. Dose adjustments, in the form of loading or bolus doses, or dose titrations may be considered to be separate infusion phases within a parent infusion. A collection of infusions for the same patient as part of the same therapy are considered to be an "Infusion Story" which may be recorded by a CQI server 109.

An infusion may be organized into a setup phase, a programming phase, and a delivery phase. During the setup phase, a clinician verifies the infusate, patient and pump, and connects the tubing from the infusate to the pump and the pump to patient, which may be recorded by the CQI server 109. During the programming phase, the clinician enters the dose parameters into the pump and the pump verifies them using the installed DAL version (which may also be recorded by the CQI server 109). During the delivery phase, the pump delivers the specified volume of infusate at the programmed rate.

Each of the medical devices 101 may detect alarm conditions (i.e. situations where the pump is not infusing), as well as alert and advisory conditions, which may or may not be safety-critical. Each of the medical devices 101 may attempt to establish a secure network connection to the device gateway 99. Each of the medical devices 101 may collect programming, delivery status and exception events for each infusion and provide them to the device gateway 99 so that they may be reported as CQI messages to the CQI receiver 108. Each of the medical devices 101 may communicate these events to the device gateway 99, which routes the data to the CQI receiver 108 (directly or indirectly). If or when, in some embodiments, a medical device of the medical devices 101 cannot establish or maintain a working connection to the device gateway 99, the medical device may save these events in an internal buffer, and permit the biomed technician 102 to copy them to portable media (e.g., a memory stick) with or without the use of the biomed application 94. In some embodiments, these events may be downloaded via the biomed application 94 running on a personal computer that has a USB cable coupled to the medical device.

The biomed app 94 provides a browser-based tool for biomed users 102 to monitor the health of their medical devices 101, view log files, track maintenance activities, and manage the installation of software/firmware. The log files, maintenance logs, and software/firmware installation and upgrade tracking data may be stored in the database 95.

The device gateway 99 may be a beside device that couples to all of the devices 101 associated with a particular patient. In another embodiment, the device gateway 99 is a software application executable on a facility gateway. In yet another embodiment, the device gateway 99 is software executable on a bed-side appliance (e.g., a compact computer). The device gateway 99 may be a message router, a service registry, and/or a pump authorization registry. The device applications 96-97 can register message types and publish messages to the gateway device 99. Any medical device of the medical devices 101, including sensors that may plug into a medical device (see other 37 in FIG. 2) of the medical devices 101 (e.g. respiratory monitor into PCA) can be used to publish data via the gateway device 99. The device applications 96-97 may act as "information refineries." Each of the device applications 96-97 subscribes to messages from a particular type of bedside device of the medical devices 101 via the gateway device 99. Each of the device applications 96-97 can synthesize CQI, clinical, and biomed information from an event stream received from one or more of the medical devices 101 through the device gaeway 99. In some embodiments, each of the device applications 96-97 re-publishes these higher level events to the device gateway 99 or to other subscribers, such as the CQI listener 93.

In some embodiments, some of the CQI messages may be used for auto-documentation, auto-programming and billing functions. In yet some additional embodiments, the CQI messages may be used for auto-documentation from the medical device 101 into the EMR 85 and/or for auto-programming of the medical device 101 from an eMAR system (e.g., part of HIS 84). The CQI messages may include drug safety events and latency information.

The CQI listener 93 subscribes to events related to continuous quality improvement of drug safety and ensures their reliable delivery to the hosted environment. The CQI listener 93 may store the events in the database 98 for periodic transmission to the CQI receiver 108 (through the firewall 103).

The CQI receiver 108, the CQI server 109, and the CQI UI 101 may be provided in a hosted environment 83 (i.e., cloud services). A master-slave database replication (database 105 as master and 106 as slave) may be used in the hosted environment 83 in order to reduce conflicts between user queries and CQI data updates. The CQI server 109 may post-process CQI events into summary (reportable) form prior to storing them in the database 105 in order to reduce response time for top-level queries and presentation requests. The CQI UI 110 may provide a series of standard reports (compliance, limit violations, titration safety, events by stage, and events by priority). The CQI sever 109 may support a query API, to be used by the DERS editor 445 and the CQI UI 110 to drill down to more detailed summaries and into details of particular CQI messages.

The CQI server 109 provides analysis and query services for a user using the CQI UI 110. The CQI server 109 may provide the user of the CQI UI 110 summary totals for CQI messages and update summary tables (on a configurable interval). The purpose of these summary tables is to reduce response time for top-level CQI queries. These summaries may cover the following statistical measures: (1) programming modes used, such as infusions using DERS limits vs. wildcard; (2) soft and hard limit violations; (3) titration safety information, such as titration increase/decrease settings and dose limit violations; (4) reportable clinical events (e.g., RCEs 149 of FIG. 8, described below) by priority level; and/or (5) reportable clinical events (e.g., RCE 149 of FIG. 8, described below) by infusion stage. Each of these summaries may compute subtotals for the following data views: (1) organization name; (2) institution name (e.g., facility name); (3) care area; (4) hour of day; and/or (5) week.

A web service query API may be used to enable the CQI UI 110 and/or the DERS editor 112 to select: (1) summary totals for each data view described above, filtered by the specified selectors; (2) RCE detail by infusion; and/or (3) actual programming, limits and infusion statistics by patient (i.e. infusion stories). In some specific embodiments, the DERS editor 112 and/or any system of the hosted services 83 may be based upon a J2EE-compliant application server. The databases 104, 105, 106, and 113 may use a database management server.

Once the J2EE and database management servers are installed and configured, the following shared database tables may be imported to perform a DERS database 113 initialization: (1) reference tables, such as units of measure, dose modes, etc.; (2) access control tables for administrative users, roles, privileges and permissions; (3) DERS medication list; (4) NDNQI care group list; (5) institution attributes; and/or (6) database tables required by the DERS editor 112. The DERS editor 112 may be used to add or edit organizations, add or edit regions, and/or add or edit access control (each with or without attributes).

In one embodiment, the DERS Editor 112 and/or the DERS database may run in a single application server and database environment for multiple facilities 82. In yet another embodiment, each institution 82 may host is hosted in its own virtual environment (e.g., cloud services 2).

The CQI UI 110 and/or DERS editor 112 may support an HTTP/Javascript interface for producing CQI reports and interactive drill-down operations to users who are running a web browser, in some specific embodiments.

The CQI messages are received by the CQI receiver 108 which stores them in the database 105. If the CQI receiver 108 cannot process all of the incoming CQI messages at a predetermined rate and/or the CQI receiver's 108 buffer is full, the CQI messages are temporarily stored in the database 104, which may be accessed by the CQI receiver 108 for storage within the database 105 when the CQI receiver is unloaded. The database 105 may be replicated by the database 106. The database 106 is user accessible via the CQI server 109 using either the CQI user interface 110 and/or the DERS editor 112.

The CQI databases' 105, 106 records depend on the DERS editor 112. The records include: (1) reference tables, such as units of measure, dose modes, etc.; (2) access control tables for administrative users, roles, privileges and permissions; (3) DERS Medication List; (4) NDNQI care group list; and/or (5) institution attributes.

Since these references are dependent on the DERS editor database's 113 version, consistency is preferable. One option is to share the tables between the databases 113, 105, 106. While this option is convenient, it increases deployment coupling between the two databases 113 and 105, 106. Alternatively, coupling can be reduced by maintaining read-only copies of these tables inside the CQI databases 105, 106, with a procedure to update them whenever they are changed in the DERS Editor 112.

Access control for the CQI databases 105, 106 may be similar in structure but different in content versus the DERS database 113. Some users may be defined for the CQI server 109 but not for the DERS editor 112. Even for those users which appear in both, permissions may differ (e.g. some CQI data is read-only).

Certain database tables (e,g., reportable clinical events and statistical summaries) may be required by the CQI databases 105, 106 and are setup when the CQI databases are 105, 106 created.

The CQI UI 110 and/or the DERS editor 112 may each utilize data from the CQI server 109 (and thus data from the database 106) and data from the DERS editor 112 (and thus with the database 113) to generate a DAL file 114.

The clinical state manager 91 is an intermediary between the device gateway 99 the integration engine 89 which orchestrates asynchronous workflows involving several actors and components.

Pharmacists and select clinicians 111 use the DERS editor 112 to define dose limits for an institution and create a DAL file 114 (which may be in an XML format). The dose limits may be defined using a well-defined, carefully controlled, fully documented process, with controlled release procedures. Dose limits may be specified using the DERS editor 112 of the DAL manager 5. The facility 82 may use common reference models for medications, care areas, dose modes, etc. to facilitate later cross-institutional comparison. The DERS editor 112 may run in the hosted environment 83 such that users access it using a web browser. In some embodiments, no client-side software is required to run the DERS editor 112 except for a sufficient browser. The DERS editor 112 may provide dose limits and defaults that are organized by care area, medication, clinical use and drug concentration. The DERS editor 112 may support a query interface to the CQI server 109 to integrate the search and analysis of CQI insights to improve the next DAL version.

Figure 5:
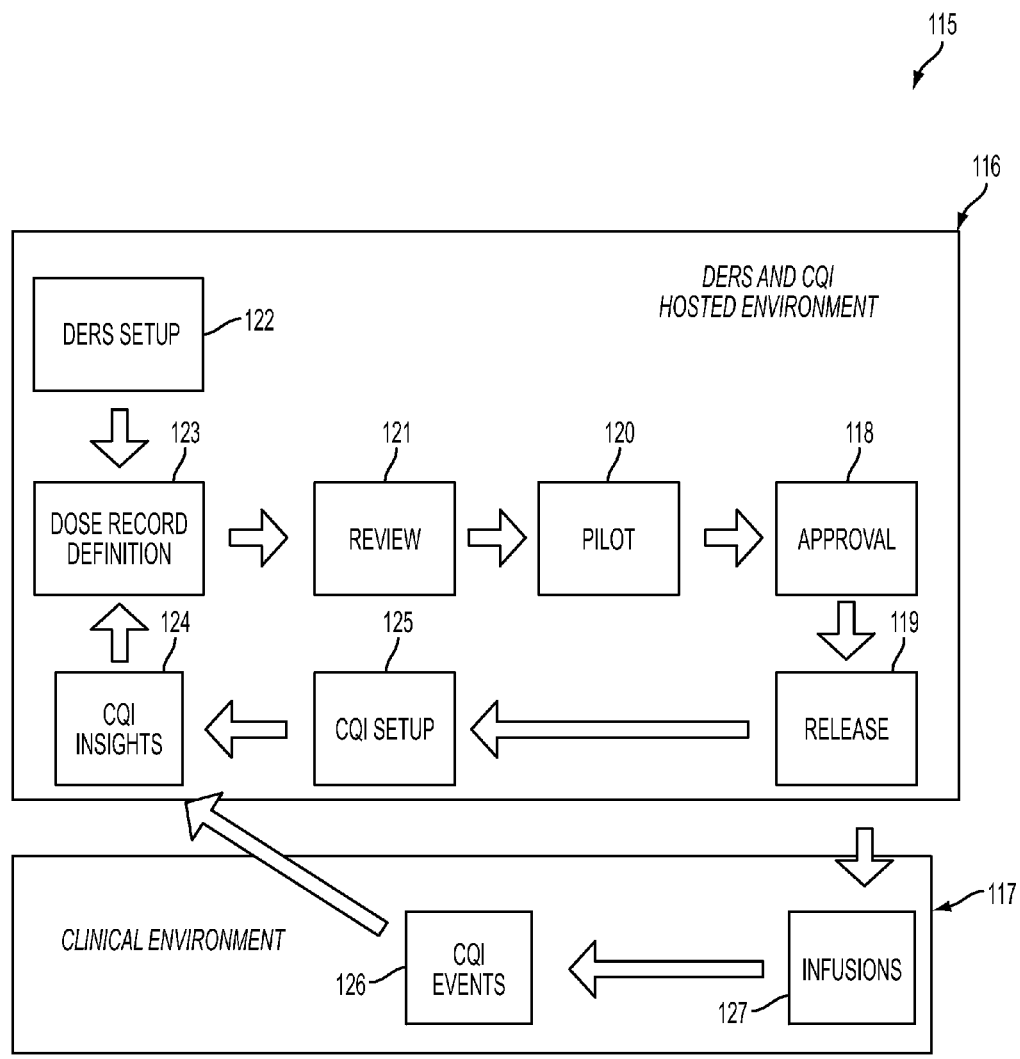
FIG. 5 shows a drug safety method used to generate a dose administration library file in accordance with an embodiment of the present disclosure.

FIG. 5 shows a drug safety method 115 used to generate a DAL file in accordance with an embodiment of the present disclosure. The method 115 may be used with the system 1 of FIG. 1, the system 27 of FIG. 2, the system 81 of FIG. 4, or any other electronic patient care system.

Participants from a pharmacy and clinical care area (e.g., selected users from 6, 7, 8, 9, 18, and 18 of FIG. 1 or 102, 107, and 111 of FIG. 4) may be selected to help generate and define a DAL File 35 (see FIG. 2) that contains safety rules for drug infusions that may consider the type of medication, clinical care area, dose mode (e.g. amount-based, rate-based or weight-based, dose strategy (loading, bolus, ramp), etc.

Method 115 includes acts 116 and 117. Act 116 includes acts 118-125 as subacts and act 117 includes acts 126-127 as subacts. Act 116 generates a DAL file and act 117 monitors the use of the DAL file to update the DAL file 35 (see FIG. 2).

Act 122 sets up a DAL file, e.g., an initial DAL file without field entries or a template DAL file. Act 123 receives modifications to the DAL file in accordance with an entry from one of the selected users (e.g. via the GUI interface 112 of FIG. 4). Act 121 reviews the DAL file, e.g., by running a medical device simulator via the GUI interface 112 of FIG. 4. After review during act 121, a pilot DAL file is (electronically) released in act 120. Act 118 approves the pilot DAL file. However, after the pilot has completed, adjustments may be made to the DAL. Act 118 may be performed via clicking on a "approve" button on a web browser to approve the use of a referenced file (e.g., referenced by version number, creation date, etc.).

In act 119, the DAL file is released and is sent to the medical device in act 127. In Act 125, the CQI server imports reference data (i.e. medications, care areas, dose modes, etc.) from the DAL file. Upon DAL release, a file containing the dose records is released to both the hospital and to the CQI environment. A biomed technician installs the DAL on each infusion device after release in act 119. Act 126 is the medical device sending CQI events to the CQI receiver 108.

During infusions, medical devices generate CQI events (i.e., CQI messages). The CQI messages may include information about when a normal infusion occurs, when an infusion bypasses the DERS checks, when a soft limit is exceeded and overridden, and/or when a soft or hard limit is exceeded and the dose is reprogrammed, among others The CQI events are transmitted to a CQI Server in act 126, which collects and stores them. Safety officers can run reports which summarize these events and provide drill-down capabilities to identify opportunities for procedural improvement in act 124. Similarly, pharmacists and clinicians can query the CQI database to identify opportunities to improve dose records in the next release of the DAL in act 124. That is, in act 124, the CQI messages are analyzed or reviewed. Modifications to the DAL file may be made in act 123 to create a new version of the DAL file.

Figure 6:
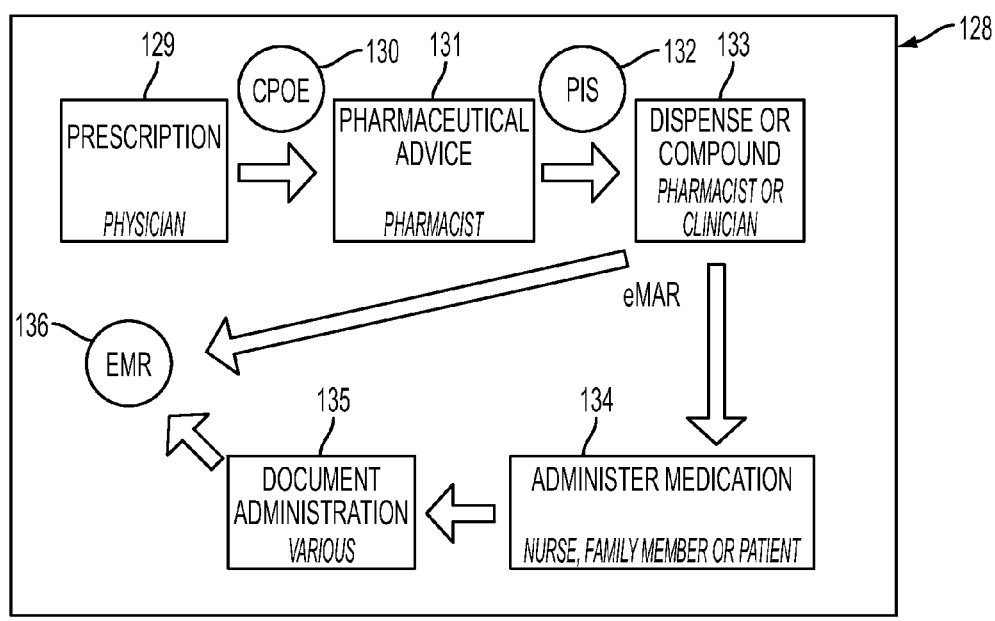
FIG. 6 illustrates a method of infusing a medication in accordance with an embodiment of the present disclosure.

FIG. 6 illustrates a method 128 of infusing a medication in accordance with an embodiment of the present disclosure. The method 128 includes acts 129, 131, 133, 134, and 135. The method 128 may be used with the system 1 of FIG. 1, the system 27 of FIG. 2, the system 81 of FIG. 4, or any other electronic patient care system.

In act 129 a physician writes a prescription electronically. The order is entered into the CPOE 130, which is electronically sent to a pharmacy. In act 131, the pharmacist reviews the order, making assessments for drug interactions and medication supply, and either fills the prescription or modifies the prescription (e.g., in consultation with the physician). Also in act 131, the prescription is perfected and an order is submitted to a PIS 132. In act 133, the prescription is dispensed. This may be done by (including by not limited to): using a pre-prepared compound with the medication already in the desired concentration; the pharmacist compounding the desired dose and concentration in the pharmacy; and/or a clinician (e.g., nurse) compounding the desired dose and concentration at the bedside of the patient.

Next, the dose is administered to the patient in act 134. In an inpatient setting (hospital or nursing home), a clinician typically performs the dose administration. In an ambulatory or home setting, administration may be performed by a clinician, a family member of the patient, or by the patient themselves. Drug safety procedures seek to ensure that the "right patient," "right medication," "right dose," "right time" and "right route" tests are met. This may be achieved in several ways, including by a bedside point-of-care system, by bar coding the patient and medication, and/or by using auto-programming. Documentation of the record is submitted to a record keeping system in act 135. In act 135, documentation is provided to an EMR system to update the patient's chart.

Figure 7:
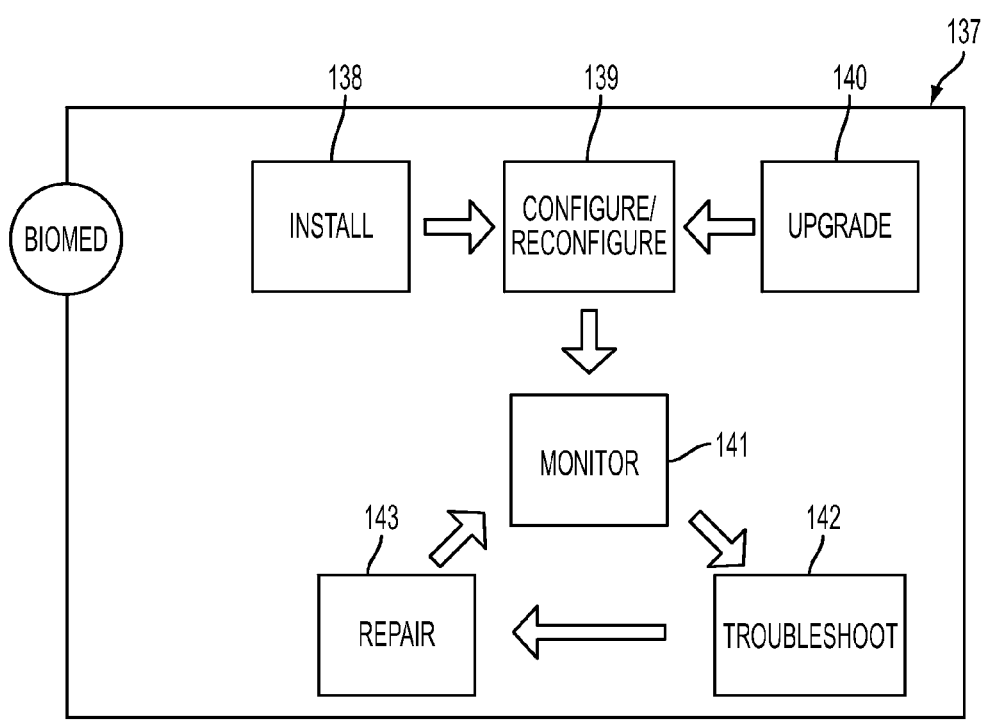
FIG. 7 illustrates a method to update a medical device with software, firmware, and/or a configuration file in accordance with an embodiment of the present disclosure.

FIG. 7 illustrates a method 137 to update a medical device with software, firmware, and/or a configuration file in accordance with an embodiment of the present disclosure. The method 137 includes acts 138-143. The method 137 may be used with the system 1 of FIG. 1, the system 27 of FIG. 2, the system 81 of FIG. 4, or any other electronic patient care system.

In act 138, a biomed technician 19 (see FIG. 1) installs the software, firmware, or configuration files on a medical device (e.g., for the first time) and/or in act 140, the biomed technician upgrades the software, firmware, or configuration files on a medical device. In act 139, the medical device is configured or reconfigured. Acts 138, 139, and/140 may be performed wirelessly or through a physical connection between a biomed tool 20 (see FIG. 1) and the medical device.

A biomed technician 19 can perform act 138 and/or act 140. In act 141 the medical device is monitored (e.g., via CQI messages, etc.) In some embodiments, a biomed technician 19 can copy CQI event files from infusion devices to portable memory sticks for subsequent upload to a CQI server. Act 141 may be used to: identify when devices need to be scheduled for preventative maintenance; identify if the medical device needs to download software, firmware, configuration files or other updates and upgrades; upload device log files; and/or perform other diagnostic and maintenance tasks.

Act 141 monitors the medical device (e.g., wirelessly). Act 142 determines if any issues are identified in the medical device. Issues, such as, the medical device is not operating within predetermined parameters, the medical device is detecting an internal error, and/or the medical device determines its software, firmware, or configuration files are out of date. In act 143, the medical device is repaired in response to the issue identified in the medical device.

Figure 8:
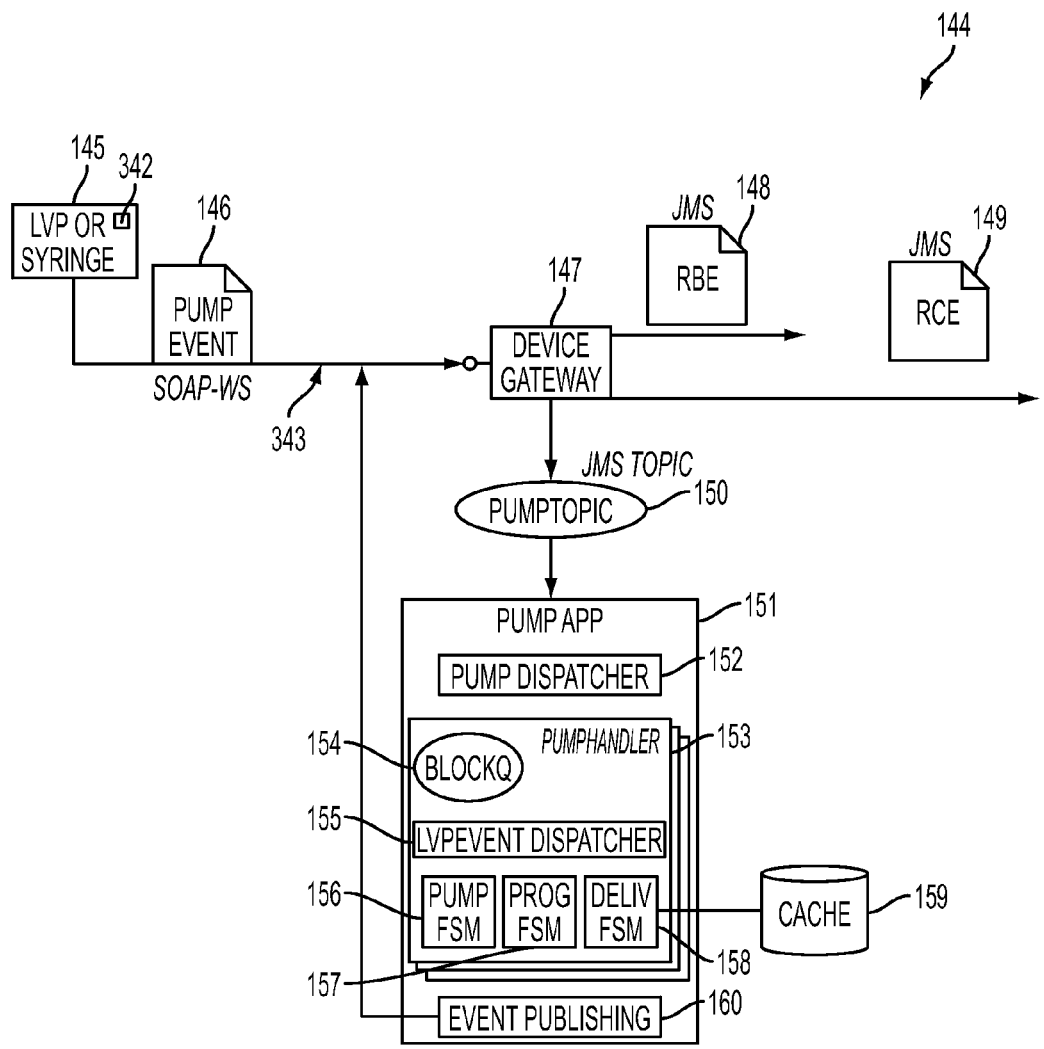
FIG. 8 is a block diagram to illustrate some aspects of a communication between a medical device and a device application in accordance with an embodiment of the present disclosure.

FIG. 8 shows a block diagram 144 to illustrate some aspects of a communication between a medical device 145 (e.g., an infusion pump) and a device application 151 (e.g., a pump application) in accordance with an embodiment of the present disclosure. Although a pump 145 is described herein with reference to FIG. 8, it is contemplated to use any other medical device in place of or with the pump 145 to generate the event 146.

Shown in the block diagram 114 is a medical device 145 (e.g., an infusion pump) that communicates an event 146 (e.g., a pump event) to a device gateway 147. The pump event 146 may be a CQI-message, may be the basis for a CQI-message, or it may be other data, such as raw data, from the medical 145. The pump event 146 may be an operating parameter, a delivery parameter, and/or other operating events. In some specific embodiments, the pump event 146 may use Simple Object Access Protocol ("SOAP") using Web Services ("WS") addressing. In some embodiments, the event 146 is communicated using Representational StateTransfer ("REST") which may use the full HTTP (or HTTPS) protocol.

The event 146 may be an event as shown Table 1 as follows:

TABLE 1

| ID | Pump Event Name |
|---|---|
| 2 | Infusion Events (Alarms, Alerts, Notifications) |
| 2.1 | High priority technical Alarm signaled |
| 2.2 | High priority Operational Alarm signaled |
| 2.3 | Occlusion Alarm signaled |
| 2.4 | Side clamp not installed when loading admin |
| 2.5 | Peristaltic pump not sealed |
| 2.6 | Admin set removed while infusion |
| 2.7 | Under infusion Alarm |
| 2.8 | Air limit reached |
| 2.9 | Air single bubble exceeds allowable |
| 2.1 | Alarm condition cleared by operator |
| 2.11 | Internal Software Error |
| 2.12 | Medium priority Alert signaled |
| 2.13 | Medium priority Alert escalated signaled |
| 2.14 | Operator inactivity during programming |
| 2.15 | Low priority Alert signaled |
| 2.16 | Infusion near end Alert |
| 2.17 | Callback alert signaled |
| 2.18 | Notification signaled |
| 2.19 | Alarm silenced |
| 3 | Infusion Events (infusing) |
| 3.1 | Pump status update |
| 3.2 | Pump switch to Bolus delivery |
| 3.3 | Pump switch to Loading Dose delivery |
| 3.4 | Pump switch to Multirate delivery |
| 3.5 | Pump switch to next Multirate step |
| 3.6 | Pump switch to primary delivery |
| 3.7 | Pump switch to KVO |
| 3.8 | Infusion end awaiting operator input |
| 3.9 | Infusion end revert to primary |
| 3.1 | Infusion end stop infusion |
| 3.11 | Infusion end switch to KVO |
| 4 | Infusion Events (programming) |
| 4.1 | Set programming context as primary |
| 4.2 | Set programming context as secondary |
| 4.3 | Set programming context as Bolus |
| 4.4 | Set programming context as Loading Dose |
| 4.5 | End programming mode |
| 4.6 | Cancel programming |
| 4.7 | Rate set |
| 4.8 | Dose rate set |
| 4.9 | Care Group set |
| 4.1 | Drug Name set via selection |
| 4.11 | Drug Name set via operator override |
| 4.12 | Clinical use set |
| 4.13 | Drug Concentration set |
| 4.14 | Volume to be infused set |
| 4.15 | Time remaining set |
| 4.16 | Pump mode set |
| 4.17 | Patient ID set |
| 4.18 | Patient name set |
| 4.19 | Patient weight set |
| 4.2 | Patient BSA set |

TABLE 1-continued

| ID | Pump Event Name |
|---|---|
| 4.21 | Program Cleared |
| 4.22 | DERS soft limit exceeded |
| 4.23 | DERS soft limit attempted |
| 4.24 | DERS hard limit attempted |
| 4.25 | DERS not used for programming |
| 4.26 | Titrating program |
| 4.27 | Occlusion threshold set |
| 5 | Device Events (Communication) |
| 5.1 | WIFI Comm Status Change |
| 5.2 | Device Gateway Comm Status Change |
| 5.3 | Authentication Comm Status Change |
| 5.4 | GenericDeviceLogMessage |
| 5.5 | Infusion Program Received from Device Gateway |
| 5.6 | Patient instructions received from Device Gateway |
| 6 | Device Events (Access requests) |
| 6.1 | Clinician login attempt |
| 6.2 | Biomed login attempt |
| 6.3 | Device access unlock attempt |
| 7 | Device Events (Configuration Updates) |
| 7.1 | DAL update available |
| 7.2 | DAL update received |
| 7.3 | DAL update installed |
| 7.4 | DAL update rejected |
| 7.5 | Software update available |
| 7.6 | Software update received |
| 7.7 | SW update installed |
| 7.8 | SW update rejected |
| 7.9 | Detected different Battery installed |
| 7.1 | Detected new security certificate |
| 7.11 | Detected new Device Gateway address |
| 8 | Device Events (Logging) |
| 8.1 | Device identification |
| 8.2 | Event Log Created |
| 8.3 | Infusion log entrys deleted without sending |
| 9 | Device Events (Other) |
| 9.1 | Battery Status |
| 9.2 | Power off request |
| 9.3 | Sleep request |
| 9.4 | Battery current at recharge |
| 9.5 | Battery current when recharge stops |
| 9.6 | Time to reach control point |
| 9.7 | Device Hardware Status Array (provide a set of hardware parameters, e.g., 20 hardware parameters specific to the internal functioning of the device) |

The items listed as 1, 2, 3, 4, 5, 6, 7, 8, and 9 in Table 1 are pump event classes. When the medical device 145 is not connected to the device gateway 147, these events are stored in a local memory buffer of the medical device 145. While connected (and once re-connected), these events are published to the device gateway 147 using a secure protocol, e.g., SSL, SSH, symmetrical-key encryption, and/or asymmetrical-key encryption. As previously mentioned, the device gateway 147 may act as (or contain) a publish-subscribe engine that is configured to route pump events to interested subscribers.

Referring again to FIG. 1 the pump events may be sent to the CQI manager 4 that relates to the device events of the devices 26. These events may be used to monitor an entire fleet of the medical devices 26 across many facilities 10. For example, the Device Hardware Status Array 9.71 may be converted to a CQI message and is communicated to the CQI manager 4. A user may log into the CQI manager 4 to schedule maintenance events, order new parts based upon the data, to provide predictive or preventive maintenance, and/or to order new parts for preventative reasons or predictive reasons. The user may use deterministic heuristics to determine what to order, when to order it, and/or when to flag some of the devices 26 in various facilities 10 for maintenance. The CQI manager 4 may be used for supply chain management of parts for a fleet of devices 26, and may provide real-time information about the status of the fleet of devices 26. For example, the Device Hardware Status Array may include battery information such as the current at full charge, which indicates the health of an internal battery. For all of or a subset of the devices 26 among several facilities 10, the CQI manager 4 may automatically order new batteries when the health of the battery falls below a predetermined threshold. Additionally or alternatively, the CQI manager 4 may automatically schedule for the battery to be replaced in these identified devices of the devices 26.

Referring again to FIG. 8, a device application 151 (e.g., a pump application configured for operation with a pump) may be executed on the device gateway 147 (in some embodiments, they may be different hardware and/or software). The device application 151 subscribes to events published by the medical device 145.

The pump app 151 may process the stream of raw events and refine them into streams of higher-level clinical events, e.g., the reportable clinical event 149 which may be reported to a server of the hosted cloud services for storage therein (e.g., the database 30 of FIG. 2).

In some embodiments of the present disclosure, the device application 151 is deployed in a J2EE application server as a message driven bean ("MDB"). The MDB is a stateless component that subscribes to a Java Message Service (JMS) Topic, e.g., PumpTopic 150. An application server of the device gateway 147 may activate the device application 151 on a worker thread when a message is available.

The device application 151 is a stateful component and contains one pump handler 153 instance for each pump 145 deployed in the institution. The pump dispatcher 152 maintains a lookup table of pump handlers 153 using the pump's 145 serial number as a unique key.

The pump MDB uses the application server's naming service to access the pump application 151. It gets the pump's 145 serial number from the message header, and uses the pump dispatcher 152 to find the appropriate pump handler of the pump handlers 153. If the respective pump handler of the pump handlers 153 is busy (processing another message, on another thread, etc.), the pump MDB queues the message to the pump dispatcher 152 (to ensure messages are processed in sequence). If the respective pump handler of the pump handlers 153 is idle, the pump MDB asks the respective pump handler of the pump handlers 153 to process the event. Each pump handler of the pump handlers 153 maintains a set of finite state machines ("FSM"), each of which processes a relevant subset of the pump events (see Table 1 above), including a pump FSM 156, a program FSM 157, and a delivery FSM 158.

The pump FSM 156 is the top-level state machine that processes events which do not belong to any infusion. The program FSM 157 is a child state machine which is activated when an infusion programming context is started, and is responsible for processing infusion programming events. The delivery FSM 158 is a child state machine which is activated when infusion delivery is started, and is responsible for processing operational events during an infusion. A separate programming FSM 157 and delivery FSM 158 may be used because a secondary infusion (incl. loading, bolus, or titration) can be programmed while a primary infusion is in progress. The medical device's 145 operating model, e.g., pump FSM 156, may be used to construct reportable clinical events (RCEs) or to construct reportable biomed events (RBEs). For example, the pump FSM 156 may: keep track of if the pump 145 when it completes one infusion and revert to another which was suspended; keep track of programming of one infusion while another is running; and/or keep track of more than one high-priority operational alarm that may occur at one time. That is, the pump FSM 156 may include nested state models.

Each pump handler of the pump handlers 153 may also maintain some context objects to hold programming and delivery context information. These context objects will be generated as Biomed Events (for tracking pump utilization) when complete, and will be persisted for recovery, in case the pump application 151 needs to be restarted. The context objects may include an infusion state, an infusion mode, and an infusion segment. The infusion state includes the programming/delivery state data for primary and secondary infusions. The infusion mode includes the programming/delivery state data for a particular dose/rate (e.g. loading, bolus, and/or titration). The infusion segment includes the delivery state for an operational period within an infusion mode (e.g. pumping, stopped, alarmed, etc.). Upon processing the pump event 146, a respective FSM 156, 157, or 158 may transition to a new state, create, update or delete a context object, and output a reportable event (a CQI-message), such as a reportable biomed event 148 or a reportable clinical event 149. In a specific embodiment of the present disclosure, a list of reportable clinical events is shown in Table 2 as follows:

TABLE 2

| RCE ID | Reportable Clinical Event Name |
|---|---|
| Unmapped | |
| 0.01 | Pump Failure |
| 0.02 | Clinical Advisory |
| 0.03 | (Un)Successful Self-Test |
| 0.04 | Temperature Excursions |
| 0.05 | Secondary Alert/Alarm |
| 0.06 | Second Clinician Check |
| 0.07 | KVO Alarm (Group, Drug) |
| 0.08 | High Pressure Alert/Notification |
| 0.09 | Scheduled Service Notification |
| 0.10 | KVO Soft Limit Override (Group) |
| 0.11 | KVO Soft Limit Pullback (Group) |
| Alarms | |
| 1.01 | Air in Line (Group. Drug) |
| 1.02 | Up Stream Occlusion (Group) |
| 1.03 | Down Stream Occlusion (Group) |
| 1.04 | Tube Misload |
| 1.05 | Door Open |
| 1.06 | Syringe Misload |
| 1.07 | Syringe Incompatibility |
| 1.08 | Syringe Ajar |
| 1.09 | Inactivity Alarm |
| 1.10 | Alarm to Resolution to Start |
| 1.11 | Alarm to Silence Time |
| 1.12 | Silence to Resolution to Start |
| 1.13 | Battery Alerts/Alarms |
| Alerts and Notifications | |
| 2.01 | Standby Alert/Callback |
| 2.02 | Clinical Notification |
| 2.03 | (Near) End Infusion Notification |
| 2.04 | Upgrade Needed (at power down) |
| Infusion Story | |
| 3.01 | Begin Infusion Story |
| 3.02 | End Infusion Story |
| 3.03 | Link Infusion to Infusion Story |
| Infusion Delivery Status | |
| 4.01 | Start |
| 4.02 | Stop |
| 4.03 | Bag End |
| 4.04 | Infusion Complete |

TABLE 2-continued

| RCE ID | Reportable Clinical Event Name |
|---|---|
| 4.05 | Bolus Dose |
| 4.06 | Standby |
| 4.07 | Loading Dose |
| 4.08 | Restarts Up Stream Occlusion (Group) |
| 4.09 | Restarts Down Stream Occlusion (Group) |
| | Soft Limit Overrides |
| 5.01 | Dose Soft Limit Override |
| 5.02 | Titration Limit Override |
| 5.03 | Bolus Dose Soft Limit Override |
| 5.04 | Bolus Time Soft Limit Override |
| 5.05 | Load Dose Soft Limit Override |
| 5.06 | Load Time Soft Limit Override |
| 5.07 | Rate Soft Limit Override |
| 5.08 | Time Soft Limit Override |
| 5.09 | Concentration Soft Limit Override |
| 5.10 | Weight Soft Limit Override (Group) |
| 5.11 | BSA Soft Limit Override (Group) |
| 5.12 | Rate Soft Limit Override (Group) |
| 5.13 | Volume Soft Limit Override (Group) |
| | Programming |
| 6.01 | End Infusion Programming |
| 6.02 | New Infusion |
| 6.03 | Titration |
| 6.04 | Program Changes prior to Start |
| 6.05 | Wildcard Use |
| | Pullbacks to Hard or Soft Limit Violations |
| 7.01 | Dose Soft Limit Pullback |
| 7.02 | Dose Hard Limit Pullback |
| 7.03 | Titration Limit Pullback |
| 7.04 | Bolus Dose Soft Limit Pullback |
| 7.05 | Bolus Time Soft Limit Pullback |
| 7.06 | Load Dose Soft Limit Pullback |
| 7.07 | Load Time Soft Limit Pullback |
| 7.08 | Rate Soft Limit Pullback |
| 7.09 | Time Soft Limit Pullback |
| 7.10 | Concentration Soft Limit Pullback |
| 7.11 | Weight Soft Limit Pullback (Group) |
| 7.12 | BSA Soft Limit Pullback (Group) |
| 7.13 | Rate Soft Limit Pullback (Group) |
| 7.14 | Time Soft Limit Pullback (Group) |

Referring to FIGS. 4 and 8, the CQI Listener 93 of FIG. 4 may run inside each facility 82, can connect to the device gateway (99 in FIG. 4 or 147 of FIG. 8), and subscribe to CQI RCEs 149 or the CQI RBEs 148. The CQI Listener 93 of FIG. 4 may establish a secure private connection to the CQI receiver 108 in the hosted environment 83 (see FIG. 4). This connection may be physical (continuously connected) or logical (transient connection while transmitting messages).

The device gateway 147 may route the RCEs 149 or RBEs 148 to the CQI listener 93. The CQI listener 93 may ensure message durability (i.e. no messages are lost during transmission due to network congestion or disconnection). As a result, the CQI listener 93 may: (1) store each message to be transmitted to a local persistent queue (for buffering); (2) transmits each of the RCEs 149 and/or RBEs 148 from the head of the queue to the CQI Receiver 108; and/or (3) remove the message after receiving acknowledgement from the CQI receiver 108.

The CQI receiver 108 runs inside a hosted environment within 83. The CQI receiver 108 listens for and accepts secure network connection requests from one or more CQI listeners 93. The CQI receiver 108 receives RCEs 149 from each connected CQI listener 93. The CQI receiver 108 may ensure message durability, so upon receipt, it writes each RCE 149 into the database 105. The CQI receiver 108: (1) stores each message received (CQI messages) to a local persistent queue (for buffering); (2) appends each CQI message from the head of the queue to a table in a CQI event database; (3) acknowledges receipt of the message to the CQI listener 93 that sent the message; and (4) removes the CQI message from the local queue (as it is safely in the CQI event database 105).

As previously mentioned, the CQI Event Database 105 is implemented using a Master-Slave replication. That is, database 105 is the master while database 106 is the slave. With this approach, there are two copies of the CQI event database with identical schemas, in some specific embodiments. As insert, update, and delete transactions are applied to the master database 105, a database management system (DBMS) within the database 105 writes the changes to a journal, and is able to transmit unposted changes to the slave database 106.

Each CQI message (e.g., a RCE) may belong to a specific institution. This institution reference should match the institution which operates the medical device (e.g., a medical device of the medical devices 101 of FIG. 4 or the medical device 145 of FIG. 8) and which released the Drug Administration Library (DAL) which is deployed in that device. As a result, the CQI databases 105, 106 may require a list of institutions which are consistent with the DERS database 113.

Figure 9:
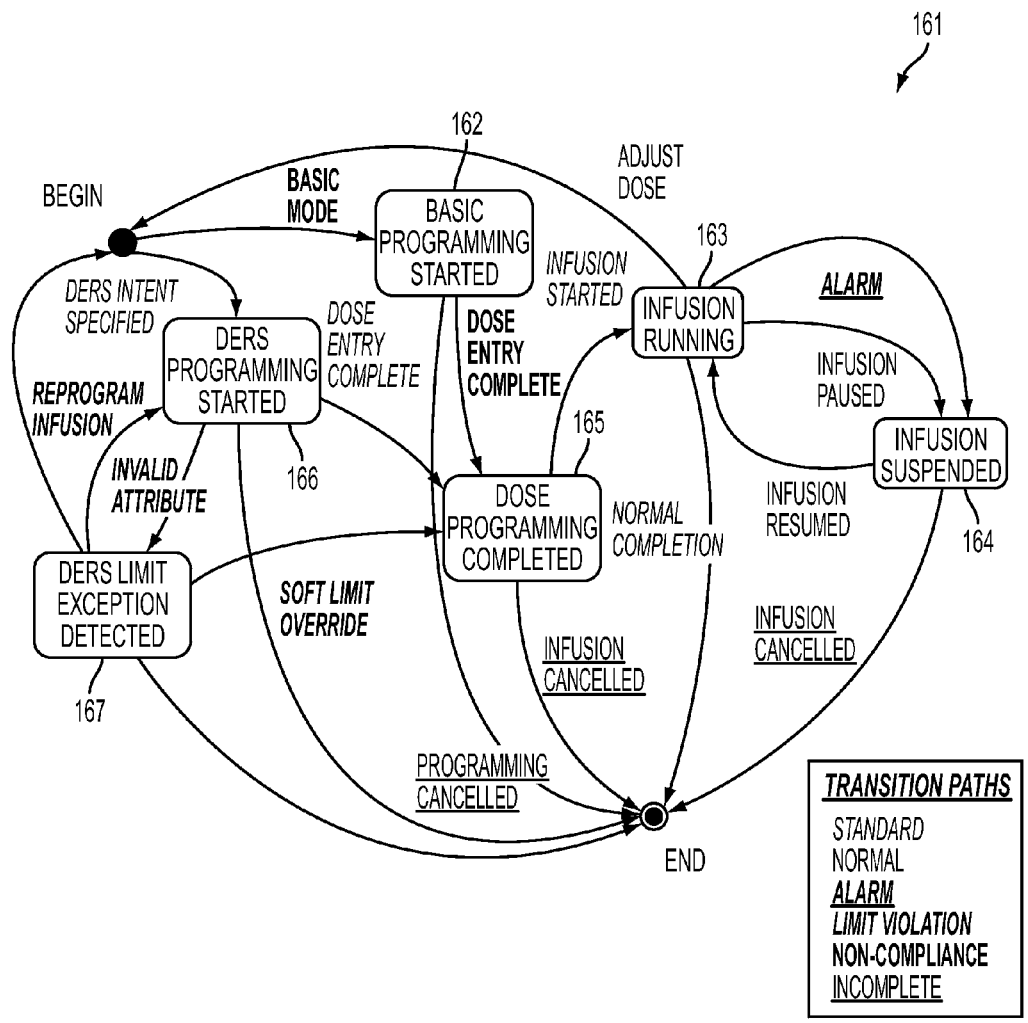
FIG. 9 shows a state diagram illustrating a method of programming an infusion device in accordance with an embodiment of the present disclosure.

FIG. 9 shows a state diagram illustrating a method 161 of programming an infusion device (e.g., of devices 16 of FIG. 1) in accordance with an embodiment of the present disclosure. The method 161 begins with the user capable of interfacing with a UI of the device.

The infusion programming starts in the state shown as the state labeled as "begin." State 162 is when the basic mode programming is used (e.g., when a DERS compliance exception device is used, for example). After programming using a DERS compliance exception device, the method transitions to state 165 in which the dose programming is complete.

State 166 is when the DERS-based protection is used and dose parameters are programmed into the device, which transitions to state 165 if no limit violation is detected. If there is a soft limit violation detected or a hard limit violation detected, the method 161 transitions to state 167. If it is a soft limit, the clinician may: (1) override the software limit which causes the method to continue to state 165; (2) program the infusion attributes with unchanged infusion intent, which either continues to state 165 if no new violation is found or to state 167 if a new violation is found; or (3) change the infusion intent (medication, clinical care area, clinical use and/or concentration) which causes the method 161 to restart at state 166.

If a hard limit is detected, the method transitions from state 166 to state 167, which requires the state to re-transitions back to state 166 and does not allow the clinician to override the DERS violation.

The infusion method 161 may be cancelled during many states. In the basic mode programming state 162, the clinician can cancel the infusion before programming is completed. In the DERS programming state 166, the clinician can cancel the infusion before the programming is completed. In state 167 when a DERS soft limit or hard limit violation has been detected, the clinician can cancel the infusion 4.

During state 165, the medical device will present an "infusion start" button in which the caregiver can press to transition to medical device to state 163, in which the infusion begins. A suspend button is present on the user interface when in state 163, which causes the device to suspend when pressed thereby transitioning the device to state 164. A continue button is present on the user interface when in state 164, which causes the device to return to state 163 when pressed to continue therapy. If a fatal error (a predetermined set of errors) is detected in states 163 and/or 164, the method 161 transitions to the end state.

Upon completion of the infusion, the pump sends an infusion complete message to the clinical server via the device gateway. The clinical server links the completion event to the prescription record. The clinical server formats an IHE auto-documentation message and sends it to one of the facility IT apps 11 (see FIG. 1), e.g., for recording in an Electronic Medical Administration Record ("eMar"), to update the patient's Electronic Medical Record (EMR) 17, and/or update the hospital's billing system to record successful infusion of the medication.

Figure 10:
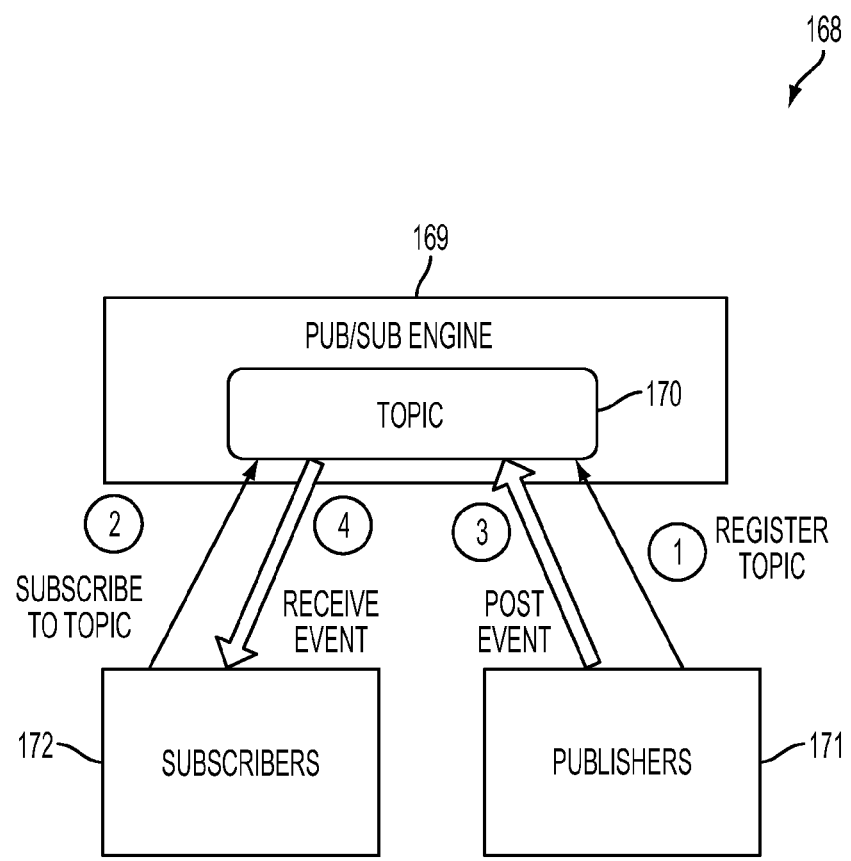
FIG. 10 illustrates a publish-subscribe model for used by the facility gateway of FIG. 1, and by the applications and the device gateway shown in FIGS. 2 and 4 in accordance with an embodiment of the present disclosure.

FIG. 10 illustrates a publish-subscribe model 168 for used by the facility gateway 21 of FIG. 1, by the applications 41, 42, 43, 44 and device gateway 40 in FIG. 2 or FIG. 4 in accordance with an embodiment of the present disclosure.

The model uses a pub/sub engine 169 that allows publishers 171 to register one or more topics 170 with the pub-sub engine 169. Once the topic 170 is registered, one or more subscribers 172 can subscribe to the topic 170. The subscribers 172 may subscribe using a guaranteed subscription to the topic 170, in some specific embodiments. When a publisher of the publishers 171 posts an event related to the topic 170, all subscribers of the subscribers 172 that have subscribed to the topic 170 receive the data from the pub/sub engine 169.

A publisher (of the publishers 171) may register one or more topics 170, each topic may be a unique topic. One or more subscribers 172 may subscribe to one or more topics of the topics 170 to receive events therefrom. When a publisher 171 posts an event to a unique topic (e.g., a "first topic") of the topics 170, all subscribers to the first topic of the topics 170 will receive that event; nonsubscribers to the first topic of the topics 170 will not receive that event and subscribers 172 subscribed to other topics (e.g., a second optic) of the topics 170 but not the first topic will not receive the event sent that only corresponded to the first topic.

The topics 170 may provide a level of indirection enabling the publishers 171 and the subscribers 172 to be anonymous, in some embodiments. The pub/sub engine 169 may allow the communication to be one-way and asynchronous (e.g., a "fire and forget" communication). The pub/sub engine 169 may provide durable message delivery, on both sides. Durable topics of the topics 170 may ensure that messages will not be lost if the pub-sub engine 169 fails. Durable subscriptions used by the subscribers 172 may ensure that a subscriber 172 will not miss messages when it is not running.

The pub/sub engine 169 may be part of the device gateway 22, may be part of any other software within the facility gateway 21, or may be a stand-alone application of FIG. 1. The pub/sub engine 169 may be part of the device gateway 40, within an application 41-44, or may be a stand-alone application of FIG. 2. The pub/sub engine 169 may be part of the device gateway 99 of FIG. 4, may be part of the applications 94, 96, 97, or may be a stand-alone application of FIG. 4.

Figure 11:
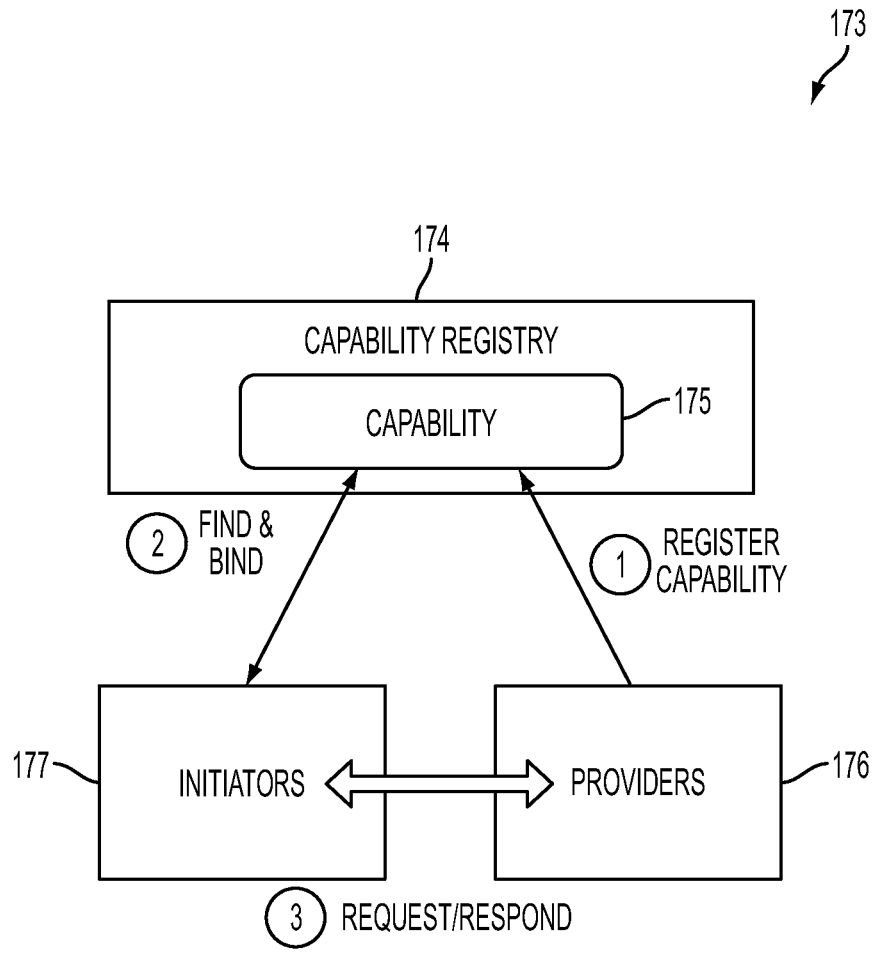
FIG. 11 illustrates a capability-registry model in accordance with an embodiment of the present disclosure.

FIG. 11 illustrates a capability-registry model 173 in accordance with an embodiment of the present disclosure. A provider 176 registers its capability 175 with a capability registry 174. The capability 174 may include two aspects, including an interface and an attribute. The interface is the list of request/response pairs and notifications (in both directions). The attributes is the service level agreement parameters specifying limits on the quality of delivery (e.g. response times, error rates and recovery policies, costs, etc.).

An initiator 177 can communicate with the capability registry 174 to find and bind to the capability. Thereafter, the initiators 177 can request information from the providers 176 and receive a response. The capability registry 174 may be part of the device gateway 22, may be part of any other software within the facility gateway 21, or may be a stand-alone application of FIG. 1. The capability registry 174 may be part of the device gateway 40, within an application 41-44, or may be a stand-alone application of FIG. 2. The capability registry 174 may be part of the device gateway 99 of FIG. 4, may be part of the applications 94, 96, 97, or may be a stand-alone application of FIG. 4. The capability registry 174 may supplement or replace the pub/sub engine 169 in some specific embodiments.

Figure 12:
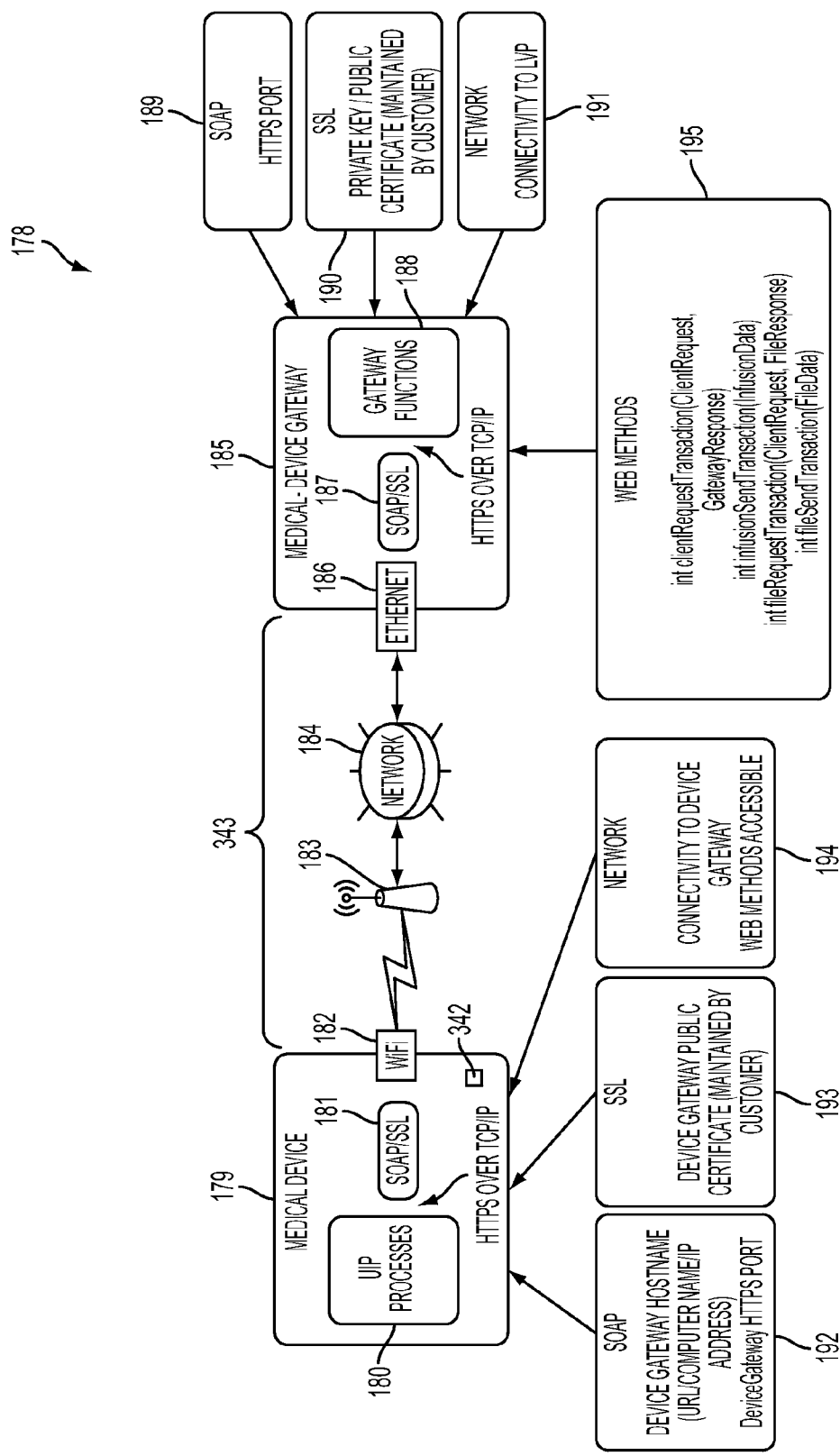
FIG. 12 shows a block diagram of a system to illustrate communications between a medical device and a device gateway in accordance with an embodiment of the present disclosure.

FIG. 12 shows a block diagram of a system 178 to illustrate communications between a medical device 179 and a device gateway 185 in accordance with an embodiment of the present disclosure. The medical device 179 may utilize a device gateway communication manager ("DGCM") 342 to communicate with the device gateway 185. The communications may be based on web services, where the medical device 179 is the client, and the device gateway 185 is the web server using the HTTPS communication transport.

Communication is in the form of transactions, where the medical device 179 invokes web methods hosted on the device gateway 185 (e.g., a medical-device gateway). The medical device may use a WiFi connection 182 that communicates with the device gateway 185 using a WiFi router 183, coupled to a network 184 that is coupled to the device gateway 185 via an Ethernet connection 186. In one specific embodiment, TCP/IP provides the transport protocol over the network 184, SOAP provides the messaging format that is compliant with HTTP, and SSL provides the encryption/authentication required for secure communication (HTTPS). Within the medical device's 179 software, the communications manager manages the client side of the web services communication.

The communications manager communicates with the device gateway 185 by invoking one of the web methods hosted on device gateway 185 by using SOAP messaging and SSL over HTTPS. This may use a SOAP binding 187 for the software language used to implement the interface. In addition, the SOAP binding 187 may have SSL capability to provide secure communication over HTTPS. A web-services description language ("WSDL") file is created that defines the web service operations (web methods 195) and schemas required for the web server of the device gateway 185. A WSDL file may be created for the web methods 195 and data types used. Using the WSDL and the SOAP provider's utility tool, SOAP client source code files are generated and added to the communications manager software. In order for communications manager to successfully initiate a transaction with device gateway 185, the following may be used/set-up: (1) OpenSSL 179 installed on the medical device 185 (software 181); (2) device gateway's 185 host name and IP port stored in the data structure 192; (3) device gateway's 185 public certificate data structure 193 reside on the medical device 179; and (4) the medical device's 170 private key and public certificate 194 reside on the medical device 179.

The device gateway 185 is configured as a web server and hosts the web methods 195 that remote devices (e.g, the medical device 179) access in order to retrieve information from or pass information to device gateway 185. Because HTTPS is used for secure communication, the device gateway may use a SOAP and SSL interface 187. A WSDL file may be created that defines the web service operations (e.g., the web methods 195) and the data types required for the web server. A WSDL file has been created for the web methods 195 and data types required. Using the WSDL and the SOAP provider's utility tool, SOAP server source code files are generated and added to the device gateway 185 software to facility providing the gateway functions 188. In order for device gateway 185 to process a transaction from medical device 179, the following may be used/set-up: (1) OpenSSL 187 (or equivalent software) installed on device gateway 185, which can provide a communications port 189 and network connectivity 191; (2) medical device 179 public certificate may reside on device gateway 185 in a data structure 190; and/or (3) the device gateway's 185 private key and public certificate reside on device gateway 185 in a data structure 190.

The web services implementation defines the communications interface between the medical device 179 and the device gateway 179 for the purpose of establishing communication and exchanging information. This communication is in the form of transactions, initiated by invoking a device gateway 185 hosted web method 195. Four web methods are used to pass information between the medical device 179 (using the DGCM 342) and the device gateway 185. The web methods are hosted on the device gateway 185 and invoked by the DGCM 342 to initiate an information exchange transaction with the device gateway 185. Each web method may be used for specific types of information moving, as identified in Table 3. In one specific embodiment, a list of these transactions and associated web methods can be found in the following Table 3:

TABLE 3

| Web Method | Transaction Type |
| --- | --- |
| device_clientRequestTransaction | Communication Status Check with device gateway |
| | Time Information Check/Retrieval from device gateway |
| | Patient Infusion Program Check/ Retrieval from device gateway |
| | Patient Instructions Check/ Retrieval from device gateway |

TABLE 3-continued

| Web Method | Transaction Type |
| --- | --- |
| | Patient Scalar Data Check/ Retrieval from device gateway |
| | Device Information Check/ Retrieval from device gateway |
| | Alert Notification Check/ Retrieval from device gateway |
| device_fileSendTransaction | Service Log File Post to device gateway |
| | Engineering Log File Post to device gateway |
| device_fileRequestTransaction | Debian Software Package Check/ Retrieval from device gateway |
| | DAL Configuration File Check/ Retrieval from device gateway |
| device_infusionSendTransaction | Infusion Log Information Post to device gateway |

The Communication Status Check transaction is used to register the medical device 179 with the device gateway 185, maintain communication with device gateway 185, and to retrieve status regarding available information that the device gateway 185 is holding for the medical device 179. The Patient Infusion Program Check, Patient Instructions Check, Patient Scalar Data Check, Device Information Check, Alert Notification Check, Debian Software Package Check, and DAL Configuration File Check transactions are used to retrieve available device gateway 185 information that was identified within the prior Communication Status Check response from the device gateway 185. The Service Log File Post and Engineering Log File Post transactions are used to send log files to the device gateway 185 that were identified within the prior Communication Status Check response from the device gateway 185. The Infusion Log Information Post transaction to the device gateway 185 is initiated whenever infusion log events available within the medical device 179 have not been already sent to device gateway 185. Files may be transferred between the medical device 179 and the device gateway as a DIME attachment to the SOAP message. The Time Information Check transaction is used to retrieve the device gateway's 185 time for time synchronization.

The web methods 184 are used to retrieve information from the device gateway 185 and to pass information to the device gateway 185. The web methods 184 are shown in Table 4 with their C-style Prototype as follows:

TABLE 4

| Web Method | Purpose | C-style Prototype |
| --- | --- | --- |
| Client Request Transaction | used to retrieve information from the device gateway such as status, time, patient data, device data | int device_clientRequestTransaction(struct device_ClientRequest_T *request_ptr, struct device_GatewayResponse_T &response); |
| Infusion Send Transaction | used to send infusion log information to device gateway | int device_infusionSendTransaction(struct device_InfusionData_T *data_ptr, int &result); |
| File Request Transaction | used to request software or DAL file from device gateway | int device_fileRequestTransaction(struct device_ClientRequest_T *request_ptr, struct device_FileResponse_T &response); |
| File Send Transaction | used to send engineering or service log file to devicegateway | int device_fileSendTransaction(struct device_FileData_T *data_ptr, int &result); |

Figure 13:
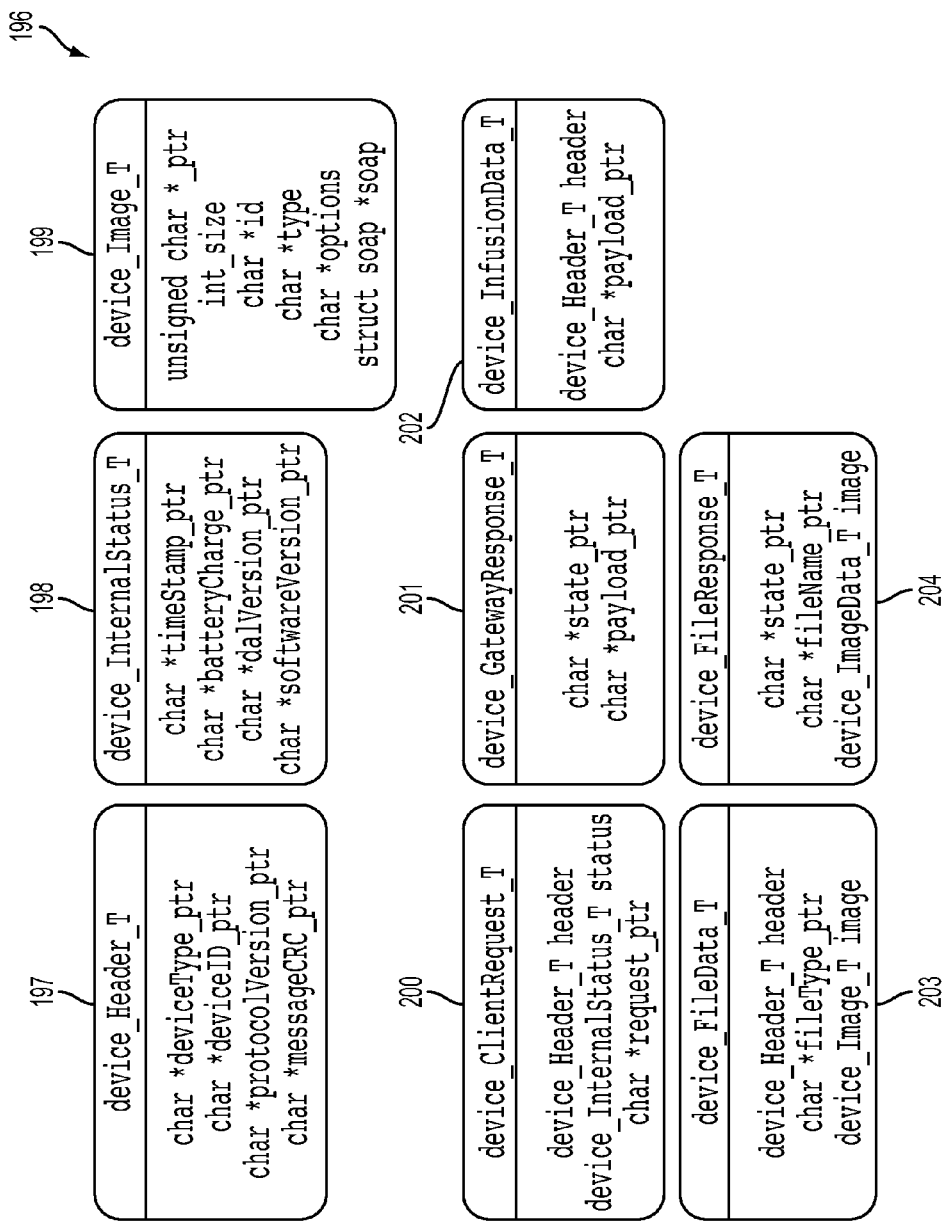
FIG. 13 shows the data structure declarations for use with the web methods to facilitate communication between the medical device and the device gateway of FIG. 1, 2 or 4 in accordance with an embodiment of the present disclosure.

In some embodiments, each passed parameter may be a data structure or an int (i.e., an integer data type of C). In other embodiments, any data type may be passed. The data structure declarations are shown in FIG. 13. All data structure member pointers (other than device_Image_T 199, which is a data structure required by gSOAP's implementation) are to null terminated character strings. The parameter list within the web method contains one or more parameters for passing information to the device gateway 185 (see FIG. 12) and one parameter for receiving information from the device gateway 185. The passing parameters can be by value, by reference, or by pointer. The receiving parameter is always the last in the parameter list and is a referenced data type (&dataType). Even when the web method does not have information to return, the receiving parameter is still required. For example, device_infusionSendTransaction( . . . , int &result) and device fileSendTransaction( . . . , int &result) use "&result" to meet this requirement.

Each web method has a return value that identifies the transaction completion state to the initiator. An exemplary set of return values are provided in Table 5 as follows:

TABLE 5

| Web Method Return Value | Description |
| --- | --- |
| 0 | Transaction successful |
| >0 | Transaction error |

Referring again to FIG. 13, the member pointers of the device_Header_T 197 are shown and described in the following Table 6 as follows:

TABLE 6

| Member Pointer | Description |
| --- | --- |
| char *deviceType_ptr | Identifies the device model number. |
| char *deviceID_ptr | Identifies the device's unique serial number. |
| char *protocolVersion_ptr | Identifies the device gateway communication manager protocol version to insure communication compatibility between device gateway communication manager of the medical device and the device gateway. |
| char *messageCRC_ptr | Message CRC provides the CRC32 calculated value for the data structure' contents. When calculating the CRC, the messageCRC location is ignored. The calculated value is then used to populate the messageCRC location. |

The member pointers of the device_InternalStatus_T 198 are shown and described in the following table 7 as follows:

TABLE 7

| Member Pointer | Description |
| --- | --- |
| char *timeStamp_ptr | Provides the local time at which the Communication Status Check transaction is initiated. The format of the timestamp (YYYY-MM-DD HH:mm:ss) is demonstrated by the following example: 2012-07-23 15:15:30 represents local time 3:15:30PM on Jul. 23, 2012 (local time zone) |
| char *batteryCharge_ptr | Identifies the charge of the medical device's battery |

TABLE 7-continued

| Member Pointer | Description |
| --- | --- |
| char *dalVersion_ptr | Identifies the version of the DAL configuration file loaded on the medical device. |
| char *softwareVersion_ptr | Identifies the version of the software package loaded on the medical device. |

Referring to FIGS. 12-13, the device_ClientRequest_T 200 identifies the type of the information the medical device's 179 communication manager is requesting from the device gateway 185. In one specific embodiment, the following requests using device_ClientRequest_T 200 are shown and described in the following Table 8

TABLE 8

| Request | Description |
| --- | --- |
| HEARTBEAT | request information availability |
| TIME | request time (seconds since Jan. 1, 1970) |
| PROGRAM | request patient infusion program |
| INSTRUCTIONS | request patient instructions |
| DATA | request patient scalar data |
| DEVICE | request device information |
| NOTIFICATION | request active alert notifications |
| DAL | request DAL configuration file transfer |
| SOFTWARE | request debian software package transfer |

The device_GatewayResponse_T 201 provides the device gateway's 185 response to the received request. An exemplary embodiment of states (e.g., char*state_ptr) and a description of them are shown in Table 9 as follows:

TABLE 9

| State | Description |
| --- | --- |
| REJECTED | The device gateway has rejected the request. |
| NONE | The device gateway has no available information to provide. |
| AVAILABLE | The device gateway has information to provide. |

Char*payload_ptr provides the information requested by the medical device 179 via the device's 179 communication manager.

The device_FileData_T 203 identifies the type of file being sent to the device gateway 185. An exemplary embodiment of files types and a description of them are shown in Table 10 as follows:

TABLE 10

| File Type | Description |
| --- | --- |
| SERVICE | device's service log |
| ENGINEERING | device's engineering log |

The device_FileResponse_T 204 provides the device gateway's 184 response to the received request. An exemplary embodiment of the states and a description of them are shown in Table 11 as follows:

TABLE 11

| State | Description |
| --- | --- |
| REJECTED | The device gateway has rejected the request |
| NONE | The device gateway has no available file to transfer |

TABLE 11-continued

| State | Description |
|---|---|
| AVAILABLE | The device gateway has transferred the requested file to the device gateway communication manager |

The char*filename_ptr identifies the file transferred to the device gateway communication manager 342. The char*payload_ptr of the device_InfusionData_T 202 provides the infusion log information as XML to the device gateway 185. The payload is organized as XML elements where there is a root element and child elements.

Figure 14:
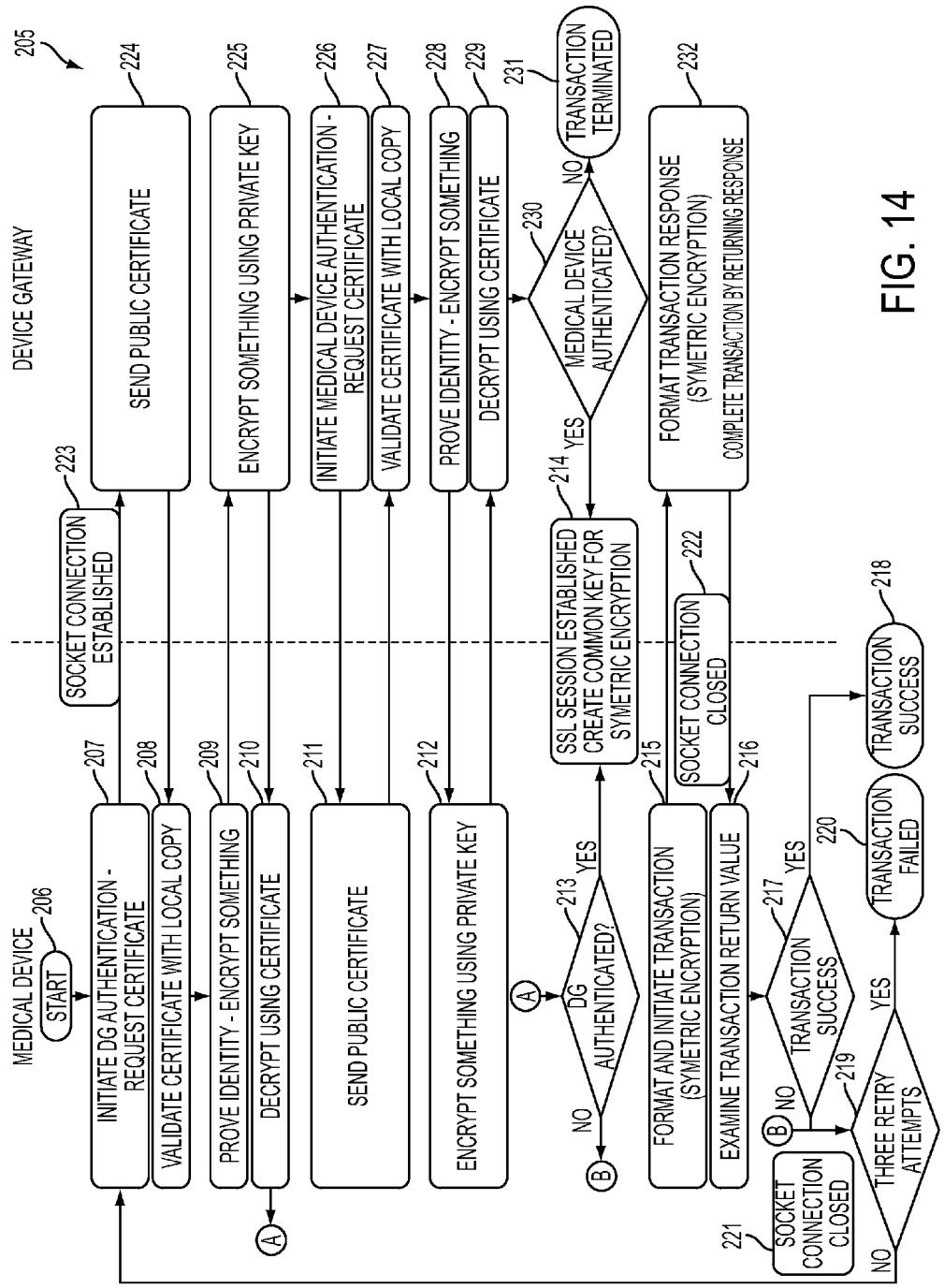
FIG. 14 shows a flow chart illustrating a method of communication between a medical device and a device gateway in accordance with an embodiment of the present disclosure.

FIG. 14 shows a flow chart illustrating a method 205 of communication between a medical device and a device gateway in accordance with an embodiment of the present disclosure. That is, method 205 is a generic transaction sequence between a medical device (using a DGM) and a device gateway. The method 205 may be used by the methods shown in FIGS. 15-26 to perform their respective transactions.

Generally, a transaction consists of the DGCM 342 of the medical device invoking a device gateway hosted web method. This action establishes an HTTPS connection with the device gateway. During connection establishment, authentication using asymmetric encryption is performed between the medical device and the device gateway to establish a secure/trust relationship. Once authenticated, an SSL session is established and the two endpoints create a common key and use symmetric encryption for data passing. The transaction is processed, information is returned, and the HTTPS connection is closed. Up to three transaction retries are attempted to achieve a successful transaction before failing. FIG. 14 shows a specific embodiment, i.e., method 205, of this transaction.

The method 205 includes acts 206-232. Act 206 enters the method. Act 207 initiates the device gateway authentication and requests a certificate. A socket connection is established in act 223. In act 224, the device gateway receives the request and sends the public certificate to the medical device. In act 208, the medical device validates the public certificate by comparing it to a local copy. In act 209, the medical device requests that the device gateway prove its identify by encrypting data (e.g., predetermined data, such as a serial number or ID number of the device gateway). The data is then sent from the medical device to the device gateway.

The device gateway may then encrypt a message (e.g., a serial number or ID of the device gateway) using its private key during act 225 and sends the encrypted messages to the medical device. In act 210, the message is decrypted using a public certificate of the device gateway.

Act 226 initiates a medical device authentication by requesting a certificate, which is received by the medical device, which sends the public certificate in act 211 to the device gateway. In act 227, the device gateway will validate the certificate by comparing it with a local copy. In act 228, the device gateway requests that the medical device prove its identify by encrypting some data (e.g., predetermined data, such as a serial number or ID number of the medical device).

In act 212, the medical device encrypts data (e.g., the predetermined data). The encrypted data is send to the device gateway which decrypts the data in act 229. In act 230, the device gateway determines if the medical device is authenticated and in act 213 the medical determines if the device gateway is authenticated. If both are authenticated, act 214 establishes a session key. If the device gateway cannot authenticate the medical device in act 230, the transaction is terminated in act 231. If the medical device cannot authenticate the device gateway, the medical device will try for up to three times (see 219) and the transaction will be considered a failure in act 220 after three attempts.

In act 215, after the SSL session is established in act 214, the medical device formats a transaction (e.g., a web method) and uses the ssl symmetric encryption key to send the transaction to the device gateway. Act 232 decrypts the web method after it receives the web method, processes the web method, and formats a response. Act 232 encrypts the response (e.g., a return value) which is sent to the medical device. The medical device decrypts the response and examines the return value in act 216. In act 217, the medical device will determine if the return value corresponds to a successful transaction and declare a successful transaction in act 218. If the transaction was not a success, act 217 will initiate another attempt by act 219.

Figure 15:
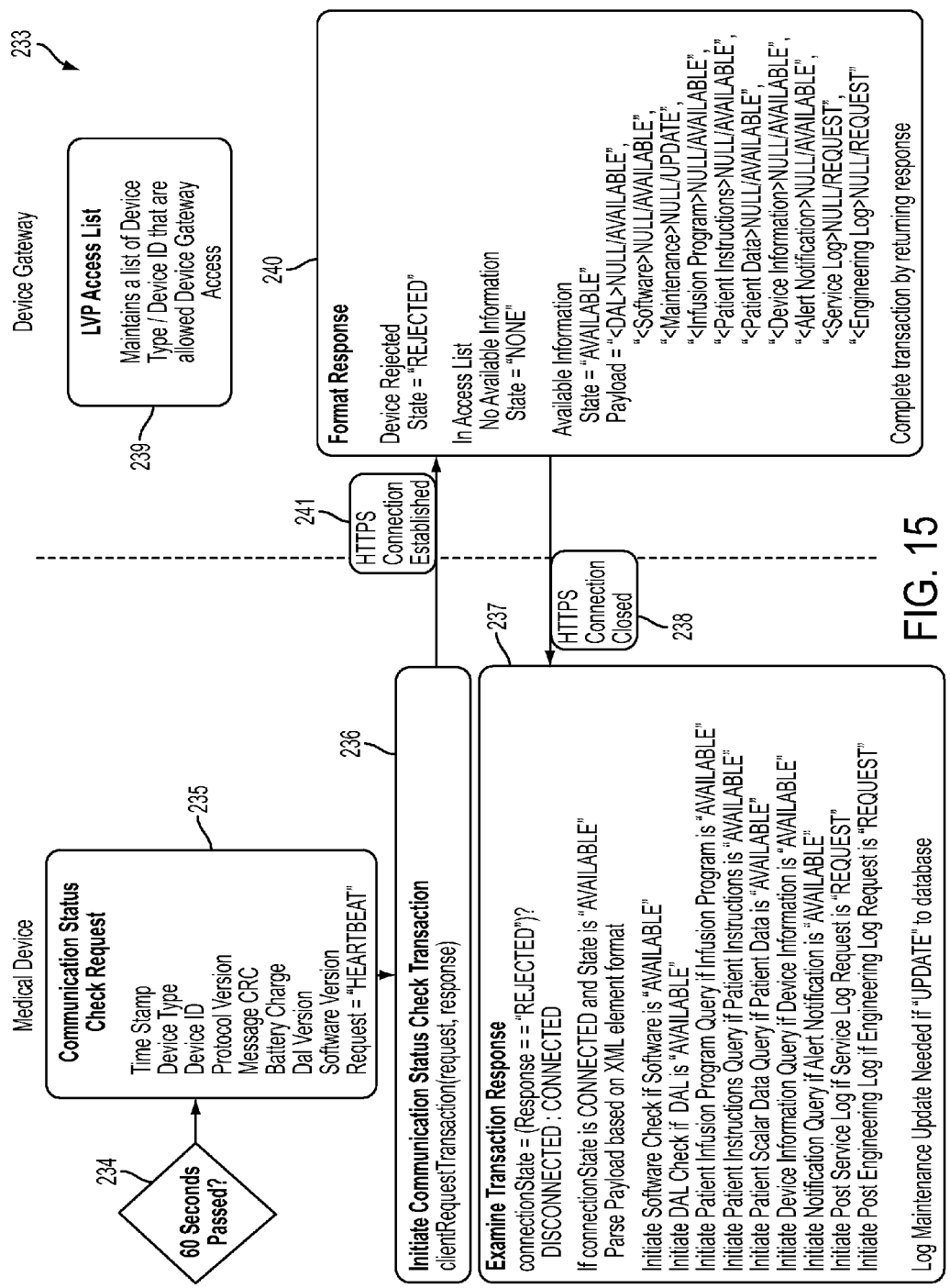
FIG. 15 shows a flow chart illustrating a method of communication between a medical device and a device gateway to perform a status and communication check in accordance with an embodiment of the present disclosure.

FIG. 15 shows a flow chart illustrating a method 233 of communication between a medical device and a device gateway to perform a status and communication check in accordance with an embodiment of the present disclosure. The communication status check transaction is periodically initiated by the DGCM 342 to establish communication with the device gateway (which transitions from Disconnected to Connected), to maintain communication with the device gateway (maintain Connected, transition to Disconnected), and to retrieve status information regarding available information that the device gateway is holding for the medical device.

Method 233 includes acts 234-238 and 240-241. Act 234 initiates the status check every 60 seconds. Act 234 receives the status check request (e.g., the DGCM 342 receives it). Act 236 sends the requests and establishes a HTTPS connection in act 241. Table 239 shows the access list of medical devices that can access the device gateway.

In act 240, the device gateway will determine if the medical device is on the access list 239 and will formulate a response including the information that is available for the medical device. The response is sent to the medical device which examines it in act 237.

The device gateway sets the Response State to REJECTED if the medical device is not a member of the device access list 248. The device gateway sets the available information to NONE if it is not available for the medical device, and otherwise sets the appropriate element within the XML-based Response Payload to the values in Table 12 as follows:

TABLE 12

| Element Identification | Element Value (e.g., as text) |
|---|---|
| DAL | AVAILABLE |
| SOFTWARE | AVAILABLE |
| MAINTENANCE | UPDATE |
| PROGRAM | AVAILABLE |
| INSTRUCTIONS | AVAILABLE |
| DATA | AVAILABLE |
| DEVICE | AVAILABLE |
| NOTIFICATION | AVAILABLE |
| SERVICELOG | REQUEST |
| ENGINEERINGLOG | REQUEST |

Figure 16:
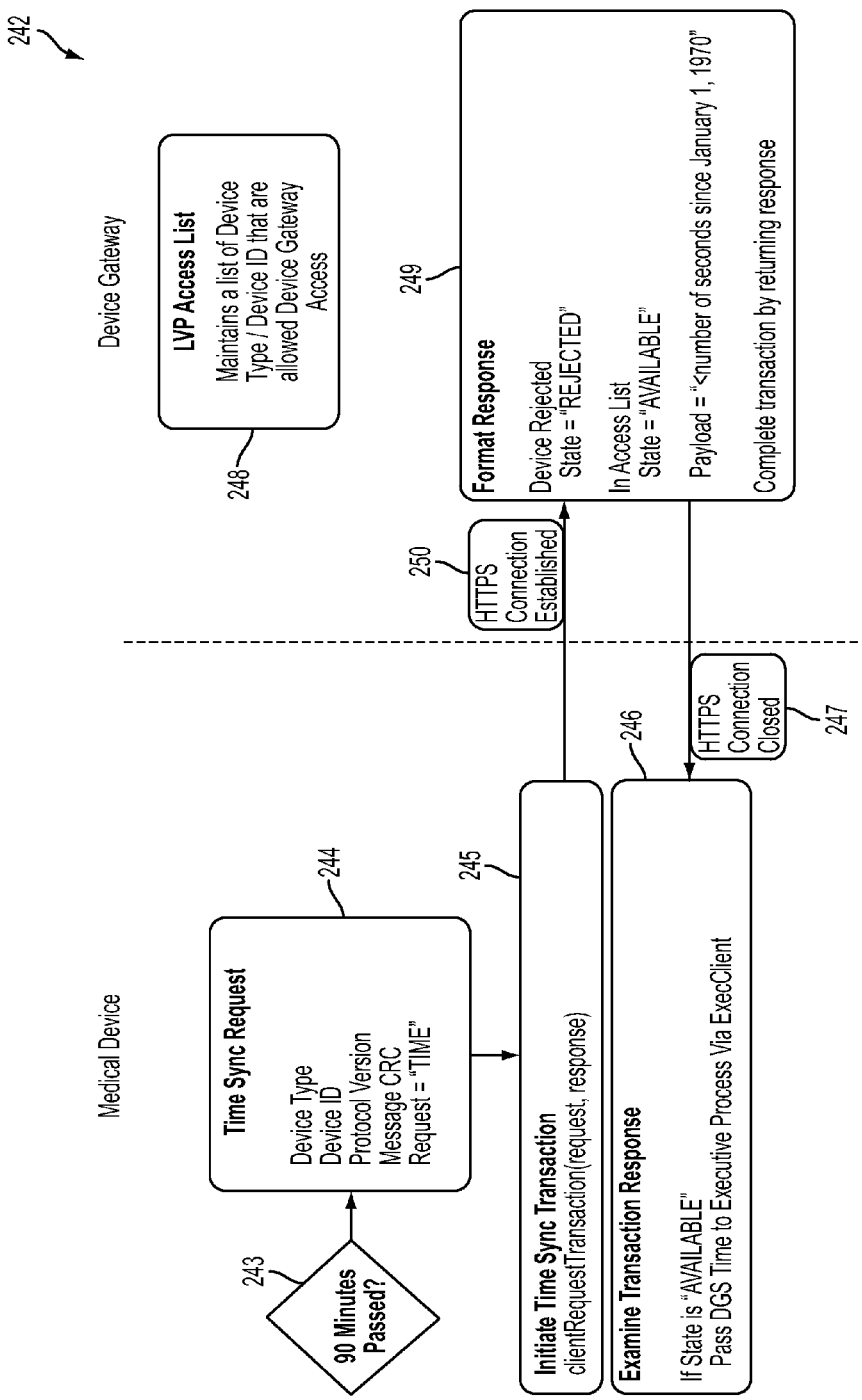
FIG. 16 shows a flow chart illustrating a method of communication between a medical device and a device gateway to synchronize their respective clocks in accordance with an embodiment of the present disclosure.

FIG. 16 shows a flow chart illustrating a method 242 of communication between a medical device and a device gateway to synchronize their respective clocks in accordance with an embodiment of the present disclosure. The method 242 implements the time synchronization transaction periodically by the DGCM of the medical device to retrieve the device gateway's current date and time. The information is used to update the medical Device's real-time clock so that it matches the real-time clock of the device gateway.

Act 243 periodically (e.g., every 90 minutes) initiates a TIME request. The request is formatted as a web method in act 245 which communicates it to the device gateway by establishing a HTTPS connection in act 250. In act 249, a response is formatted, which includes a payload indicating the time of the device gateway. If the medical device is not a member of the device gateway's device access list 248, the state is set to REJECTED, otherwise it is set to AVAILABLE. If the state is set to AVAILABLE, the device gateway formats the response payload as the number of seconds passed since Jan. 1, 1970. The device gateway communicates the response via a HTTPS connection which is closed in act 247 after transmission. Act 246 examines the response by the device gateway.

Figure 17:
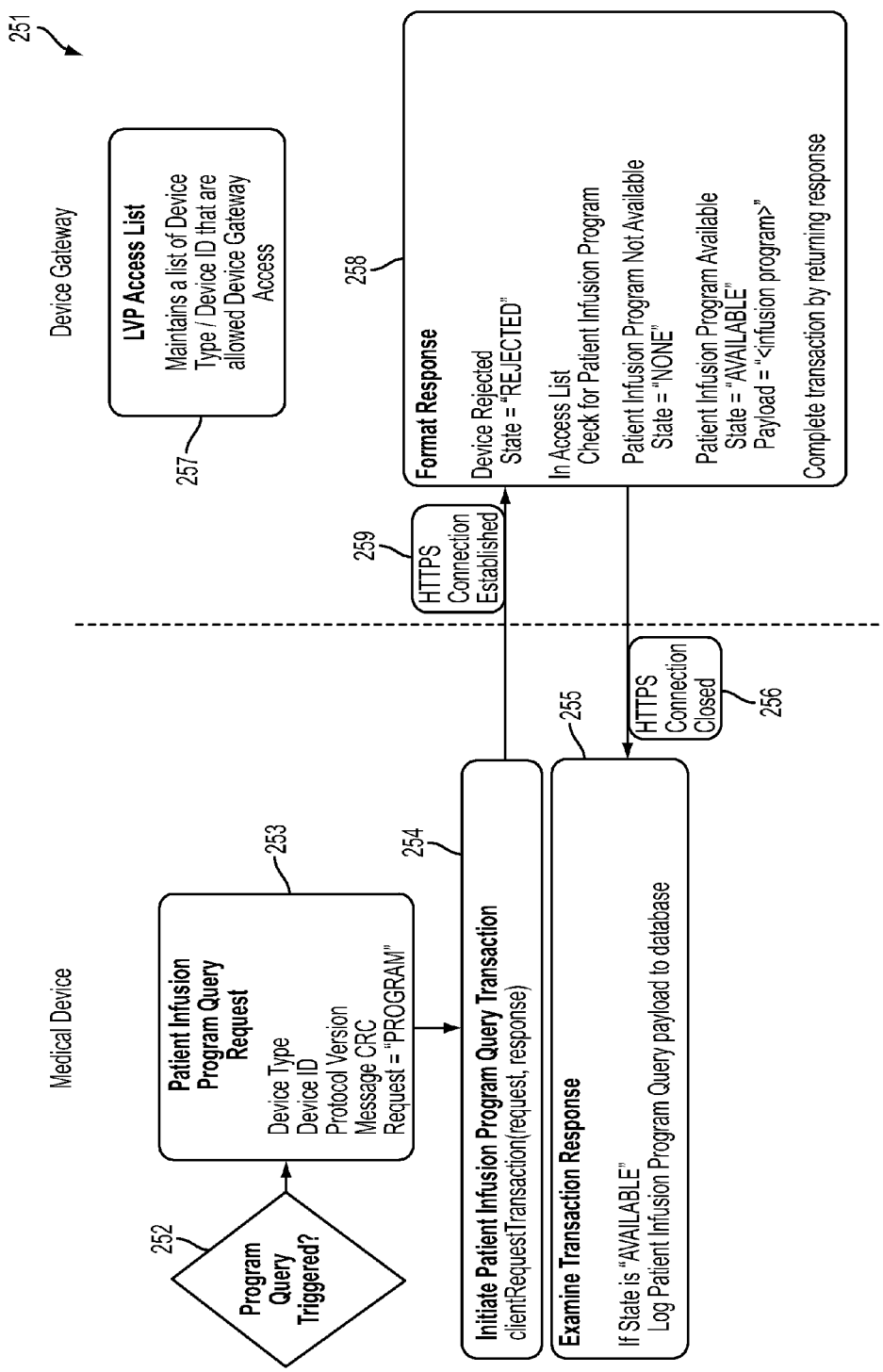
FIG. 17 shows a flow chart illustrating a method of communication between a medical device and a device gateway to perform a patient infusion transaction in accordance with an embodiment of the present disclosure.

FIG. 17 shows a flow chart illustrating a method 251 of communication between a medical device and a device gateway to perform a patient infusion transaction in accordance with an embodiment of the present disclosure. The patient infusion program check transaction implemented as method 215 is initiated to retrieve the available patient infusion program from device gateway. The patient infusion program may be one or more infusion parameters, e.g., flow rate, dose to be delivered, drug to be infused, etc. The transaction is initiated whenever an INFUSION AVAILABLE has been received from a previous communication status check transaction, which triggers the method 251.

Act 252 receives the trigger. Act 253 initiates a "PROGRAM" request which is formatted into a web method in act 254. The web method is transmitted to the device gateway via an HTTPS connection that is established in act 259. Act 258 processes the web method and formats a response. The device gateway sets the response state to REJECTED if the medical device is not a part of the access list 257. If a patient infusion program is not available for the medical device, the state is set to NONE, otherwise, it is set to AVAILABLE. The infusion program may be part of the payload or references a text-based infusion program. The response is communicated to the medical device which examines the transaction response in act 255. Act 256 closes the HTTPS connection after the response is transmitted.

Figure 18:
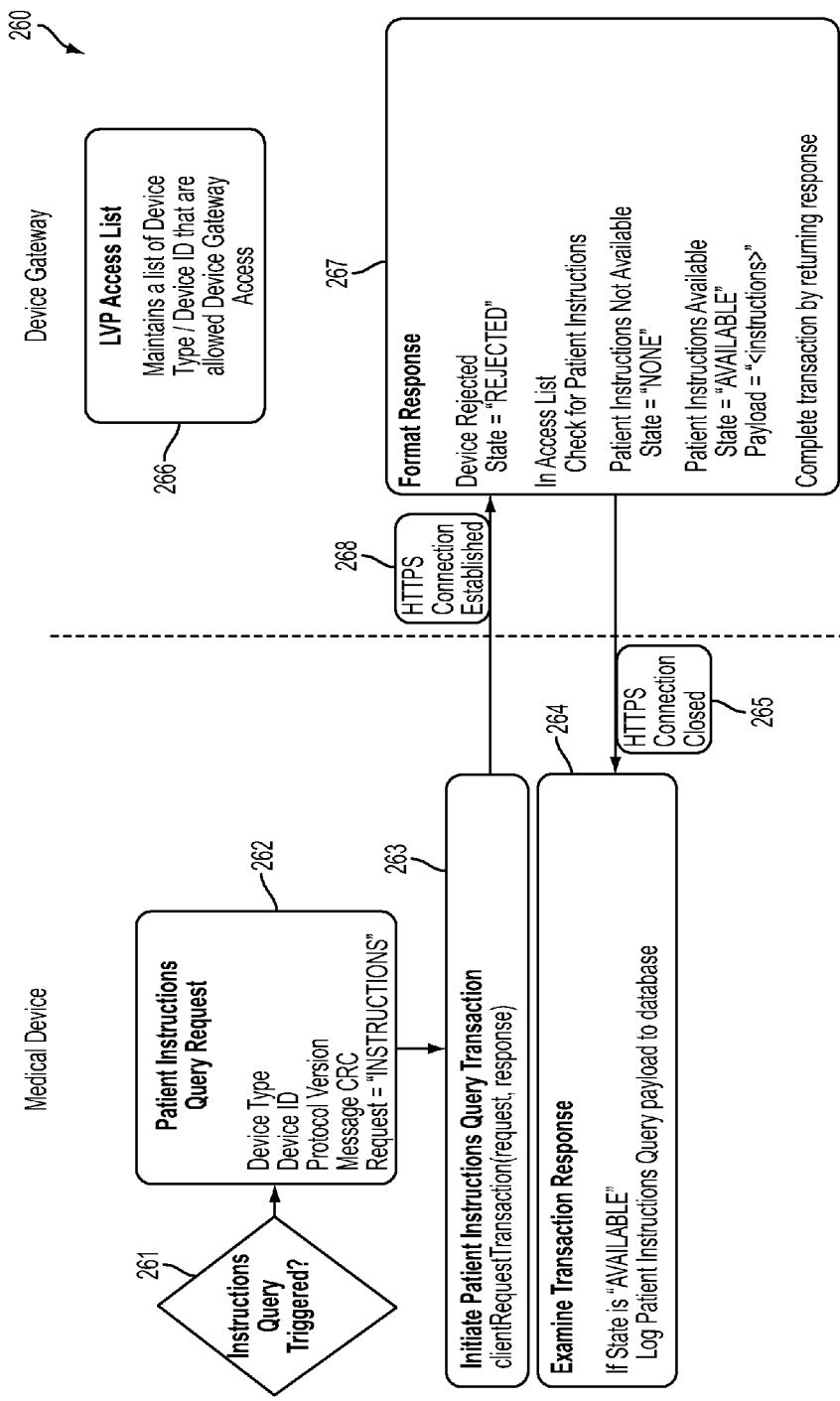
FIG. 18 shows a flow chart illustrating a method of communication between a medical device and a device gateway to perform a patient instructions transaction in accordance with an embodiment of the present disclosure.

FIG. 18 shows a flow chart illustrating a method 260 of communication between a medical device and a device gateway to perform a patient instructions transaction in accordance with an embodiment of the present disclosure. This Patient Instructions Check transaction is initiated to retrieve the available patient instructions from the device gateway. The transaction (shown as method 260) is initiated whenever an INSTRUCTIONS AVAILABLE has been received from a previous communication status check transaction (e.g., see FIG. 15).

In act 261, the method 260 is initiated. In act 262, the patient instruction query request is initiated, and in act 263, a web method is formatted and sent to the device gateway using a HTTPS connection that is established in act 268. In act 267, the device gateway formats a response which is sent to the medical device. If the medical device is not a member of the device gateway's access list 266, the state is set to REJECTED. If the medical device is a part of the gateway's access list 266 and no patient instructions are available, the state is set to NONE. If the medical device is a part of the gateway's access list 266 and patient instructions are available, the state is set to AVAILABLE and the device gateway formats the response payload to reference or include the text based patient instructions. After the response is sent, the HTTPS connection is closed in act 265. In act 264, the response is examined.

Figure 19:
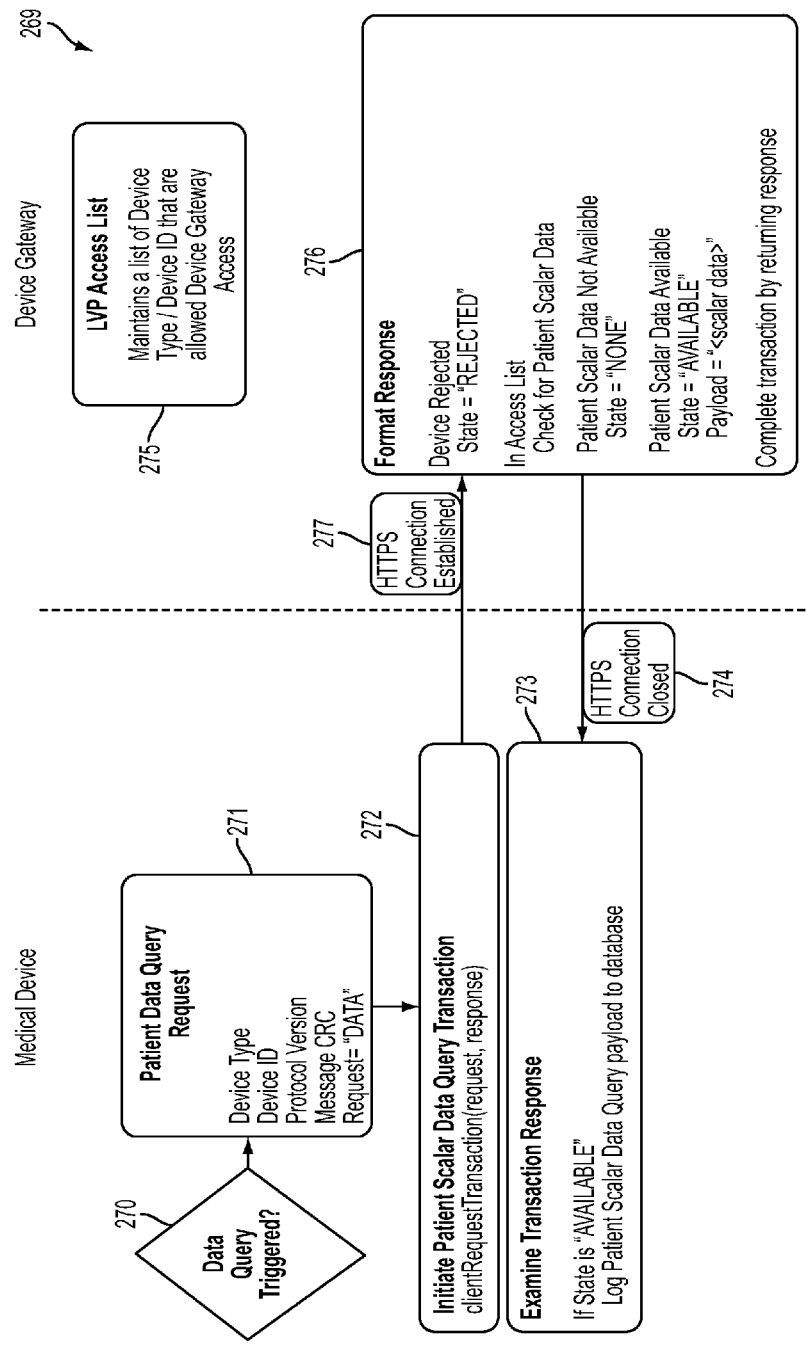
FIG. 19 shows a flow chart illustrating a method of communication between a medical device and a device gateway to perform a patient scalar data transaction in accordance with an embodiment of the present disclosure.

FIG. 19 shows a flow chart illustrating a method 269 of communication between a medical device and a device gateway to perform a patient scalar data transaction in accordance with an embodiment of the present disclosure. The Patient Scalar Data Check transaction (implemented by method 269) is initiated by the medical device to retrieve the available patient scalar data from the device gateway. The transaction is initiated whenever a DATA AVAILABLE has been received from a previous Communication Status Check transaction.

In act 270, the method 269 is triggered. In act 271, the request is initiated which is formatted as a web method in act 272. The web method is communicated via a HTTPS connection established in act 277 from the medical device to the device gateway. The device gateway formats a response to act 276. If the medical device is not a member of the device gateway's device access list 275 the state is set to REJECTED. If the medical device is a member of the device gateway's device access list 275 and the patient related scalar data is not available, the state is set to NONE. If the medical device is a member of the device gateway's device access list 275 and the patient related scalar data is available, the state is set to AVAILABLE and the response payload includes or references a text-based scalar data. The patient scalar data may be any data related to a patient, such as patient age, weight, allergies, sex, height, etc. The response to communicated and in act 274, the HTTPS connection is closed. In act 273, the medical device examines (e.g., processes and uses) the response.

Figure 20:
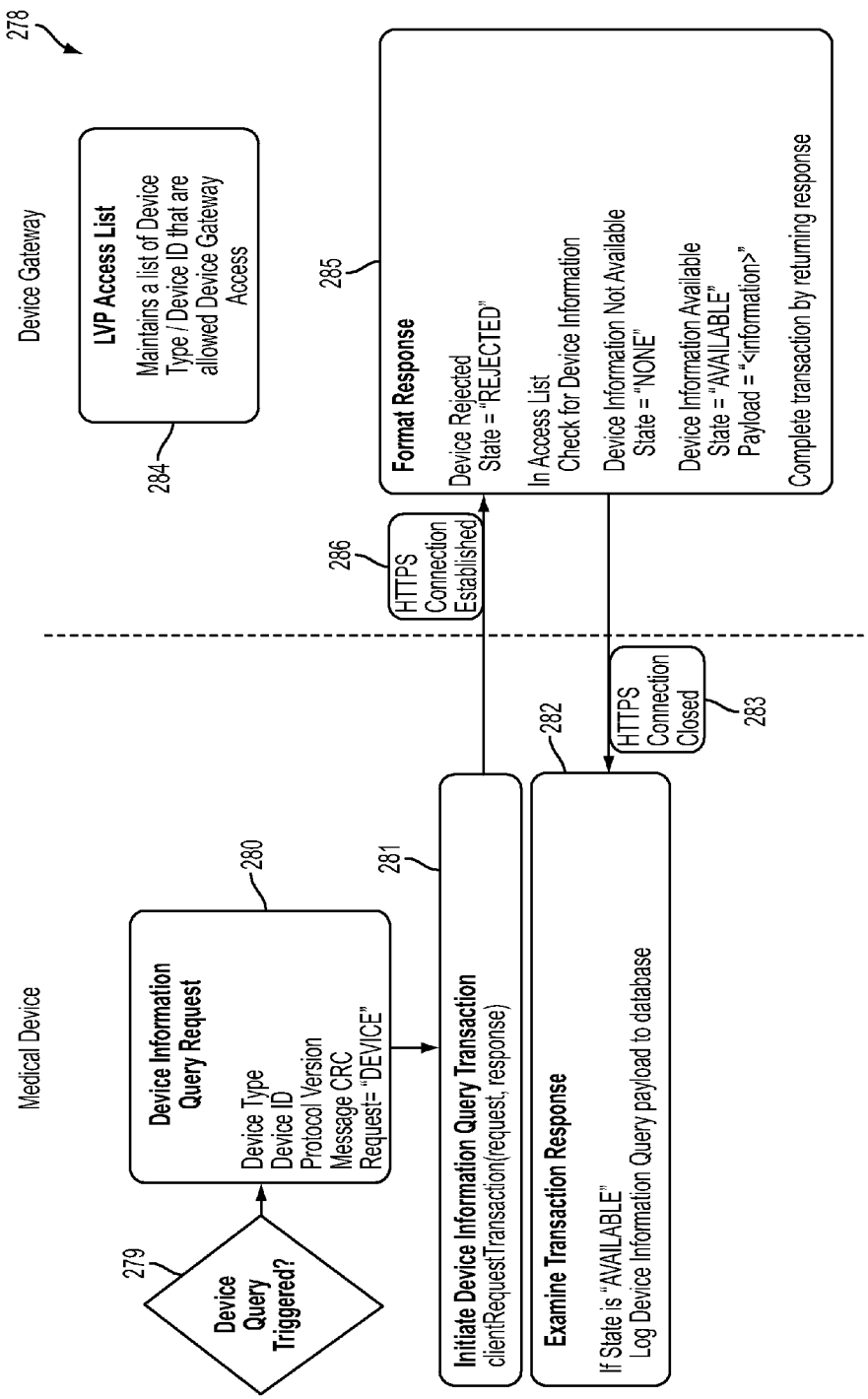
FIG. 20 shows a flow chart illustrating a method of communication between a medical device and a device gateway to perform a device information transaction sequence in accordance with an embodiment of the present disclosure

FIG. 20 shows a flow chart illustrating a method 278 of communication between a medical device and a device gateway to perform a device information transaction sequence in accordance with an embodiment of the present disclosure. The Device Information Check transaction (implemented as method 278) is initiated to retrieve the available device information from the device gateway. The transaction is initiated whenever a DEVICE AVAILABLE has been received from a previous Communication Status Check transaction.

In act 279, the method 278 is initiated. In act 280, the device information query request is initiated and in act 281 the web method is formatted. The web method is communicated to the device gateway via an HTTPS connection that is established in act 286. In act 285, a response is formatted. If the medical device is not a member of the device gateway's device access list 275 the state is set to REJECTED. If the medical device is a member of the device gateway's device access list 275 and the device information is not available, the state is set to NONE. If the medical device is a member of the device gateway's device access list 275 and the device information is available, the state is set to AVAILABLE and the response payload includes or references text-based device information. In some embodiments, the text-based device information may be any information related to device gateway or the medical device. The response is communicated to the medical device and the HTTPS connection is closed in act 283. In act 282 the medical device examines the response.

Figure 21:
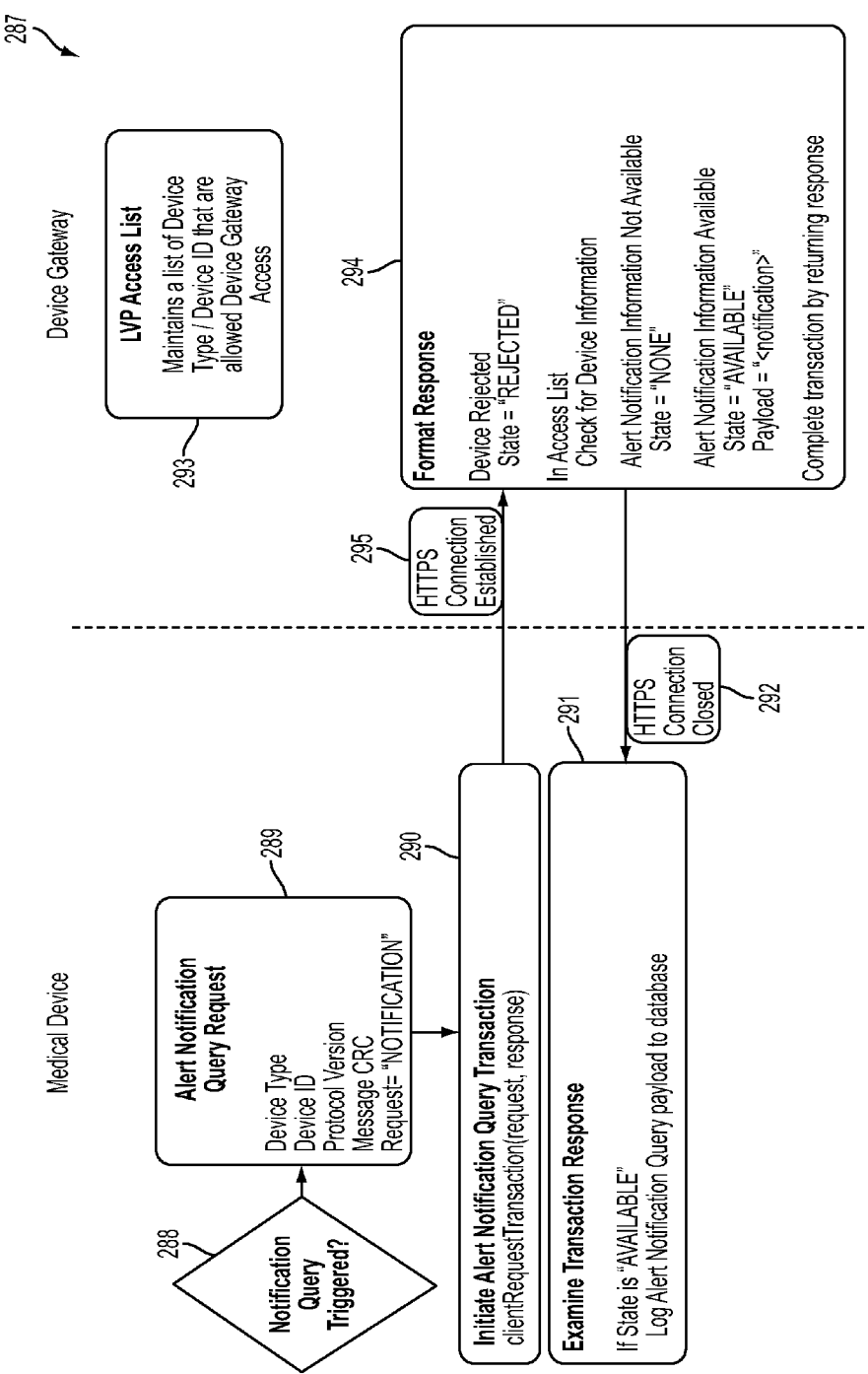
FIG. 21 shows a flow chart illustrating a method of communication between a medical device and a device gateway to perform an alert notification transaction in accordance with an embodiment of the present disclosure.

FIG. 21 shows a flow chart illustrating a method 287 of communication between a medical device and a device gateway to perform an alert notification transaction in accordance with an embodiment of the present disclosure. The Alert Notification Check transaction (implemented by method 287) is initiated to retrieve the available alert notifications from the device gateway. The transaction is initiated whenever a NOTIFICATION AVAILABLE has been received from a previous Communication Status Check transaction.

In act 288, the method 287 is initiated. In act 289, the alert notification query request is initiated and in act 295 the web method is formatted. The web method is communicated to the device gateway via an HTTPS connection that is established in act 295. In act 294, a response is formatted. If the medical device is not a member of the device gateway's device access list 275 the state is set to REJECTED. If the medical device is a member of the device gateway's device access list 275 and an alert notification is not available, the state is set to NONE. If the medical device is a member of the device gateway's device access list 275 and an alert notification is available, the state is set to AVAILABLE and the response payload includes or references text-based alert notifications. In some embodiments, the text-based alert notification may be any information related to an alert of the device gateway or the medical device. The response is communicated to the medical device and the HTTPS connection is closed in act 295. In act 291 the medical device examines the response.

Figure 22:
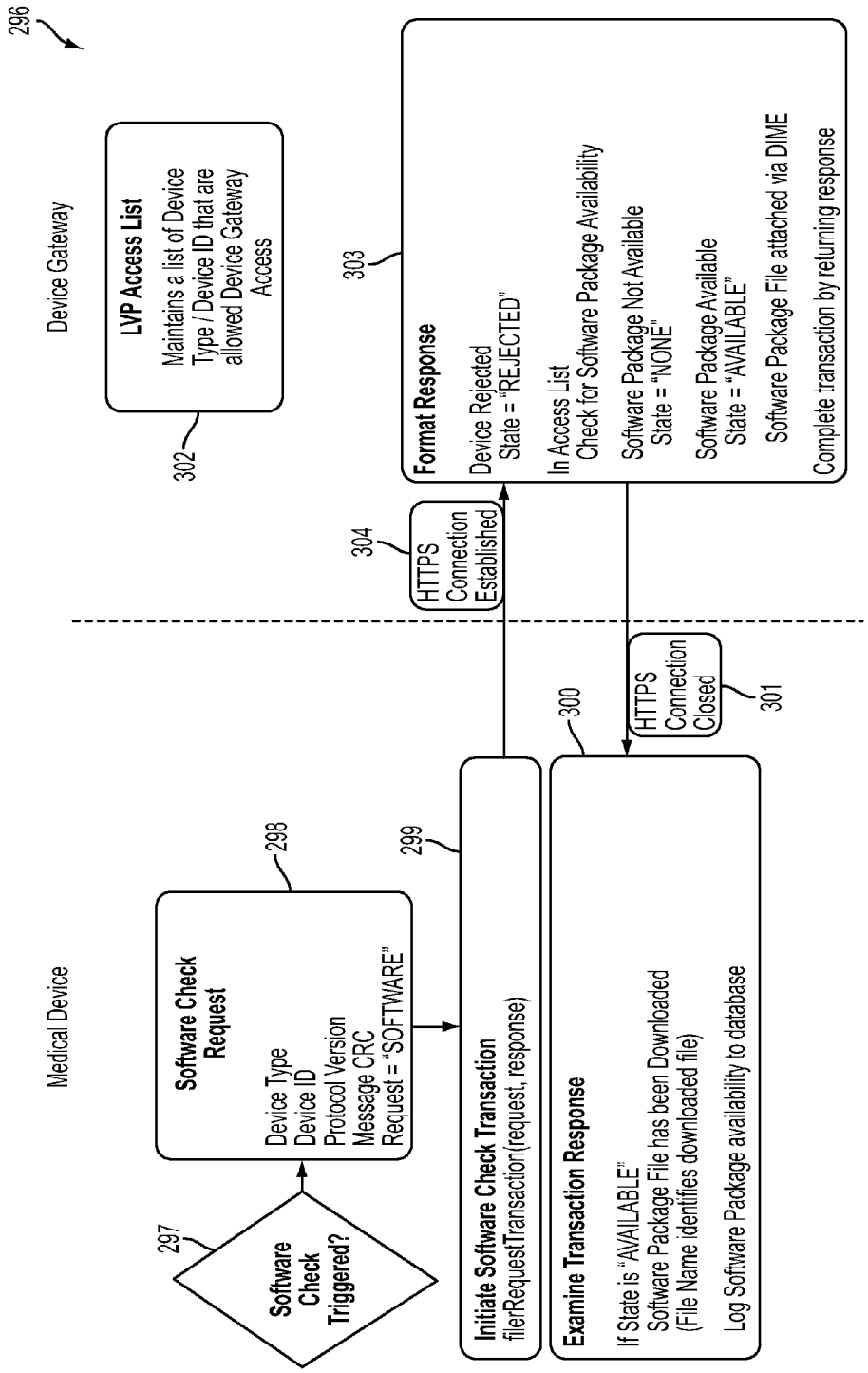
FIG. 22 shows a flow chart illustrating a method of communication between a medical device and a device gateway to perform a software package check transaction in accordance with an embodiment of the present disclosure.

FIG. 22 shows a flow chart illustrating a method 296 of communication between a medical device and a device gateway to perform a software package check (e.g., a debian software package) transaction (implemented as method 296) in accordance with an embodiment of the present disclosure. The Software Package Check transaction is initiated to retrieve the available software package from the device gateway. The transaction is initiated whenever a SOFTWARE AVAILABLE has been received from a previous Communication Status Check transaction.

In act 297, the method 269 is triggered. In act 298, the request is initiated which is formatted as a web method in act 299. The web method is communicated via a HTTPS connection established in act 304 from the medical device to the device gateway. The device gateway formats a response to act 303. If the medical device is not a member of the device gateway's device access list 275 the state is set to REJECTED. If the medical device is a member of the device gateway's device access list 275 and the software package is not available, the state is set to NONE. If the medical device is a member of the device gateway's device access list 275 and the software package is available, the state is set to AVAILABLE and the response payload includes (or references) a software package file (e.g., using DIME). The response is communicated and in act 301, the HTTPS connection is closed. In act 300, the medical device examines (e.g., processes and uses) the response.

Figure 23:
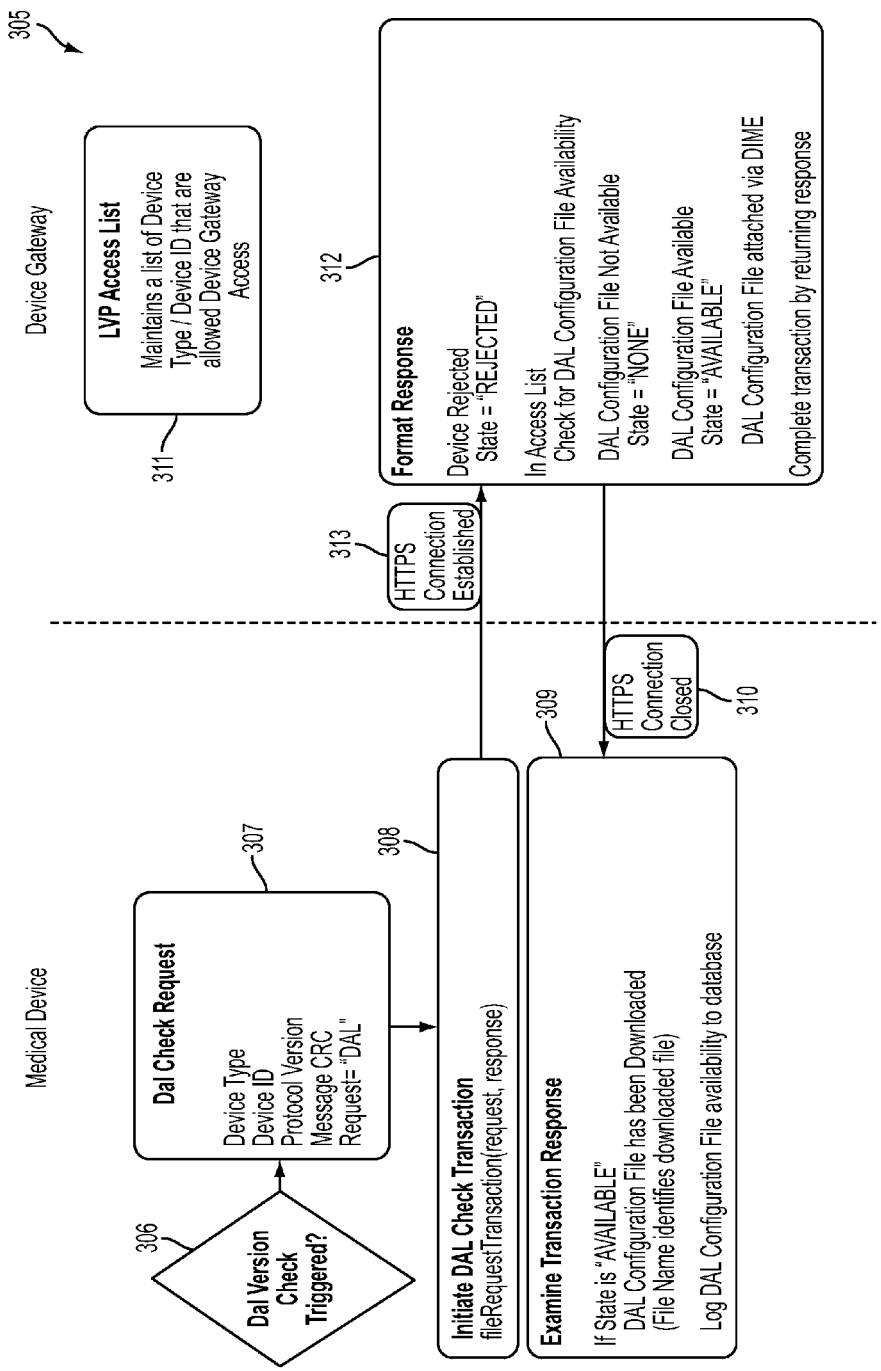
FIG. 23 shows a flow chart illustrating a method of communication between a medical device and a device gateway to perform a dose administration library configuration file check transaction in accordance with an embodiment of the present disclosure.

FIG. 23 shows a flow chart illustrating a method 305 of communication between a medical device and a device gateway to perform a DAL configuration file check transaction in accordance with an embodiment of the present disclosure. The DAL Configuration File Check transaction (implemented as method 305) is initiated to retrieve the available DAL file from the device gateway. The transaction is initiated whenever a DAL AVAILABLE has been received from a previous Communication Status Check transaction.

Act 306 initiates the method 305. The request is initiated in act 306, and the request is formatted as a web method in act 308. The medical device communicates the web method to the device gateway by establishing a HTTPS connection in act 313. In act 312, a response is formatted. If the medical device is not a member of the device gateway's device access list 311, the state is set to REJECTED, otherwise it is set to AVAILABLE. If the state is set to AVAILABLE, the device gateway formats the response payload to include the DAL configuration file (which may be attached using DIME). The response is communicated to the medical device and in act 310, the HTTPS connection is closed. Act 309 examines the response by the device gateway. The new DAL file may then be installed on the medical device.

Figure 24:
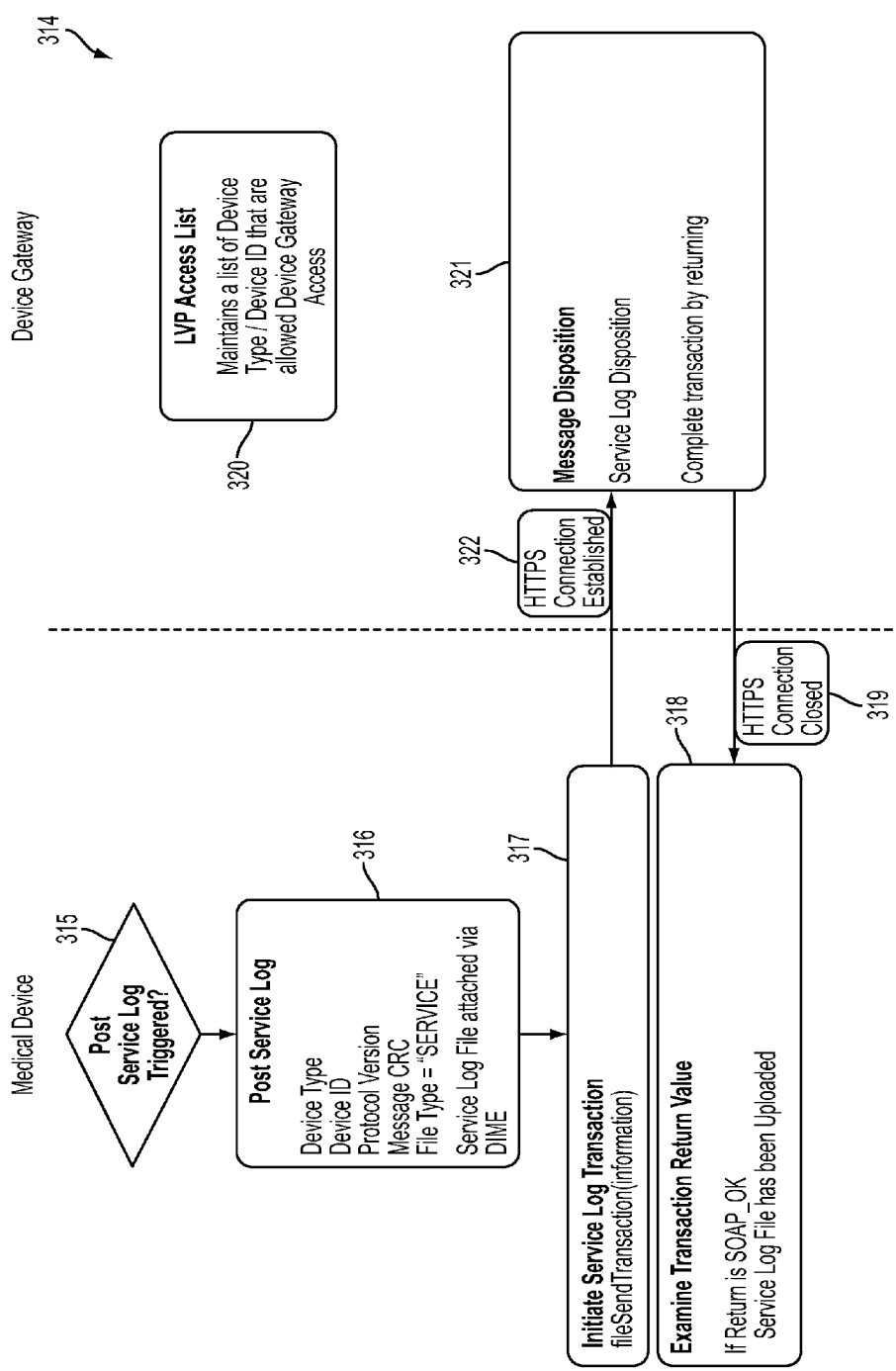
FIG. 24 shows a flow chart illustrating a method of communication between a medical device and a device gateway to perform a service log post transaction in accordance with an embodiment of the present disclosure.

FIG. 24 shows a flow chart illustrating a method 314 of communication between a medical device and a device gateway to perform a service log post transaction in accordance with an embodiment of the present disclosure. The Service Log Post transaction (implemented as method 314) is initiated to send the service log to the device gateway. The transaction is initiated whenever a SERVICELOG REQUEST has been received from a previous Communication Status Check transaction.

Act 315 receives the trigger and initiates the method 314. Act 316 initiates the post service log which is formatted into a web method in act 317. The web method is transmitted to the device gateway via an HTTPS connection that is established in act 322. Act 321 processes the web method and formats a response. The device gateway may write the information to a log file or communicate the service log post as a CQI message and sent it to cloud services (as described above). The response is communicated to the medical device which examines the transaction response in act 317 (e.g., by examining the return value to determine if it was a successful service log post). Act 319 closes the HTTPS connection after the response is transmitted.

Figure 25:
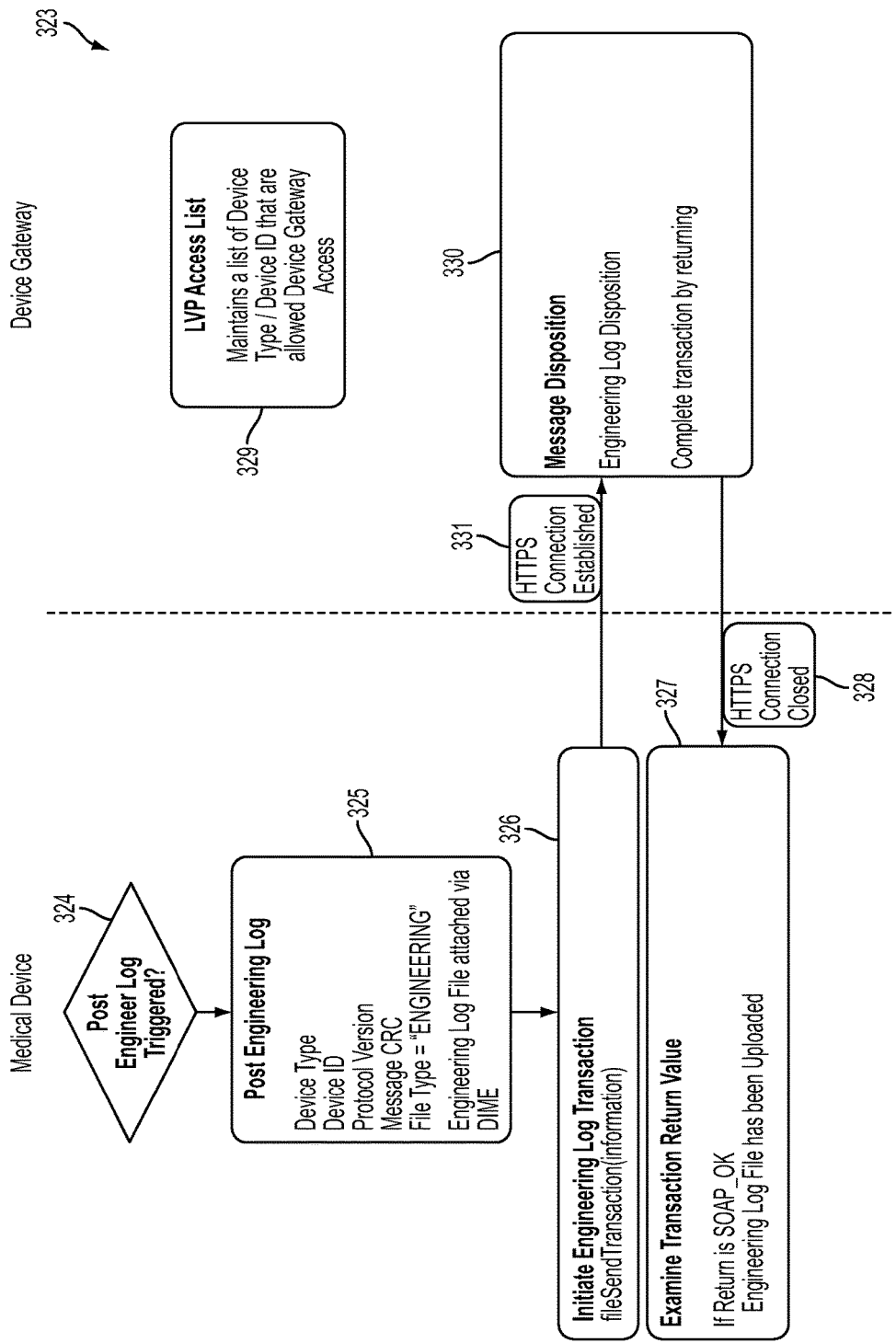
FIG. 25 shows a flow chart illustrating a method of communication between a medical device and a device gateway to perform an engineering log post transaction in accordance with an embodiment of the present disclosure.

FIG. 25 shows a flow chart illustrating a method 232 of communication between a medical device and a device gateway to perform an engineering log post transaction in accordance with an embodiment of the present disclosure. The Engineering Log Post transaction is initiated to send the engineering log to the device gateway. The transaction is initiated whenever an ENGINEERINGLOG REQUEST has been received from a previous Communication Status Check transaction.

Act 324 receives the trigger and initiates the method 323. Act 325 initiates the post engineering log which is formatted into a web method in act 326. The web method is transmitted to the device gateway via an HTTPS connection that is established in act 331. Act 330 processes the web method and formats a response. IF the medical device is an authorized medical device as indicated by the access list 239, the device gateway may write the information to a log file or communicate the service log post as a CQI message and sent it to cloud services (as described above). The response is communicated to the medical device which examines the transaction response in act 327 (e.g., by examining the return value to determine if it was a successful engineering log post). Act 328 closes the HTTPS connection after the response is transmitted.

Figure 26:
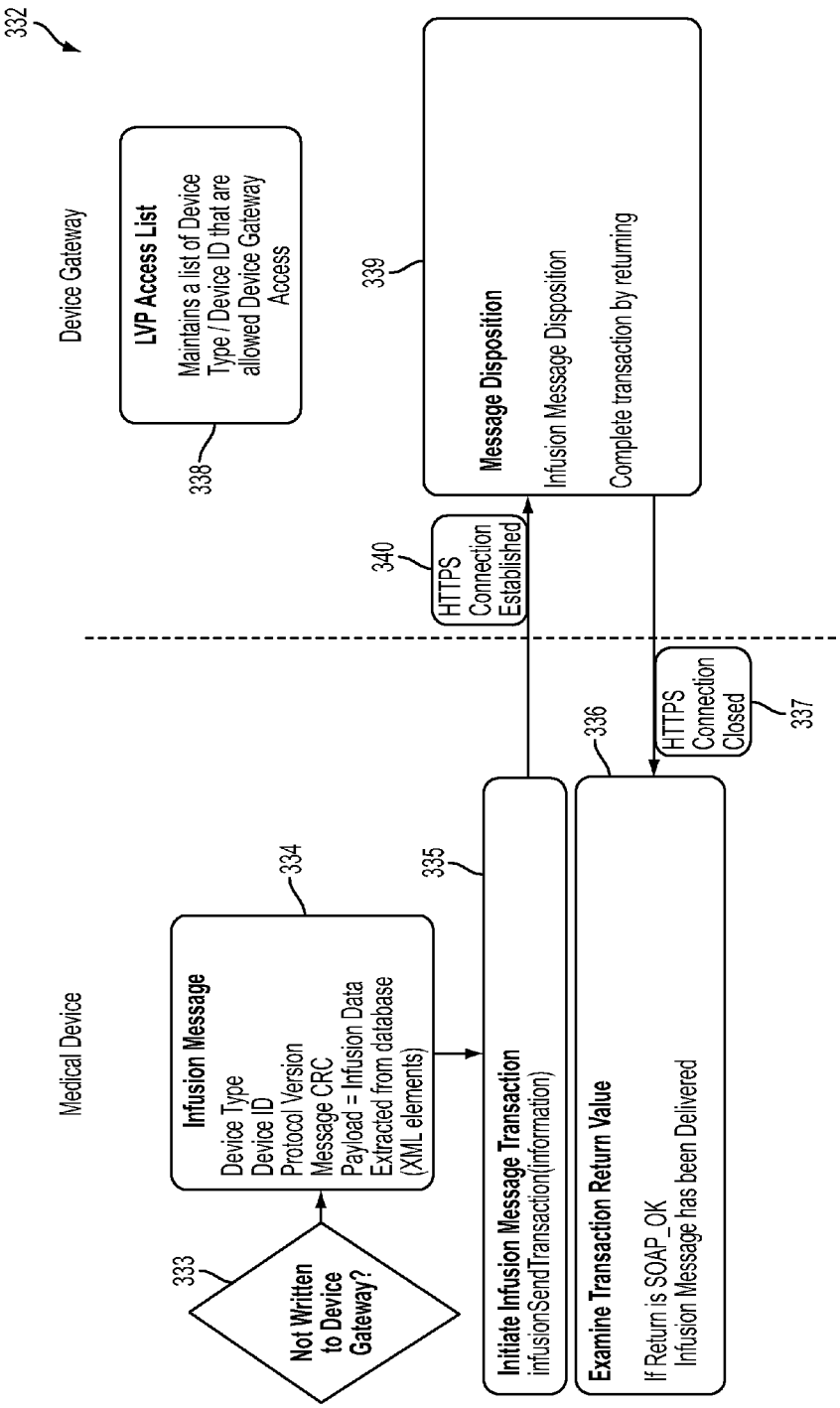
FIG. 26 shows a flow chart illustrating a method of communication between a medical device and a device gateway to perform an infusion log post transaction in accordance with an embodiment of the present disclosure.

FIG. 26 shows a flow chart illustrating a method 332 of communication between a medical device and a device gateway to perform an infusion log post transaction in accordance with an embodiment of the present disclosure. The Infusion Log Post transaction (implemented as method 332) is initiated to send XML formatted infusion event information to the device gateway. The transaction is initiated whenever infusion event information is available that has not been previously sent to the device manager. DGCM 342 marks the record as delivered if the transaction is successful.

Act 333 receives the trigger and initiates the method 332. Act 334 initiates the infusion log post which is formatted into a web method in act 335. The web method is transmitted to the device gateway via an HTTPS connection that is established in act 340. Act 339 processes the web method and formats a response. The device gateway may write the information to a log file or communicate the infusion log post as a CQI message and sent it to the cloud services (as described above). The response is communicated to the medical device which examines the transaction response in act 336 (e.g., by examining the return value to determine if it was a successful infusion log post). Act 337 closes the HTTPS connection after the response is transmitted.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A system for electronic patient care, the system comprising:
   a network;
   a facility gateway configured to provide a publish-subscribe service for an application; and
   a device gateway application configured for execution by the facility gateway, the device gateway is configured to communicate via the network by providing a web service;
   a medical device in operative communication with the network, wherein:
      only the medical device is configured to communicate with the device gateway using the web service,
      the medical device initiates communications with the device gateway using the web service at predetermined intervals of time to request a response payload, the device gateway configured to be prevented from initiating communications with the medical device;
      the device gateway determines whether the medical device is listed on an access list of medical devices that can access the device gateway;
      in response to the medical device initiated communication by the medical device determined to be on the access list, the device gateway formats the response payload comprising an availability of a software update, an availability of a queryable data type, and a plurality of current request statuses, wherein each current request status is a request for the medical device to transmit a data type of a plurality of data types to the device gateway,
      the device gateway communicates the response payload to the medical device in response to the medical device initiated communication, and
      the medical device communicates all data types of the plurality of data types where a respective current request status of the current request statutes indicates a request of a respective data type; and
   a publish-subscribe engine configured to provide the publish-subscribe service for communication between a plurality of applications including the device gateway application, the plurality of applications being executed within the facility gateway.

2. The system according to claim 1, wherein the network is a TCP/IP-based network.

3. The system according to claim 1, wherein the device gateway application is a web server of the web service and the medical device is a client of the web service.

4. The system according to claim 1, wherein the device gateway application is configured to register a topic using the publish-subscribe service.

5. The system according to claim 4, further comprising an integration API configured for execution by the facility gateway, wherein the integration API is configured to subscribe to the topic and communicate an event received by the subscription to the topic to at least one external server.

6. The system according to claim 5, wherein the topic is at least one of a reportable biomed events topic and a reportable clinical events topic.

7. The system according to claim 4, wherein the topic is a reportable biomed event topic and the device gateway reformats a medical device event received via the web service into a reportable biomed event receivable by a subscriber to the topic via the publish-subscribe engine.

8. The system according to claim 7, wherein the medical device communicates the medical device event via the network using the web service.

9. The system according to claim 4, wherein the topic is a reportable clinical event topic and the device gateway reformats a medical device event received via the web service into a reportable clinical event receivable by a subscriber to the topic via the publish-subscribe engine.

10. The system according to claim 9, wherein the medical device communicates the medical device event via the network using the web service.

11. The system according to claim 4, wherein the topic corresponds to at least one class of pump events.

12. The system according to claim 11, wherein the at least one class of pump events includes at least one of an infusion event regarding an alarm, alert or notification, an infusion event regarding infusing, an infusion event regarding programming, a device event regarding communication, a device event regarding an access request, a device event regarding configuration updates, a device event regarding logging, and a device event regarding power consumption.

13. The system according to claim 1, further comprising a continuous quality improvement listener configured for execution by the facility gateway, wherein:
   the continuous quality improvement listener subscribes to a reportable biomed event topic and to a reportable clinical even topic,
   the continuous quality improvement is configured to communicate a reportable biomed event received by the subscription to the reportable biomed event topic to an external database, and
   the continuous quality improvement is configured to communicate a reportable clinical event received by the subscription to the reportable clinical event topic to an external database.

14. The system according to claim 13, wherein the external database records at least one of the reportable biomed event and the reportable clinical event.

15. The system according to claim 1, further comprising a device manager executable on the facility gateway, wherein the device manager is configured to maintain a list of medical devices including the medical device.

16. The system according to claim 15, wherein the list of the medical devices includes a list of serial numbers corresponding to the list of medical devices.

17. The system according to claim 1, further comprising a monitoring client in operative communication with the medical device through the network to receive status information therefrom.

18. A system for electronic patient care, the system comprising:
   a network;
   a facility gateway configured to provide a publish-subscribe service;
   a device gateway application configured for execution by the facility gateway, the device gateway is configured to communicate via the network by providing a web service, wherein the device gateway publishes a medical device event topic;
   a device application configured for execution on the facility gateway and configured to subscribe to the medical device event topic, wherein the device application publishes a Continuous Quality Improvement ("CQI")-message topic, and wherein the device application is configured to receive an event from the subscription to the medical device event topic and publish the event as a CQI message through the CQI-message topic;
   a medical device in operative communication with the network, wherein:
      only the medical device is configured to communicate with the device gateway using the web service and to generate the event using a web method of the web service,
      the medical device initiates communications with the device gateway using the web service at predetermined intervals of time to request a response payload, the device gateway configured to be prevented from initiating communications with the medical device;
      the device gateway determines whether the medical device is listed on an access list of medical devices that can access the device gateway;
      in response to the medical device initiated communication by the medical device determined to be on the access list, the device gateway formats the response payload comprising an availability of a software update, an availability of a queryable data type, and a plurality of current request statuses, wherein each current request status is a request for the medical device to transmit a data type of a plurality of data types to the device gateway,
      the device gateway communicates the response payload to the medical device in response to the medical device initiated communication, and
      the medical device communicates all data types of the plurality of data types where a respective current request status of the current request statutes indicates a request of a respective data type; and
   a publish-subscribe engine configured to provide the publish-subscribe service for communication between a plurality of applications including the device gateway application and the device application, the plurality of applications being executed within the facility gateway.

19. The system according to claim 18, wherein the device gateway subscribes to the CQI-message topic to receive the CQI-message.

20. The system according to claim 19, further comprising a CQI listener configured for execution by the facility gateway, wherein the CQI listener is subscribed to the CQI-message topic to receive the CQI message.

21. The system according to claim 20, wherein the CQI listener communicates the CQI-message to an external database.

22. The system according to claim 18, wherein the CQI message is one of a reportable biomed event and a reportable clinical event.

23. The system according to claim 18, further comprising a monitoring client configured to operatively communicate with the medical device.

24. The system according to claim 23, wherein the monitoring client communicates with the medical device by subscribing to the CQI-message topic.

* * * * *